(12) United States Patent
Thomas et al.

(10) Patent No.: US 6,184,225 B1
(45) Date of Patent: Feb. 6, 2001

(54) QUINAZOLINE DERIVATIVES AS VEGF INHIBITORS

(75) Inventors: Andrew Peter Thomas; Craig Johnstone, both of Macclesfield (GB); Laurent Francois Andre Hennequin, Reims Cedex (FR)

(73) Assignee: Zeneca Limited, London (GB)

( * ) Notice: Under 35 U.S.C. 154(b), the term of this patent shall be extended for 0 days.

(21) Appl. No.: 09/125,271

(22) PCT Filed: Feb. 10, 1997

(86) PCT No.: PCT/GB97/00365
§ 371 Date: Aug. 13, 1998
§ 102(e) Date: Aug. 13, 1998

(87) PCT Pub. No.: WO97/30035
PCT Pub. Date: Aug. 21, 1997

(30) Foreign Application Priority Data

| Feb. 13, 1996 | (EP) | 96400293 |
| Aug. 8, 1996 | (EP) | 96401756 |
| Dec. 17, 1996 | (EP) | 96402764 |

(51) Int. Cl.[7] .................. A01N 43/54; C07D 239/00; C07D 239/72
(52) U.S. Cl. .................. 514/259; 514/259; 544/245; 544/287; 544/293
(58) Field of Search .................. 544/245, 287, 544/293; 514/259

(56) References Cited

U.S. PATENT DOCUMENTS

| 3,266,990 | 8/1966 | Lutz et al. | 514/259 |
| 4,343,940 | 8/1982 | Kreighbaum et al. | 544/283 |
| 5,409,930 | 4/1995 | Spada et al. | 514/248 |
| 5,457,105 | 10/1995 | Barker | 514/234.5 |
| 5,480,883 | 1/1996 | Spada et al. | 514/249 |
| 5,639,757 | 6/1997 | Dow et al. | 514/261 |
| 5,646,153 | 7/1997 | Spada et al. | 514/259 |
| 5,650,415 | 7/1997 | Tang et al. | 514/312 |
| 5,656,643 | 8/1997 | Spada et al. | 514/312 |
| 5,710,158 | 1/1998 | Myers et al. | 514/259 |
| 5,712,395 | 1/1998 | App et al. | 544/344 |
| 5,714,493 * | 2/1998 | Myers et al. | 514/259 |
| 5,721,237 | 2/1998 | Myers et al. | 514/259 |
| 5,736,534 | 4/1998 | Arnold | 514/63 |
| 5,747,498 | 5/1998 | Schnur et al. | 514/259 |
| 5,792,771 | 8/1998 | App et al. | 514/259 |
| 5,962,458 * | 10/1999 | Lohmann et al. | 514/259 |

FOREIGN PATENT DOCUMENTS

| 02213558 | 10/1972 | (DE) . |
| 29 36 705 | 3/1980 | (DE) . |
| 19521386 | 12/1996 | (DE) . |
| 19608588 | 9/1997 | (DE) . |
| 19608631 | 9/1997 | (DE) . |
| 19608653 | 9/1997 | (DE) . |
| 19614718 | 10/1997 | (DE) . |
| 19629652 | 1/1998 | (DE) . |

(List continued on next page.)

OTHER PUBLICATIONS

Arya et al., Nitroimidazoles: Part XVI—Some 1–Methyl–4–nitro–5–substituted Imidazoles, Indian Journal of Chemistry, vol. 21B, Dec. 1982, pp. 1115–1117.*

Bridges, "The current status of tyrosine kinase inhibitors . . . ," Exp.Opin.Ther.Patents (1995), 5(12): 1245–1257, Editorial, Oncologic, Endocrine & Metabolic, 1995 Ashley Publications Ltd ISSN 1354–3776.*

(List continued on next page.)

Primary Examiner—Richard L. Raymond
Assistant Examiner—Ben Schroeder
(74) Attorney, Agent, or Firm—Pillsbury Madison & Sutro LLP; Intellectual Property Group

(57) ABSTRACT

The invention relates to quinazoline derivatives of formula (I)

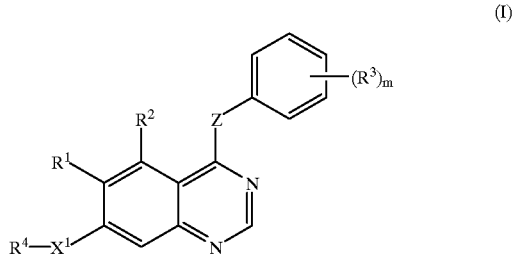

wherein: Z represents —O—, —NH— or —S—; m is an integer from 1 to 5; $R^1$ represents hydrogen, hydroxy, halogeno, nitro, trifluorometlyl, cyano, $C_{1-3}$alkyl, $C_{1-3}$alkoxy, $C_{1-3}$alkylthio or $NR^5R^6$ (wherein $R^5$ and $R^6$, which may be the same or different, each represents hydrogen or $C_{1-3}$alkyl); $R^2$ represents hydrogen, hydroxy, halogeno, methoxy, amino, or nitro; $R^3$ represents hydroxy, halogeno, $C_{1-3}$alkyl, $C_{1-3}$alkoxy, $C_{1-3}$alkanoyloxy, trifluoromethyl, cyano, amino or nitro; $X^1$ represents —O—, —$CH_2$—, —S—, —SO—, $SO_2$—, —$NR^6$—, $NR^8CO$—, —$CONR^9$—$SO_2NR^{10}$— or —$NR^{11}SO_2$—, (wherein $R^7$, $R^8$, $R^9$, $R^{10}$ and $R^{11}$ each represents $C_{1-3}$alkyl, $C_{1-3}$alkoxy$C_{2-3}$alkyl); $R^4$ represents a group which is alkenyl, alkynyl or optionally substituted alkyl, which alkyl group may contain a heteroatom linking group, which alkenyl, alkynyl or alkyl group may carry a terminal optionally substituted 5 or 6 membered saturated carbocyclic or heterocyclic group; and salts thereof, processes for their preparation, pharmaceutical compositions containing a compound of formula (I) or a pharmaceutically acceptable salt thereof as active ingredient the compounds of formula (I) and the pharmaceutically acceptable salts thereof inhibit the effects of VEGF, a property of value in the treatment of a number of disease states including cancer and rheumatoid arthritis.

18 Claims, No Drawings

U.S. PATENT DOCUMENTS

| | | |
|---|---|---|
| 0 326 307 A2 | 2/1989 | (EP) . |
| 326 330 | 8/1989 | (EP) . |
| 520 722 | 12/1992 | (EP) . |
| 566 226 | 10/1993 | (EP) . |
| 0 602 851 A1 | 6/1994 | (EP) . |
| 0 635 507 A1 | 1/1995 | (EP) . |
| 635 498 | 1/1995 | (EP) . |
| 0 682 027 A1 | 11/1995 | (EP) . |
| 0 743 308 | 11/1996 | (EP) . |
| 0 787 722 A1 | 8/1997 | (EP) . |
| 0 795 556 | 9/1997 | (EP) . |
| 0 837 063 A1 | 4/1998 | (EP) . |
| 2 033 894 | 5/1980 | (GB) . |
| 2 160 201 | 12/1985 | (GB) . |
| 54-2327 | 4/1979 | (JP) . |
| WO 87/04321 | 7/1987 | (WO) . |
| WO 92/14716 | 9/1992 | (WO) . |
| WO 92/16527 | 10/1992 | (WO) . |
| 92 20642 | 11/1992 | (WO) . |
| WO 95/06648 | 3/1995 | (WO) . |
| WO 95/15952 | 6/1995 | (WO) . |
| WO9515758 * | 6/1995 | (WO) . |
| WO 95/19169 | 7/1995 | (WO) . |
| WO 95/19774 | 7/1995 | (WO) . |
| WO 95/19970 | 7/1995 | (WO) . |
| WO 95/21613 | 8/1995 | (WO) . |
| WO 95/23141 | 8/1995 | (WO) . |
| WO 95/24190 | 9/1995 | (WO) . |
| WO 96/07657 | 3/1996 | (WO) . |
| WO 96/09294 | 3/1996 | (WO) . |
| WO 96/15118 | 5/1996 | (WO) . |
| WO 96/16960 | 6/1996 | (WO) . |
| WO 96/29331 | 9/1996 | (WO) . |
| WO 93/33980 | 10/1996 | (WO) . |
| WO 96/30347 | 10/1996 | (WO) . |
| WO 96/30370 | 10/1996 | (WO) . |
| WO 96/31510 | 10/1996 | (WO) . |
| WO 96/33977 | 10/1996 | (WO) . |
| WO 96/33978 | 10/1996 | (WO) . |
| WO 96/33979 | 10/1996 | (WO) . |
| WO 96/33981 | 10/1996 | (WO) . |
| WO 96/34867 | 11/1996 | (WO) . |
| WO 96/35689 | 11/1996 | (WO) . |
| WO 96/39145 | 12/1996 | (WO) . |
| WO 96/40142 | 12/1996 | (WO) . |
| WO 96/40648 | 12/1996 | (WO) . |
| WO 97/02266 | 1/1997 | (WO) . |
| WO 97/03069 | 1/1997 | (WO) . |
| WO 97/13760 | 4/1997 | (WO) . |
| WO 97/13771 | 4/1997 | (WO) . |
| WO 97/14691 | 4/1997 | (WO) . |
| WO 97/16435 | 5/1997 | (WO) . |
| WO 97/17329 | 5/1997 | (WO) . |
| WO 97/18212 | 5/1997 | (WO) . |
| WO 97/22596 | 6/1997 | (WO) . |
| WO 97/28161 | 8/1997 | (WO) . |
| WO 97/30034 | 8/1997 | (WO) . |
| WO 9730044 | 8/1997 | (WO) . |
| WO 97/32856 | 9/1997 | (WO) . |
| WO 97/37999 | 10/1997 | (WO) . |
| WO 97/38983 | 10/1997 | (WO) . |
| WO 97/38994 | 10/1997 | (WO) . |
| WO 97/49688 | 12/1997 | (WO) . |
| WO 97/49689 | 12/1997 | (WO) . |
| WO 98/02434 | 1/1998 | (WO) . |
| WO 98/02437 | 1/1998 | (WO) . |
| WO 98/02438 | 1/1998 | (WO) . |
| WO 98/07726 | 2/1998 | (WO) . |
| WO 98/10767 | 3/1998 | (WO) . |
| WO 98/14431 | 4/1998 | (WO) . |
| WO 98/23613 | 6/1998 | (WO) . |

OTHER PUBLICATIONS

Bridges, et al., "Enantioselective Inhibition of the Epidermal Growth Factor Receptor Tyrosine Kinase by a 4–(a–Phenethylamino)quinazolines," Bioorganic & Medicinal Chemistry, vol. 3, No. 12, pp. 1651–1656, 1995.*

Buchdunger, et al., "4,5–Dianilinophthalimide: A protein–tyrosine kinase inhibitor with selectivity for the epidermal growth factor . . . ," Proc.Natl.Acad.Sci., USA, vol. 91, pp. 2334–2338, Mar. 1994, Applied Biological Sciences.*

Burke, Jr., "Protein–tyrosine kinase inhibitors," Drugs of the Future 1992, vol. 17(2), pp. 119–131.*

Connolly, et al., "Human Vascular Permeability Factor," J.Bio.Chem., vol. 264, No. 33, Nov. 1989, pp. 20017–20024.*

Cullinan–Bove, et al., "Vascular Endothelial Growth Factor/Vascular Permeability Factor Expression in the Rat Uterus . . . ," Endocrinology, vol. 133, No. 2, 1993, pp. 829–837.*

Dolle, et al., "5,7–Dimethoxy–3–(4–pyridinyl)quinoline Is a Potent and Selective Inhibitor of Human Vascular b–Type Platelet–Derived Growth Factor Receptor Tyrosine Kinase," J.Med.Chem. 1994, vol. 37, pp. 2627–2629.*

Fan, et al., "Controlling the Vasculature: Angiogenesis, Anti–Angiogenesis . . . ," TiPS Review, vol. 16, Feb. 1995, pp. 57–65.*

Folkman, "Angiogenesis in Cancer, Vascular, Rheumatoid and Other Disease," Nature Medicine, vol. 1, No. 1, 1995, pp. 27–30.*

Fry et al., "A Specific Inhibitor of the Epidermal Growth Factor Receptor Tyrosine Kinase," Science, vol. 265, Aug. 19, 1994, pp. 1093–1095.*

Gazit et al., Tyrophostins IV—Highly Potent Inhibitors . . . Relationship Study of 4–Anilidoquinazolines, Bioorganic & Medicinal Chemistry, vol. 4, No. 8, 1996, pp. 1203–1207.*

Golovkin et al., *Nauchin TR–VSES–Nauchno–Issled Inst Farm*, 1990, 28, 70–75.*

Hara et al., On the Amination of Azaheterocycles. A New Procedure for the Introduction of an Amino Group (1), J. Heterocyclic Chem. vol. 19, 1982, pp. 1285–1287.*

Higashino et al., Reactions of the Anion Reissert Compound . . . with Electrophiles, Chem. Pharm. Bull., vol. 33(3), 1985, pp. 950–961.*

Iyer, et al., "Studies in Potential Amoebicides: Part III—Synthesis of 4–Substituted Amino–8–Hydroxy) Quinazolines & 3–Substituted 8–Hydroxy(&8–Methoxy)–4–Quinazolones," J.Sci.Industr.Res., vol. 15C, Jan. 1956, pp. 1–7.*

Jakeman, et al., "Developmental Expression of Binding Sites and Messenger Ribonucleic Acid . . . ," Endocrinology, vol. 133, No. 2, 1993, pp. 848–859.*

Karminski et al., The Synthesis of Some Quinazoline Derivatives and Their Biological Properties; J. Environ. Sci. Health, vol. B18, 1993, pp. 599–610.*

Kim, et al., "Inhibition of Vascular Endothelial Growth Factor–Induced Angiogenesis Suppresses Tumour Growth in Vivo," Nature, vol. 362, Apr. 1993, pp. 841–844.*

Kobayashi, Derwent Abstract 82–87077, vol. 6, No. 244, Dec. 1982, JP 57–144266, Sep. 1982, "4–Anilinoquinazoline Derivative, its Preparation and Analgesic and Antiphlogistic Agent Containing Said Derivative as Active Component". (n7).*

Kolch, et al., "Regulation of the Expression of the VEGF/VPS and its Receptors: Role in Tumor Angiogenesis," Breast Cancer Research and Treatment, vol. 36, 1995, pp. 139–155.*

Kumar et al., Reactions of Diazines with Nucleophiles—IV.1 The Reactivity . . . Single Electron Transfer Reactions, Bioorganic & Medicinal Chemistry, vol. 3, No. 7, 1995, pp. 891–897.*

Kyorin, Derwent Abstract 84–53835, JP 59–13765, Jan. 1984, "2–(4–Quinazolinyl)amino benzoic acid derivs . . . having analgesic and antiiflammatory activities", (n.8).*

Li, et al., Chem.Abs., vol. 92:76445u, 1980, p.674–675.*

Lin et al., Chem.Abs., vol. 96:122728w, 1982, p.695.*

Maguire, et al., "A New Series of PDGF Receptor Tyrosine Kinase Inhibitors: 3–Substituted Quinoline Derivatives," J.Med.Chem. 1994, vol. 37, pp. 2129–2137.*

Nagarajan et al., Nitroimidazoles: Part XIX†—Structure Activity Relationships‡, Indian Journal of Chemistry, vol. 23B, Apr. 1984, pp. 342–362.*

Nomoto et al., Studies on Cardiotonic Agents. VII.1) Potent Cardiotonic Agent KF15232 with Myofibrillar CA2+ Sensitizing Effect, Chem. Pharm. Bull., vol. 39(4), 1991, pp. 900–910.*

Rewcastle et al., "Tyrosine Kinase Inhibitors . . . 4–(Phenylamino)quinazolines as Potent . . . Inhibitors of the Tyrosine Kinase Domain of the Epidermal Growth Factor Receptor," J.Med.Chem. 1995, vol. 38, pp. 3482–3487.*

Sankyo and Ube, Derwent Abstract 81–28290, JP 56–20577, Feb. 1981, "4–(N–alkyl:anilino) quinazoline derivs . . . having analgesic and antiinflammatory actions". (n.9).*

Schonowsky et al., Chinazolinderivative, ihre Herstellung und biologische Wirkung, Quinzaolines, their Preparation and Biological Activity, Z. Naturforsch, 37b, 1982, pp. 907–911.*

Senger, et al., "Vascular Permeability Factor (VPF, VEGF) in Tumor Biology," Cancer and Metastasis Reviews, vol. 12, 1993, pp. 303–324.*

Sinyak, et al., Synthesis and Biological Properties of Derivatives of 4–Heterylmercaptoquinazoline, Zaporozh'e Medical Institute pp. 103–106, translated from Khimiko–farmatsevticheskii Zhurnal, vol. 20, No. 2, Feb. 1986, 168–171, original article submitted Dec. 29, 1984.*

Spada, et al., Small molecule inhibitors of tyrosine Kinase activity, Exp.Opin.Ther.Patents (1995), 5(8):805–817, Patent Update, Oncologic, Endocrine & Metabolic, Ashley Publications Ltd. ISSN 1354–3776.*

Spence, "Inhibitors of Tyrosine Kinase Activity as Anticancer Therapeutics: Recent Developments," Expert Opinion in Therapeutic Patents, Jan. 1993, Patent Update, Anticancers, etc., pp. 3–9, Current Drugs Ltd ISSN 0962–2594.*

Stets et al., Investigation of Anti–Arrhythmic Action of Quinazopyrine, Pharmacology Dept., Zaporozhye Medical Institute, Zaporozhye, and Vinnitsa Medical Institute, Vinnitsa, pp. 94–96, translated from Farmakol. 1 toksik., vol. 53, No. 3, 1990, pp. 15–17.*

Traxler, et al., "Recent advances in protein tyrosine kinase inhibitors," Drugs of the Future 1995, vol. 20(12, pp. 1261–1274.*

Trinks, et al., "Dianilinophthalimides: Potent and Selective, ATP–Competitive Inhibitors of the EGF–Receptor Protein Tyrosine Kinase," J.Med. Chem. 1994, vol. 37, pp. 1015–1027.*

Vinogradoff et a;/, Development of a New Synthesis of . . . Sodium Salt via an Amidine Intermediate, J. Heterocyclic Chem. vol. 26, 97, Jan.–Feb. 1989, pp. 97–103.*

Ward, et al., "Epidermal Growth Factor Receptor Tyrosine Kinase—Investigation of Catalytic Mechanism, Structure- –Based Searching and Discovery of a Potent Inhibitor," Biochem. Pharmacology, vol. 48, No. 4, pp. 659–666 (1994).*

Wolfe et al., A Facile One–Step Synthesis of Certain 4–(4–Pyrimidinylmethyl)quinazolines, J. Heterocyclic Chem., vol. 13, 1976, pp. 383–385.*

* cited by examiner

QUINAZOLINE DERIVATIVES AS VEGF INHIBITORS

This application is the national phase of international application PCT/GB97/00365 filed Feb. 10,1997 which designated the U.S.

The present invention relates to quinazoline derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Alteration of vascular permeability is thought to play a role in both normal and pathological physiological processes (Cullinan-Bove et al, 1993) Endocrinology 133: 829–837; Senger et al, 1993, Cancer and Metastasis Reviews. 12: 303–324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36:139–155) and vascular permeability (Connolly et al, 1989, J. Biol. Chem. 264: 20017–20024). Antagonism of VEGF action by sequestration of VEGF with antibody can result in inhibition of tumour growth (Kim et al, 1993, Nature 362: 841–844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells has been associated with changes in the tyrosine phosphorylation status of cellular proteins and calcium fluxes.

Compounds which have good activity against epidermal growth factor (EGF) receptor tyrosine kinase are disclosed in the European Patent Publication No 0566226, but there is no disclosure or suggestion that the compounds inhibit the effects of VEGF. European Patent Publication No. 0326330 discloses certain quinoline, quinazoline and cinnoline plant fungicides. Certain of these plant fungicides are also stated to possess insecticidal and miticidal activity. There is however no disclosure or any suggestion that any of the compounds disclosed may be used for any purpose in animals such as humans. In particular, the European Patent Publication contains no teaching whatsoever concerning angiogenesis and/or increased vascular permeability mediated by growth factors such as VEGF.

The present invention is based on the discovery of compounds that surprisingly inhibit the effects of VEGF, a property of value in the treatment of disease states associated with angiogenesis and/or increased vascular permeability such as cancer, diabetes, psoriasis. rheumatoid arthritis, Kaposi's sarcoma, haemangioma, acute and chronic nephropathies, atheroma, arterial restenosis, autoimmune diseases, acute inflammation and ocular diseases with retinal vessel proliferation. Compounds of the present invention possess higher potency against VEGF receptor tyrosine kinase whilst possessing some activity against EGF receptor tyrosine kinase. Furthermore, compounds of the present invention, possess substantially higher potency against VEGF receptor tyrosine kinase than against EGF receptor tyrosine kinase or FGF R1 receptor tyrosine kinase. Thus compounds of the invention which have been tested possess activity against VEGF receptor tyrosine kinase such that they may be used in an amount sufficient to inhibit VEGF receptor tyrosine kinase whilst demonstrating no significant activity against EGF receptor tyrosine kinase or FGF R1 receptor tyrosine kinase.

According to one aspect of the present invention there is provided a quinazoline derivative of the formula I:

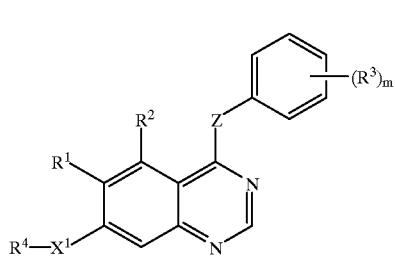

(I)

[wherein:

Z represents —O—, —NH— or —S—;

m is an integer from 1 to 5 with the proviso that where Z is —NH— m is an integer from 3 to 5;

$R^1$ represents hydrogen, hydroxy, halogeno, nitro, trifluoromethyl, cyano, $C_{1-3}$alkyl, $C_{1-3}$alkoxy, $C_{1-3}$alkylthio, or —$NR^5R^6$ (wherein $R^5$ and $R^6$, which may be the same or different, each represents hydrogen or $C_{1-3}$alkyl);

$R^2$ represents hydrogen, hydroxy, halogeno, methoxy, amino or nitro;

$R^3$ represents hydroxy, halogeno, $C_{1-3}$alkyl, $C_{1-3}$alkoxy, $C_{1-3}$alkanoyloxy, trifluoromethyl, cyano, amino or nitro;

$X^1$ represents —O—, —$CH_2$—, —S—, —SO—, —$SO_2$—, —$NR^7$—, —$NR^8CO$—, —$CONR^9$-, —$SO_2NR^{10}$— or —$NR^{11}SO_2$—, (wherein $R^7$, $R^8$, $R^9$, $R^{10}$ and $R^{11}$ each represents hydrogen, $C_{1-3}$alkyl or $C_{1-3}$alkoxy$C_{2-3}$alkyl);

$R^4$ is selected from one of the following seven groups:
1) hydrogen, $C_{1-5}$alkyl, $C_{1-5}$hydroxyalkyl, (preferably $C_{2-3}$hydroxyalkyl), $C_{1-5}$fluoroalkyl, $C_{1-5}$aminoalkyl;
2) $C_{1-5}$alkyl$X^2COR^{12}$ (wherein $X^2$ represents —O— or —NR$^{13}$— (in which R$^{13}$ represents hydrogen, $C_{1-3}$alkyl or $C_{1-3}$alkoxy$C_{2-3}$alkyl) and $R^{12}$ represents $C_{1-3}$alkyl, —NR$^{14}$R$^{15}$ or —OR$^{16}$ (wherein R$^{14}$, R$^{15}$ and R$^{16}$ which may be the same or different each represents hydrogen, $C_{1-3}$alkyl or $C_{1-3}$alkoxy$C_{2-3}$alkyl));
3) $C_{1-5}$alkyl$X^3R^{17}$ (wherein $X^3$ represents —O—, —S—, —SO—, —SO$_2$—, —OCO—, —NR$^{18}$CO—, —CONR$^{19}$—, —SO$_2$NR$^{20}$—, —NR$^{21}$SO$_2$— or —NR$^{22}$— (wherein R$^{18}$, R$^{19}$, R$^{20}$, R$^{21}$ and R$^{22}$ each independently represents hydrogen, $C_{1-3}$alkyl or $C_{1-3}$alkoxy$C_{2-3}$alkyl) and R$^{17}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{1-5}$alkyl$R^{23}$ (wherein R$^{23}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);
5) $C_{2-5}$alkenyl$R^{23}$ (wherein R$^{23}$ is as defined hereinbefore);
6) $C_{2-5}$alkynyl$R^{23}$ (wherein R$^{23}$ is as defined hereinbefore); and
7) $C_{1-5}$alkyl$X^4C_{1-5}$alkyl$X^5R^{24}$ (wherein $X^4$ and $X^5$ which may be the same or different are each —O—, —S—, —SO—, —SO$_2$—, —NR$^{25}$CO—, —CONR$^{26}$—, —SO$_2$NR$^{27}$—, —NR$^{28}$SO$_2$— or —NR$^{29}$— (wherein R$^{25}$, R$^{26}$ R$^{27}$, R$^{28}$ and R$^{29}$ each independently represents hydrogen, $C_{1-3}$alkyl or $C_{1-3}$alkoxy$C_{2-3}$alkyl) and R$^{24}$ represents hydrogen or $C_{1-3}$alkyl)]; and salts thereof.

Z is advantageously —S—, preferably —O—, but especially —NH—.

Where Z is —S— or —O— m is advantageously an integer from 2 to 5, preferably 2 or 3.

Where Z is —NH— m is preferably 3.

$R^1$ is advantageously hydrogen, hydroxy, cyano, nitro, trifluoromethyl, $C_{1-3}$ alkyl, $C_{1-3}$ alkoxy or amino.

$R^1$ is preferably hydrogen, hydroxy, cyano, nitro, trifluoromethyl, methyl, ethyl, methoxy, or ethoxy, more preferably hydrogen, cyano, nitro, trifluoromethyl, hydroxy, methyl or methoxy,, but especially methoxy.

Where $X^1$ is —NR$^8$CO—, $R^1$ is preferably hydrogen.

$R^2$ is preferably hydrogen, fluoro, amino or nitro, but especially hydrogen.

In one embodiment of the present invention $R^3$ represents hydroxy, halogeno, $C_{1-3}$alkyl, $C_{1-3}$alkoxy, trifluoromethyl, cyano, amino or nitro, preferably hydroxy, halogeno or $C_{1-2}$ alkyl, especially hydroxy or halogeno.

Advantageously in another embodiment of the present invention one $R^3$ substituent is advantageously hydroxy, preferably meta-hydroxy, and the other one or more are each selected from halogeno, methyl and methoxy.

In another embodiment of the invention the phenyl group bearing $(R^3)_m$ is preferably of the formula II:

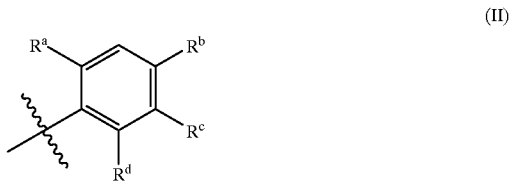

(II)

wherein:
$R^a$ represents hydrogen, methyl, fluoro or chloro, preferably hydrogen, fluoro or chloro, especially fluoro;
$R^b$ represents hydrogen, methyl, methoxy, bromo, fluoro or chloro;
$R^c$ represents hydrogen or hydroxy, especially hydroxy;
$R^d$ represents hydrogen, fluoro or chloro, especially hydrogen or fluoro.

Preferably in another embodiment of the invention two $R^3$ substituents are halogeno, especially ortho,ortho'-difluoro, and the other one or more are each selected from halogeno, hydroxy and methyl, especially from halogeno and methyl.

In a particular aspect of the present invention, the phenyl group bearing $(R^3)_m$ is the 2-fluoro-5-hydroxy-4-methylphenyl group, the 4-bromo-2,6-difluorophenyl group, the 4-chloro-2-fluoro-5-hydroxyphenyl group, the 4-chloro-2,6-difluorophenyl group or the 2,4-difluoro-5-hydroxyphenyl group or, where Z is O or S, the 4-chloro-2-fluorophenyl group.

Preferably the phenyl group bearing $(R^3)_m$ is the 4-chloro-2-fluoro-5-hydroxyphenyl group or the 2-fluoro-5-hydroxy-4-methylphenyl group or, where Z is O or S, the 4-chloro-2 -fluorophenyl group. The 4-chloro-2-fluoro-5-hydroxyphenyl group is an especially preferred value for the phenyl group bearing $(R^3)_m$.

Conveniently $X^1$ represents —O—, —S—, —CH$_2$—, —NR$^8$CO—, —CONR$^9$—, —NR$^{11}$SO$_2$— or —NR$^7$— (wherein R$^7$, R$^8$, R$^9$ and R$^{11}$ each independently represents hydrogen, $C_{1-3}$alkyl (especially $C_{1-2}$alkyl) or $C_{1-2}$alkoxyethyl).

Advantageously $X^1$ represents —O—, —S—, —NR$^8$CO—, —NR$^{11}$SO$_2$— or —NR$^7$— (wherein R$^7$, R$^8$ and R$^{11}$ each independently represents hydrogen, $C_{1-2}$alkyl or $C_{1-2}$alkoxyethyl).

Preferably $X^1$ represents —O—, —S—, —NR$^8$CO—, —NR$^{11}$SO$_2$— (wherein R$^8$ and R$^{11}$ each independently represents hydrogen or $C_{1-2}$alkyl) or NH.

More preferably $X^1$ represents —O—, —S—, —NR$^8$CO— (wherein R$^8$ represents hydrogen or methyl) or NH.

Particularly $X^1$ represents —O— or —NHCO—, especially —O—.

Advantageously $X^2$ represents —O— or —NR$^{13}$— (wherein R$^{13}$ represents hydrogen, $C_{1-3}$alkyl or $C_{1-2}$alkoxyethyl).

Advantageously $X^3$ represents —O—, —S—, —SO—, —SO$_2$—, —NR$^{18}$CO—, —NR$^{21}$SO$_2$— or —NR$^{22}$—

(wherein $R^{18}$, $R^{21}$ and $R^{22}$ each independently represents hydrogen, $C_{1-2}$alkyl or $C_{1-2}$alkoxyethyl).

Preferably $X^3$ represents —O—, —S—, —SO—, —SO$_2$— or —NR$^{22}$— (wherein $R^{22}$ represents hydrogen, $C_{1-2}$alkyl or $C_{1-2}$alkoxyethyl).

More preferably $X^3$ represents —O— or —NR$^{22}$— (wherein $R^{22}$ represents hydrogen or $C_{1-2}$alkyl).

Advantageously $X^4$ and $X^5$ which may be the same or different each represents —O—, —S—, —SO—, —SO$_2$— or —NR$^{29}$— (wherein $R^{29}$ represents hydrogen, $C_{1-3}$alkyl or $C$,-$_2$alkoxyethyl).

Preferably $X^4$ and $X^5$ which may be the same or different each represents —O—, —S— or —NR$^{29}$— (wherein $R^{29}$ represents hydrogen, $C_{1-2}$alkyl or $C_{1-2}$alkoxyethyl).

More preferably $X^4$ and $X^5$ which may be the same or different each represents —O— or —NH—.

Conveniently $R^4$ is selected from one of the following nine groups:
1) $C_{1-5}$alkyl, $C_{2-5}$hydroxyalkyl, $C_{1-5}$fluoroalkyl, $C_{1-5}$aminoalkyl;
2) $C_{1-5}$alkyl$X^2$COR$^{12}$ (wherein $X^2$ is as hereinbefore defined and $R^{12}$ represents $C_{1-3}$alkyl, —NR$^{14}$R$^{15}$ or —OR$^{16}$ (wherein $R^{14}$, $R^{15}$ and $R^{16}$ which may be the same or different each represents hydrogen, $C_{1-3}$alkyl or $C_{1-3}$alkoxyC$_{2-3}$alkyl));
3) $C_{1-5}$alkyl$X^3$R$^{17}$ (wherein $X^3$ is as hereinbefore defined and $R^{17}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-3}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{1-5}$alkylR$^{30}$ (wherein $R^{30}$ is a 5 or 6 membered saturated heterocyclic group with one or two heteroatoms, selected independently from O, S and N, which heterocyclic group is linked to $C_{1-5}$alkyl through a carbon atom and which heterocyclic group may bear one or two substituents selected from oxo, hydroxy, halogeno, $C_{1-4}$alkyl, $C_{1-4}$hydroxyalkyl and $C_{1-4}$alkoxy) or $C_{2-5}$alkylR$^{31}$ (wherein $R^{31}$ is a 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-4}$alkyl, $C_{1-4}$hydroxyalkyl and $C_{1-4}$alkoxy);
5) $C_{3-4}$alkenylR$^{30}$ (wherein $R^{30}$ is as defined hereinbefore);
6) $C_{3-4}$alkynylR$^{30}$ (wherein $R^{30}$ is as defined hereinbefore);
7) $C_{3-4}$alkenylR$^{31}$ (wherein $R^{31}$ is as defined hereinbefore);
8) $C_{3-4}$alkynylR$^{31}$ (wherein $R^{31}$ is as defined hereinbefore); and
9) $C_{1-5}$alkyl$X^4$C$_{1-5}$alkyl$X^5$R$^{24}$ (wherein $X^4$ and $X^5$ are as hereinbefore defined and $R^{24}$ represents hydrogen or $C_{1-3}$alkyl).

Advantageously $R^4$ is selected from one of the following nine groups:
1) $C_{1-5}$alkyl, $C_{2-5}$hydroxyalkyl, $C_{1-5}$fluoroalkyl, $C_{2-4}$aminoalkyl;
2) $C_{2-5}$alkyl$X^2$COR$^{12}$ (wherein $X^2$ is as hereinbefore defined and $R^{12}$ represents $C_{1-3}$alkyl, —NR$^{14}$R$^{15}$ or —OR$^{16}$ (wherein $R^{14}$, $R^{15}$ and $R^{16}$ which may be the same or different are each $C_{1-2}$alkyl or $C_{1-2}$alkoxyethyl));
3) $C_{2-4}$alkyl$X^3$R$^{17}$ (wherein $X^3$ is as hereinbefore defined and $R^{17}$ is a group selected from $C_{1-3}$alkyl, cyclopentyl, cyclohexyl, pyrrolidinyl and piperidinyl which group is linked to $X^3$ through a carbon atom and which $C_{1-3}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl $C_{1-2}$hydroxyalkyl and $C_{1-2}$alkoxy);
4) $C_{1-4}$alkylR$^{30}$ (wherein $R^{30}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry one or two substituents selected from oxo, hydroxy, halogeno, $C_{1-2}$alkyl, $C_{1-2}$hydroxyalkyl and $C_{1-2}$alkoxy) or $C_{2-4}$alkylR$^{31}$ (wherein $R^{31}$ is a group selected from morpholino, thiomorpholino, pyrrolidin-1-yl, piperazin-1-yl and piperidino which group may carry one or two substituents selected from oxo, hydroxy, halogeno, $C_{1-2}$alkyl, $C_{1-2}$hydroxyalkyl and $C_{1-2}$alkoxy);
5) $C_{3-4}$alkenylR$^{30}$ (wherein $R^{30}$ is as defined hereinbefore);
6) $C_{3-4}$alkynylR$^{30}$ (wherein $R^{30}$ is as defined hereinbefore);
7) $C_{3-4}$alkenylR$^{31}$ (wherein $R^{31}$ is as defined hereinbefore);
8) $C_{3-4}$alkynylR$^{31}$ (wherein $R^{31}$ is as defined hereinbefore); and
9) $C_{2-3}$alkyl$X^4$C$_{2-3}$alkyl$X^5$R$^{24}$ (wherein $X^4$ and $X^5$ are as hereinbefore defined and $R^{24}$ represents hydrogen or $C_{1-3}$alkyl).

Preferably $R^4$ is selected from one of the following five groups:
1) $C_{1-3}$alkyl, $C_{2-3}$hydroxyalkyl, $C_{1-3}$fluoroalkyl, $C_{2-3}$aminoalkyl;
2) 2-(3,3-dimethylureido)ethyl, 3-(3,3-dimethylureido)propyl, 2-(3-methylureido)ethyl, 3-(3-methylureido)propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-N-methylcarbamoyloxy)propyl, 2-(carbamoyloxy)ethyl, 3-(carbamoyloxy)propyl;
3) $C_{2-3}$alkyl$X^3$R$^{17}$ (wherein $X^3$ is as hereinbefore defined and $R^{17}$ is a group selected from $C_{1-2}$alkyl, cyclopentyl, cyclohexyl, pyrrolidinyl and piperidinyl which group is linked to $X^3$ through a carbon atom and which $C_{1-2}$alkyl group may bear one or two substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);
4) $C_{1-2}$alkylR$^{30}$ (wherein $R^{30}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkylR$^{31}$ (wherein R$^{31}$ is a group selected from morpholino, thiomorpholino, piperidino, piperazin-1-yl and pyrrolidin-1-yl which group may carry one substituent selected from oxo, hydroxy, halogeno, $C_{1-2}$alkyl, $C_{1-2}$hydroxyalkyl and $C_{1-2}$alkoxy); and 5) $C_{2-3}$alkylX$^4$C$_{2-3}$alkylX$^5$R$^{24}$ (wherein X$^4$ and X$^5$ are as hereinbefore defined and R$^{24}$ represents hydrogen or $C_{1-2}$alkyl).

More preferably R$^4$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-thiomorpholinoethyl, 3-thiomorpholinopropyl, 2-(4-methylpiperazin-1-yl)ethyl, 3-(4-methylpiperazin-1-yl)propyl or 2-(2-methoxyethoxy)ethyl.

Particularly R$^4$ represents 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-thiomorpholinoethyl, 3-thiomorpholinopropyl, 2-(4-methylpiperazin-1-yl)ethyl, 3-(4-methylpiperazin-1-yl)propyl or 2-(2-methoxyethoxy)ethyl.

Preferred compounds are:
4-(4-bromo-2,6-difluoroanilino)-6,7-dimethoxyquinazoline,
4-(4-bromo-2-fluoro-5-hydroxyanilino)-6,7-dimethoxyquinazoline,
4-(4-chloro-2-fluoro-5-hydroxyanilino)-6-methoxy-7-(2-thiomorpholinoethoxy)quinazoline,
6,7-dimethoxy-4-(3-hydroxy-4-methylphenoxy)quinazoline,
4-(4-chloro-2-fluoro-5-hydroxyanilino)-6-methoxy-7-(3-morpholinopropoxy)quinazoline,
4-(2-fluoro-5-hydroxy-4-methylanilino)-7-(2-hydroxyethoxy)-6-methoxyquinazoline,
4-(4-chloro-2-fluoro-5-hydroxyanilino)-6-methoxy-7-(2-(4-methylpiperazi-1-yl)ethoxy)quinazoline,
4-(2-fluoro-5-hydroxy-4-methylanilino)-7-(2-methoxyethoxy)quinazoline,
4-(2-fluoro-5-hydroxy-4-methylanilino)-6-methoxy-7-(2-(methylsulphinyl)ethoxy)quinazoline,
4-(4-chloro-2-fluoro-5-hydroxyanilino)-6-methoxy-7-(2-methoxyethoxy)quinazoline,
4-(4-chloro-2-fluoro-5-hydroxyanilino)-6,7-dimethoxyquinazoline,
4-(2-fluoro-5-hydroxy-4-methylanilino)-6,7-dimethoxyquinazoline,
4-(2-fluoro-5-hydroxy-4-methylanilino)-6-methoxy-7-(2-methoxyethoxy)quinazoline,
7-(2-acetoxyethoxy)-4-(2-fluoro-5-hydroxy-4-methylanilino)-6-methoxyquinazoline,
4-(4-chloro-2-fluoro-5-hydroxyanilino)-6-methoxy-7-(2-morpholinoethoxy)quinazoline,
4-(4-chloro-2-fluoro-5-hydroxyanilino)-6-methoxy-7-(2-piperidinoethoxy)quinazolne,
4-(4-chloro-2-fluoro-5-hydroxyanilino)-6-methoxy-7-(2-(pyrrolidin-1-yl)ethoxy)quinazoline,
4-(2-fluoro-5-hydroxy-4-methylanilino)-7-(2-methoxyethylamino)quinazoline,
4-(4-chloro-2-fluoro-5-hydroxyanilino)-6-methoxy-7-(2-cyclopentyloxyethoxy)quinazoline,
4-(2-fluoro-5-hydroxy-4-methylanilino)-6-methoxy-7-(2-methylthioethoxy)quinazoline,
4-(2,4-difluoro-5-hydroxyanilino)-6,7-dimethoxyquinazoline,
4-(2-fluoro-5-hydroxy-4-methylanilino)-6-methoxy-7-(3-morpholinopropoxy)quinazoline,
4-(2-fluoro-5-hydroxy-4-methylanilino)-7-methoxyacetamidoquinazoline,
4-(4-bromo-2,6-difluoroanilino)-6-methoxy-7-(3-morpholinopropoxy)quinazoline
and salts thereof especially the hydrochloride salts thereof.

More preferred compounds are:
4-(4-bromo-2-fluoro-5-hydroxyanilino)-6,7-dimethoxyquinazoline,
4-(4-chloro-2-fluoro-5-hydroxyanilino)-6-methoxy-7-(2-thiomorpholinoethoxy)quinazoline,
6,7-dimethoxy-4-(3-hydroxy-4-methylphenoxy)quinazoline,
4-(4-chloro-2-fluoro-5-hydroxyanilino)-6-methoxy-7-(3-morpholinopropoxy)quinazoline,
4-(2-fluoro-5-hydroxy-4-methylanilino)-7-(2-hydroxyethoxy)-6-methoxyquinazoline,
4-(4-chloro-2-fluoro-5-hydroxyanilino)-6-methoxy-7-(2-(4-methylpiperazin-1-yl)ethoxy)quinazoline,
4-(2-fluoro-5-hydroxy-4-methylanilino)-7-(2-methoxyethoxy)quinazoline,
4-(2-fluoro-5-hydroxy-4-methylanilino)-6-methoxy-7-(2-(methylsulphinyl)ethoxy)quinazoline,
4-(4-chloro-2-fluoro-5-hydroxyanilino)-6-methoxy-7-(2-methoxyethoxy)quinazoline,
4-(4-chloro-2-fluoro-5-hydroxyanilino)-6,7-dimethoxyquinazoline,
4-(2-fluoro-5-hydroxy-4-methylanilino)-6,7-dimethoxyquinazoline,
4-(2-fluoro-5-hydroxy-4-methylanilino)-6-methoxy-7-(2-methoxyethoxy)quinazoline,
7-(2-acetoxyethoxy)-4-(2-fluoro-5-hydroxy-4-methylanilino)-6-methoxyquinazoline,
4-(4-chloro-2-fluoro-5-hydroxyanilino)-6-methoxy-7-(2-morpholinoethoxy)quinazoline,
4-(4-chloro-2-fluoro-5-hydroxyanilino)-6-methoxy-7-(2-piperidinoethoxy)quinazoline,
4-(4-chloro-2-fluoro-5-hydroxyanilino)-6-methoxy-7-(2-(pyrrolidin-1-yl)ethoxy)quinazoline, 4-(2-fluoro-5-hydroxy-4-methylanilino)-7-(2-methoxyethylamino)quinazoline;
4-(4-chloro-2-fluoro-5-hydroxyanilino)-6-methoxy-7-(2-cyclopentyloxyethoxy)quinazoline,
4-(2-fluoro-5-hydroxy-4-methylanilino)-6-methoxy-7-(2-methylthioethoxy)quinazoline,
4-(2,4-difluoro-5-hydroxyanilino)-6,7-dimethoxyquinazoline,
4-(2,4-difluoro-5-hydroxyanilino)-6-methoxy-7-(2-methoxyethoxy)quinazoline,
4-(2-fluoro-5-hydroxy-4-methylanilino)-6-methoxy-7-(3-morpholinopropoxy)quinazoline,
4-(2-fluoro-5-hydroxy-4-methylanilino)-7-methoxyacetamidoquinazoline,
4-(4-bromo-2,6-difluoroanilino)-6-methoxy-7-(3-morpholinopropoxy)quinazoline and salts thereof especially the hydrochloride salts thereof.

Particularly preferred compounds are:
4-(4-chloro-2-fluoro-5-hydroxyanilino)-6-methoxy-7-(2-methoxyethoxy)quinazoline,
4-(4-chloro-2-fluoro-5-hydroxyanilino)-6,7-dimethoxyquinazoline,
4-(2-fluoro-5-hydroxy-4-methylanilino)-6,7-dimethoxyquinazoline,
4-(2-fluoro-5-hydroxy-4-methylanilino)-6-methoxy-7-(2-methoxyethoxy)quinazoline,
7-(2-acetoxyethoxy)-4-(2-fluoro-5-hydroxy-4-methylanilino)-6-methoxyquinazoline,
4-(4-chloro-2-fluoro-5-hydroxyanilino)-6-methoxy-7-(2-morpholinoethoxy)quinazoline,
4-(4-chloro-2-fluoro-5-hydroxyanilino)-6-methoxy-7-(2-piperidinoethoxy)quinazoline,
4-(4-chloro-2-fluoro-5-hydroxyanilino)-6-methoxy-7-(2-(pyrrolidin-1-yl)ethoxy)quinazoline,
4-(2-fluoro-5-hydroxy-4-methylanilino)-7-(2-methoxyethylamino)quinazoline,
4-(4-chloro-2-fluoro-5-hydroxyanilino)-6-methoxy-7-(2-cyclopentyloxyethoxy)quinazoline,
4-(2-fluoro-5-hydroxy-4-methylanilino)-6-methoxy-7-(2-methylthioethoxy)quinazoline,
4-(2,.4-difluoro-5-hydroxyanilino)-6,7-dimethoxyquinazoline,
4-(2-fluoro-5-hydroxy-4-methylanilino)-6-methoxy-7-(3-morpholinopropoxy)quinazoline,
4-(2-fluoro-5-hydroxy-4-methylanilino)-7-methoxyacetamidoquinazoline,
4-(4-bromo-2,6-difluoroanilino)-6-methoxy-7-(3-morpholinopropoxy)quinazoline and salts thereof especially the hydrochloride salts thereof.

More particularly preferred compounds are:
4-(4-chloro-2-fluoro-5-hydroxyanilino)-6-methoxy-7-(2-(pyrrolidin-1-yl)ethoxy)quinazoline,
4-(2-fluoro-5-hydroxy-4-methylanilino)-6-methoxy-7-(2-methylthioethoxy)quinazoline,
4-(4-chloro-2-fluoro-5-hydroxyanilino)-6,7-dimethoxyquinazoline,
4-(2-fluoro-5-hydroxy-4-methylanilino)-6,7-dimethoxyquinazoline,
4-(2-fluoro-5-hydroxy-4-methylanilino)-6-methoxy-7-(2-methoxyethoxy)quinazoline,
4-(2-fluoro-5-hydroxy-4-methylanilino)-6-methoxy-7-(3-morpholinopropoxy)quinazoline,
4-(2-fluoro-5-hydroxy-4-methylanilino)-7-methoxyacetamidoquinazoline,
4-(4-bromo-2,6-difluoroanilino)-6-methoxy-7-(3-morpholinopropoxy)quinazoline and salts thereof especially the hydrochloride salts thereof.

Especially preferred compounds are:
4-(2-fluoro-5-hydroxy-4-methylanilino)-6,7-dimethoxyquinazoline,
4-(2-fluoro-5-hydroxy-4-methylanilino)-6-methoxy-7-(2-methoxyethoxy)quinazoline,
4-(2-fluoro-5-hydroxy-4-methylanilino)-7-methoxyacetamidoquinazoline,
4-(4-bromo-2,6-difluoroanilino)-6-methoxy-7-(3-morpholinopropoxy)quinazoline and salts thereof especially the hydrochloride salts thereof.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–6 carbon atoms, preferably 1–4 carbon atoms. In this specification the term "alkoxy" means an alkyl group as defined hereinbefore linked to an oxygen atom. In this specification the term "aryl" includes $C_{6-10}$ aromatic groups which may, if desired, carry one or more substituents selected from halogeno, alkyl, alkoxy, cyano, nitro or trifluoromethyl (wherein alkyl and alkoxy are as hereinbefore defined). The term "aryloxy" means an aryl group as defined hereinbefore linked to an oxygen atom. In this specification the term "sulphonyloxy" includes alkylsulphonyloxy and arylsulphonyloxy wherein "alkyl" and "aryl" are as defined hereinbefore. The term "alkanoyl" as used herein unless otherwise stated includes alkylC=O groups in which "alkyl" is as defined hereinbefore, for example ethanoyl refers to $CH_3C=O$. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2–5 carbon atoms, preferably 3–4 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2–5 carbon atoms, preferably 3–4 carbon atoms.

In formula I, as hereinbefore defined, hydrogen will be present at positions 2 and 8 of the quinazoline group.

Within the present invention it is to be understood that a quinazoline of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings.

It is also to be understood that certain quinazolines of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that when $X^1$ is, for example, a group of formula —$NR^8CO$—, it is the nitrogen atom bearing the $R^8$ group which is attached to the quinazoline ring and the carbonyl (CO) group is attached to $R^4$, whereas when $X^1$ is, for example, a group of formula —$CONR^9$—, it is the carbonyl group which is attached to the quinazoline ring and the nitrogen atom bearing the $R^9$ group is attached to $R^4$. A similar convention applies to the other two atom $X^1$ linking groups, such as —$NR^{11}SO_2$— and —$SO_2NR^{10}$—. When $X^1$ is —$NR^7$— it is the nitrogen atom bearing the $R^7$ group which is linked to the quinazoline ring and to $R^4$. An analogous convention applies to other groups. It is further to be understood that when $X^1$ represents —$NR^7$— and $R^7$ is $C_{1-3}$alkoxy$C_{2-3}$alkyl it is the $C_{2-3}$alkyl moiety which is linked to the nitrogen atom of $X^1$ and an analogous convention applies to other groups.

For the avoidance of any doubt, it is to be understood that in a compound of the formula I when $R^4$ is, for example, a group of formula $C_{1-5}$alkyl$R^{23}$, it is the terminal $C_{1-5}$alkyl moiety which is bound to $X^1$, similarly when $R^4$ is, for example, a group of formula $C_{2-5}$alkenyl$R^{23}$ it is the $C_{2-5}$alkenyl moiety which is bound to $X^1$ and an analogous convention applies to other groups. When $R^4$ is a group 1-$R^{23}$prop-1-en-3-yl it is the first carbon to which the group $R^{23}$ is attached and it is the third carbon which is linked to $X^1$ and an analogous convention applies to other groups.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as hereinafter defined) may be prepared by any process known to be applicable to the preparation of chemically-related compounds. Such processes include, for example, those illustrated in European Patent Applications, Publication Nos. 0520722, 0566226, 0602851 and 0635498. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus the following processes (a) to (g) and (i) to (v) constitute further features of the present invention.
Synthesis of Compounds of Formula I (a) Compounds of the formula I and salts thereof may be prepared by the reaction of a compound of the formula III:

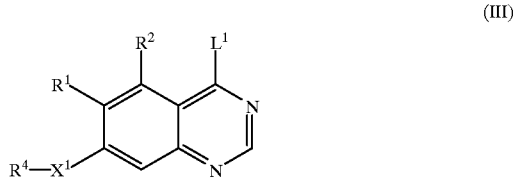

(III)

(wherein $R^1$, $R^2$, $X^1$ and $R^4$ are as defined hereinbefore and $L^1$ is a displaceable moiety), with a compound of the formula IV:

(IV)

(wherein Z, $R^3$ and m are as defined hereinbefore) whereby to obtain compounds of the formula I and salts thereof. A convenient displaceable moiety $L^1$ is, for example, a halogeno, alkoxy (preferably $C_{1-4}$alkoxy), aryloxy or sulphonyloxy group, for example a chloro, bromo, methoxy, phenoxy, methanesulphonyloxy or toluene-4-sulphonyloxy group.

The reaction is advantageously effected in the presence of either an acid or a base. Such an acid is, for example, an anhydrous inorganic acid such as hydrogen chloride. Such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or for example, an alkali metal or alkaline earth metal carbonate or hydroxide, for example sodium carbonate, potassium carbonate, calcium carbonate, sodium hydroxide or potassium hydroxide. Alternatively such a base, is, for example, an alkali metal hydride, for example sodium hydride, or an alkali metal or alkaline earth metal amide, for example sodium amide or sodium bis(trimethylsilyl)amide. The reaction is preferably effected in the presence of an inert solvent or diluent, for example an alkanol or ester such as methanol, ethanol, isopropanol or ethyl acetate, a halogenated solvent such as methylene chloride, trichloromethane or carbon tetrachloride, an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethylsulphoxide. The reaction is conveniently effected at a temperature in the range, for example, 10 to 1 50° C., preferably in the range 20 to 80° C.

The compound of the invention may be obtained from this process in the form of the free base or alternatively it may be obtained in the form of a salt with the acid of the formula H—$L^1$ wherein $L^1$ has the meaning defined hereinbefore. When it is desired to obtain the free base from the salt, the salt may be treated with a base as defined hereinbefore using a conventional procedure.

(b) Where the group of formula IIa:

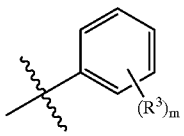

(IIa)

(wherein $R^3$ and m are as hereinbefore defined) represents a phenyl group carrying one or more hydroxy groups, a compound of the formula I and salts thereof can be prepared by the deprotection of a compound of formula V:

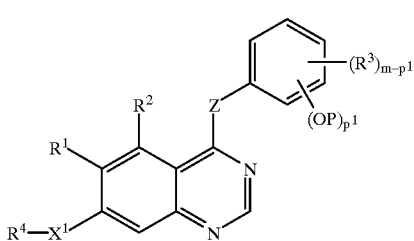

(V)

(wherein $X^1$, m, $R^1$, $R^2$, $R^3$, $R^4$ and Z are as hereinbefore defined, P represents a phenolic hydroxy protecting group and $p^1$ is an integer from 1 to 5 equal to the number of protected hydroxy groups and such that m—$p^1$ is equal to the number of $R^3$ substituents which are not protected hydroxy). The choice of phenolic hydroxy protecting group P is within the standard knowledge of an organic chemist, for example those included in standard texts such as "Protective Groups in Organic Synthesis" T. W. Greene and R. G. M. Wuts, 2nd Ed. Wiley 1991, including ethers (for example, methyl, methoxymethyl, allyl and benzyl), silyl ethers (for example, t-butyldiphenylsilyl and t-butyldimethylsilyl), esters (for example, acetate and benzoate) and carbonates (for example, methyl and benzyl). The removal of such a phenolic hydroxy protecting group may be effected by any of the procedures known for such a transformation, including those reaction conditions indicated in standard texts such as that indicated hereinbefore, or by a related procedure. The reaction conditions preferably being such that the hydroxy derivative is produced without unwanted reactions at other sites within the starting or product compounds. For example, where the protecting group P is acetate, the transformation may conveniently be effected by treatment of the quinazoline derivative with a base as defined hereinbefore and including ammonia, and its mono and di-alkylated derivatives, preferably in the presence of a protic solvent or co-solvent such as water or an alcohol for example methanol or ethanol. Such a reaction can be effected in the presence of an additional inert solvent or diluent as defined hereinbefore and at a temperature in the range 0 to 50° C. conveniently about 20° C.

(c) Production of those compounds of formula I and salts thereof wherein the substituent $X^1$ is —O—, —S— or —$NR^7$— can be achieved by the reaction, conveniently in the presence of a base as defined hereinbefore, of a compound of the formula VI:

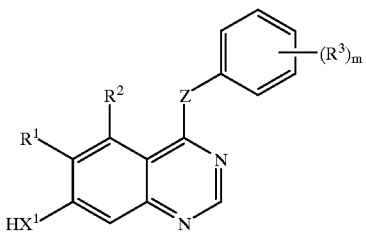

(VI)

(wherein m, $X^1$, $R^1$, $R^2$, $R^3$, and Z are as hereinbefore defined) with a compound of formula VII:

$R^4$—$L^1$ (VII)

(wherein $R^4$ and $L^1$ are as hereinbefore defined); $R^1$ is a displaceable moiety for ex ample a halogeno or sulphonyloxy group such as a bromo or methanesulphonyloxy group. The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(d) Compounds of the formula I and salts thereof may be prepared by the reaction of a compound of the formula VIII:

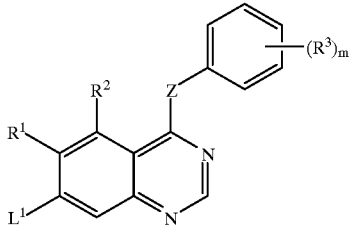

(VIII)

with a compound of the formula IX:

$R^4$—$X^1$—H (IX)

(wherein $L^1$, $R^1$, $R^2$, $R^3$, $R^4$, Z, m and $X^1$ are all as hereinbefore defined). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

(e) Compounds of the formula I and salts thereof wherein $R^4$ is $C_{1-5}$alkyl$R^{32}$, [wherein $R^{32}$ is selected from one of the following four groups:

1) $X^6C_{1-3}$alkyl (wherein $X^6$ represents —O—, —S—, —$SO_2$—, —$NR^{33}CO$— or —$NR^{34}SO_2$— (wherein $R^{33}$ and $R^{34}$ are each independently hydrogen, $C_{1-3}$alkyl or $C_{1-3}$alkoxy$C_{2-3}$alkyl);

2) $NR^{35}R^{36}$ (wherein $R^{35}$ and $R^{36}$ which may be the same or different are each hydrogen, $C_{1-3}$alkyl or $C_{1-3}$alkoxy$C_{2-3}$alkyl);

3) $X^7C_{1-5}$alkyl$X^5R^{24}$ (wherein $X^7$ represents —O—, —S—, —$SO_2$—, —$NR^{37}CO$—, —$NR^{38}SO_2$— or —$NR^{39}$— (wherein $R^{37}$, $R^{38}$ and $R^{39}$ are each independently hydrogen, $C_{1-3}$alkyl or $C_{1-3}$alkoxy$C_{2-3}$alkyl) and $X^5$ and $R^{24}$ are as defined hereinbefore); and 4) $R^{31}$ (wherein $R^{31}$ is as defined hereinbefore);]

may be prepared by reacting a compound of the formula X:

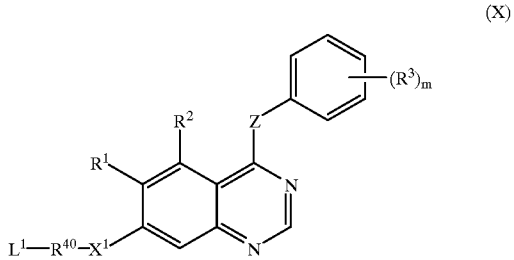

(X)

(wherein $L^1$, $X^1$, $R^1$, $R^2$, $R^3$, Z and m are as hereinbefore defined and $R^{40}$ is $C_{1-5}$alkyl) with a compound of the formula XI:

$R^{32}$—H     (XI)

(wherein $R^{32}$ is as defined hereinbefore) to give a compound of the formula I. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about (f) The production of those compounds of the formula I and salts thereof wherein the substituent $R^1$ is represented by $NR^5R^6$, where one or both of $R^5$ and $R^6$ are $C_{1-3}$alkyl, may be effected by the reaction of compounds of formula I wherein the substituent $R^1$ is an amino group and an alkylating agent, preferably in the presence of a base as defined hereinbefore. Such alkylating agents are $C_{1-3}$alkyl moieties bearing a displaceable moiety as defined hereinbefore such as $C_{1-3}$alkyl halides for example $C_{1-3}$alkyl chloride, bromide or iodide. The reaction is preferably effected in the presence of an inert solvent or diluent (as defined hereinbefore in process (a)) and at a temperature in the range, for example, 10 to 100° C., conveniently at about ambient temperature. This process can also be used for preparing compounds in which $R^4$—$X^1$ is an alkylamino or dialkylamino group.

(g) The production of compounds of formula I and salts thereof wherein one or more of the substituents $R^1$, $R^2$ or $R^3$ is an amino group or where $R^4$—$X^1$ is amino may be effected by the reduction of a corresponding compound of formula I wherein the substituent(s) at the corresponding position(s) of the quinazoline and/or phenyl ring is/are a nitro group(s). The reduction may conveniently be effected as described in process (i) hereinafter. The production of a compound of formula I and salts thereof wherein the substituent(s) at the corresponding position(s) of the quinazoline and/or phenyl ring is/are a nitro group(s) may be effected by the processes described hereinbefore and hereinafter in processes (a–e) and (i–v) using a quinazoline compound selected from the compounds of the formulae (I–XXVII) in which the substituent(s) at the corresponding position(s) of the quinazoline and/or phenyl ring is/are a nitro group(s).

Synthesis of Intermediates (i) The compounds of formula III and salts thereof, constitute a further feature of the present invention. Such compounds in which $L^1$ is halogeno may for example be prepared by halogenating a compound of the formula XII:

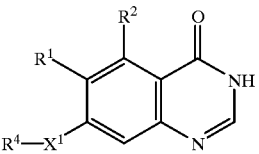

(XII)

(wherein $R^1$, $R^2$, $R^4$ and $X^1$ are as hereinbefore defined).

Convenient halogenating agents include inorganic acid halides, for example thionyl chloride, phosphorus(III) chloride, phosphorus(V)oxychloride and phosphorus(V) chloride. The halogenation reaction is conveniently effected in the presence of an inert solvent or diluent such as for example a halogenated solvent such as methylene chloride, trichloromethane or carbon tetrachloride, or an aromatic hydrocarbon solvent such as benzene or toluene. The reaction is conveniently effected at a temperature in the range, for example 10 to 150° C., preferably in the range 40 to 100° C.

The compounds of formula XII and salts thereof which constitute a further feature of the present invention may for example be prepared by reacting a compound of the formula XIII:

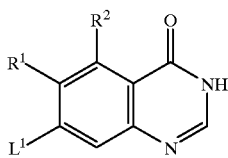

(XIII)

(wherein $R^1$, $R^2$ and $L^1$ are as hereinbefore defined) with a compound of the formula IX as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

The compounds of formula XII and salts thereof may also be prepared by cyclising a compound of the formula XIV:

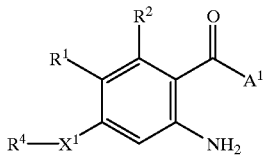

(XIV)

(wherein $R^1$, $R^2$ $R^4$ and $X^1$, are as hereinbefore defined, and $A^1$ is an hydroxy, alkoxy (preferably $C_{1-4}$alkoxy) or amino group) whereby to form a compound of formula XII or salt thereof. The cyclisation may be effected by reacting a compound of the formula XIV, where $A^1$ is an hydroxy or alkoxy group, with formamide or an equivalent thereof effective to cause cyclisation whereby a compound of formula XII or salt thereof is obtained, such as [3-(dimethylamino)-2-azaprop-2-enylidene] dimethylammonium chloride. The cyclisation is conveniently effected in the presence of formamide as solvent or in the presence of an inert solvent or diluent such as an ether for example 1,4-dioxan. The cyclisation is conveniently effected at an elevated temperature, preferably in the range 80 to 200° C. The compounds of formula XII may also be prepared by cyclising a compound of the formula XIV, where $A^1$ is an amino group, with formic acid or an equivalent thereof effective to cause cyclisation whereby a compound of formula XII or salt thereof is obtained. Equivalents of formic acid effective to cause cyclisation include for example a tri-$C_{1-4}$alkoxymethane, for example triethoxymethane and trimethoxymethane. The cyclisation is conveniently effected in the presence of a catalytic amount of an anhydrous acid, such as a sulphonic acid for example p-toluenesulphonic acid, and in the presence of an inert solvent or diluent such as for example a halogenated solvent such as methylene chloride, trichloromethane or carbon tetrachloride, an ether such as diethylether or tetrahydrofuran, or an aromatic hydrocarbon solvent such as toluene. The cyclisation is conveniently effected at a temperature in the range, for example 10 to 100° C., preferably in the range 20 to 50° C.

Compounds of formula XIV and salts thereof, which constitute a further feature of the present invention, may for example be prepared by the reduction of the nitro group in a compound of the formula XV:

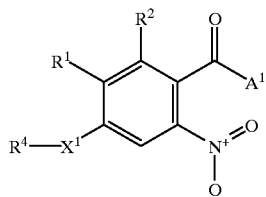

(XV)

(wherein $R^1$, $R^2$, $R^4$, $X^1$ and $A^1$ are as hereinbefore defined) to yield a compound of formula XIV as hereinbefore defined. The reduction of the nitro group may conveniently be effected by any of the procedures known for such a transformation. The reduction may be carried out, for example, by the hydrogenation of a solution of the nitro compound in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound and the activated metal in the presence of a solvent or diluent such as a mixture of water and alcohol, for example methanol or ethanol, to a temperature in the range, for example 50 to 150° C., conveniently at about 70° C.

Compounds of the formula XV and salts thereof which constitute a further feature of the present invention, may for example be prepared by the reaction of a compound of the formula XVI:

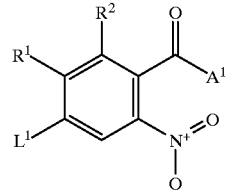

(XVI)

(wherein $R^1$, $R^2$, $L^1$ and $A^1$ are as hereinbefore defined) with a compound of the formula IX as hereinbefore defined to give a compound of the formula XV. The reaction of the compounds of formulae XVI and IX is conveniently effected under conditions as described for process (d) hereinbefore.

Compounds of formula XV and salts thereof, may for example also be prepared by the reaction of a compound of the formula XVII:

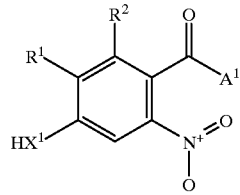

(XVII)

(wherein $R^1$, $R^2$, $X^1$ and $A^1$ are as hereinbefore defined with the proviso that $X^1$ is not —$CH_2$—) with a compound of the formula VII as hereinbefore defined to yield a compound of formula XV as hereinbefore defined. The reaction of the compounds of formulae XVII and VII is conveniently effected under conditions as described for process (c) hereinbefore.

The compounds of formula III and salts thereof may also be prepared for example by reacting a compound of the formula XVIII:

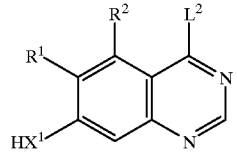

(XVIII)

(wherein $R^1$, $R^2$ and $X^1$ are as hereinbefore defined with the proviso that $X^1$ is not —$CH_2$— and $L^2$ represents a displaceable protecting moiety) with a compound of the formula VII as hereinbefore defined, whereby to obtain a compound of formula III in which $L^1$ is represented by $L^2$.

A compound of formula XVIII is conveniently used in which $L^2$ represents a phenoxy group which may if desired carry up to 5 substituents, preferably up to 2 substituents, selected from halogeno, nitro and cyano. The reaction may be conveniently effected under conditions as described for process (c) hereinbefore.

The compounds of formula XVIII and salts thereof as hereinbefore defined may for example be prepared by deprotecting a compound of the formula XIX:

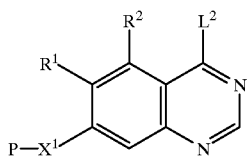

(XIX)

(wherein $R^1$, $R^2$, P, $X^1$ and $L^2$ are as hereinbefore defined with the proviso that $X^1$ is not —$CH_2$—). Deprotection may be effected by techniques well known in the literature, for example where P represents a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XII as hereinbefore defined, followed by introduction of halide to the compound of formula XII, thus obtained as hereinbefore defined, to yield a compound of formula III in which $L^1$ represents halogen.

(ii) The compounds of formula V and salts thereof, constitute a further feature of the present invention, and may for example be prepared by the reaction of a compound of formula III as hereinbefore defined with a compound of the formula XX:

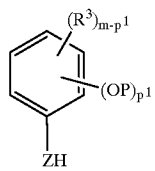

(XX)

(wherein $R^3$, m, $p^1$, P and Z are as hereinbefore defined). The reaction may for example be effected as described for process (a) hereinbefore.

The compounds of formula V and salts thereof may also be prepared by reacting a compound of formula XXI:

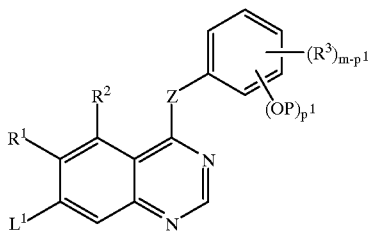

(XXI)

(wherein $R^1$, $R^2$, $L^1$, Z, $R^3$, m, $p^1$ and P are as hereinbefore defined) with a compound of formula IX as hereinbefore defined. The reaction may for example be effected as described for process (d) above.

The compounds of formula V and salts thereof may also be prepared by reacting a compound of formula XXII:

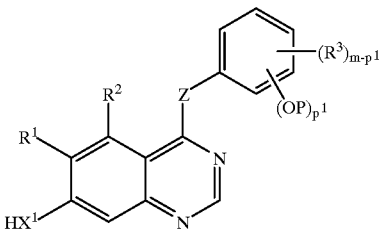

(XXII)

(wherein $R^1$, $R^2$, $R^3$, $X^1$, Z, P, $p^1$ and m are as hereinbefore defined with the proviso that $X^1$ is not —$CH_2$—) with a compound of the formula VII as hereinbefore defined. The reaction may for example be effected as described for process (c) hereinbefore.

The compounds of formula XXI and salts thereof may for example be prepared by reaction of a compound of formula XXIII:

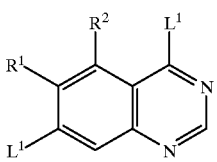

(XXIII)

(wherein $R^1$, $R^2$, and $L^1$ are as hereinbefore defined, and $L^1$ in the 4- and 7-positions may be the same or different) with a compound of the formula XX as hereinbefore defined. The reaction may be effected for example by a process as described in (a) above.

Compounds of the formula XXII and salts thereof may be made by reacting compounds of the formulae XIX and XX as hereinbefore defined, under conditions described in (a) hereinbefore, to give a compound of formula XXIV:

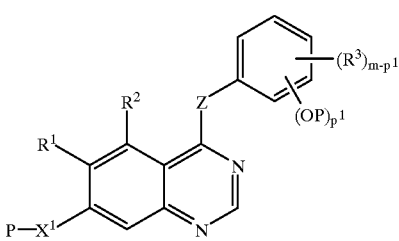

(XXIV)

(wherein $R^1$, $R^2$, $R^3$, P, Z, $X^1$, $p^1$ and m are as hereinbefore defined with the proviso that $X^1$ is not —$CH_2$—) and then deprotecting the compound of formula XXIV for example as described in (i) above.

(iii) Compounds of the formula VI as hereinbefore defined and salts thereof may be made by deprotecting the compound of formula XXV:

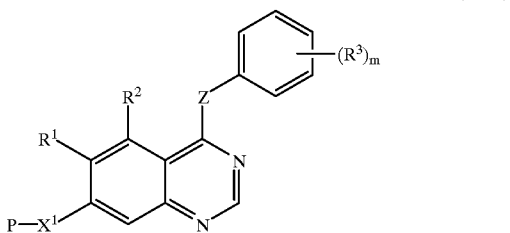

(XXV)

(wherein $R^1$, $R^2$, $R^3$, P, Z, $X^1$ and m are as hereinbefore defined) by a process for example as described in (i) above.

Compounds of the formula XXV and salts thereof may be made by reacting compounds of the formulae XIX and IV as hereinbefore defined, under the conditions described in (a) hereinbefore, to give a compound of the formula XXV or salt thereof.

(iv) Compounds of the formula VIII and salts thereof as hereinbefore defined may be made by reacting compounds of the formulae XXIII and IV as hereinbefore defined, the reaction for example being effected by a process as described in (a) above.

(v) Compounds of the formula X as defined hereinbefore and salts thereof may for example be made by the reaction of a compound of formula VI as defined hereinbefore with a compound of the formula XXVI:

$L^1$—$R^{40}$—$L^1$ (XXVI)

(wherein $L^1$ and $R^{40}$ are as hereinbefore defined) to give a compound of the formula X. The reaction may be effected for example by a process as described in (c) above.

Compounds of the formula X and salts thereof may also be made for example by deprotecting a compound of the formula XXVII:

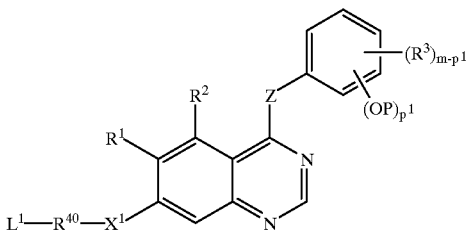

(XXVII)

(wherein $L^1$, $R^{40}$, $X^1$, $R^1$, $R^2$, $R^3$, Z, P, m and $p^1$ are as defined hereinbefore) by a process for example as described in (b) above.

Compounds of the formula XXVII and salts thereof may be made for example by reacting compounds of the formulae XXII and XXVI as defined hereinbefore, under the conditions described in (c) above.

When a pharmaceutically acceptable salt of a compound of the formula I is required, it may be obtained, for example, by reaction of said compound with, for example, an acid using a conventional procedure, the acid having a pharmaceutically acceptable anion.

Many of the intermediates defined herein are novel, for example, those of the formulae III, V, XII, XIV and XV, and these are provided as a further feature of the invention.

Intermediates of the formulae VIII, X, XXI, XXII, XXIV, XXV and XXVII are also provided as a further feature of the invention.

The identification of compounds which potently inhibit the tyrosine kinase activity associated with the VEGF receptors such as Flt and/or KDR and which inhibit angiogenesis and/or increased vascular permeability is desirable and is the subject of the present invention. These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF or epidermal growth factor (EGF) receptor cytoplasmic domains may be obtained by total gene synthesis (Edwards M, International Biotechnology Lab 5(3), 19–25, 1987) or by cloning. These may then be expressed in a suitable expression system to obtain polypeptide with tyrosine kinase activity. For example VEGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al (Oncogene, 1990, 5: 519–524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example *Spodoptera frugiperda* 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W.H. Freeman and Co, New York). For other tyrosine kinases for use in assays, cytoplasmic fragments starting from methionine 806 (KDR, Genbank accession number L04947) and methionine 668 (EGF receptor, Genbank accession number X00588) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold HNTG/PMSF (20 mM Hepes pH7.5, 150 mM sodium chloride, 10% v/v glycerol, 1% v/v Triton X100, 1.5 mM magnesium chloride, 1 mM ethylene glycol-bis(βaminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4. 0.2 mM sodium orthovanadate, 0.1% v/v Triton X100, 0.2 mM dithiothreitol). For a typical batch, stock enzyme is diluted 1 in 2000 with enzyme diluent and 50 μl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 µl of diluted compound was transferred to wells in the washed assay plates. "Total" control wells contained 10% DMSO instead of compound. Twenty five microliters of 40 mM manganese(II)chloride containing 8 µM adenosine-5'-triphosphate (ATP) was added to all test wells except "blank" control wells which contained manganese(II)chloride without ATP. To start the reactions 50 µl of freshly diluted enzyme was added to each well and the plates were incubated at room temperature for 20 minutes. The liquid was then discarded and the wells were washed twice with PBST. One hundred microliters of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microliters of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the optical density value of the "total" control wells, measured at 405 nm using a plate reading spectrophotometer, was approximately 10. "Blank" (no ATP) and "total" (no compound) control values were used to determine the dilution range of test compound which gave 50% inhibition of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3 µg/ml heparin+1 µg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% carbon dioxide. On day 4 the cultures were pulsed with 1 µCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Rat Uterine Oedema Assay

This test measures the capacity of compounds to reduce the acute increase in uterine weight in rats which occurs in the first 4–6 hours following oestrogen stimulation. This early increase in uterine weight has long been known to be due to oedema caused by increased permeability of the uterine vasculature and recently Cullinan-Bove and Koos (Endocrinology, 1993,133:829–837) demonstrated a close temporal relationship with increased expression of VEGF mRNA in the uterus. We have found that prior treatment of the rats with a neutralising monoclonal antibody to VEGF significantly reduces the acute increase in uterine weight, confirming that the increase in weight is substantially mediated by VEGF.

Groups of 20 to 22-day old rats were treated with a single subcutaneous dose of oestradiol benzoate (2.5 µg/rat) in a solvent, or solvent only. The latter served as unstimulated controls. Test compounds were orally administered at various times prior to the administration of oestradiol benzoate. Five hours after the administration of oestradiol benzoate the rats were humanely sacrificed and their uteri were dissected, blotted and weighed. The increase in uterine weight in groups treated with test compound and oestradiol benzoate and with oestradiol benzoate alone was compared using a Student T test. Inhibition of the effect of oestradiol benzoate was considered significant when $p<0.05$.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents that work by different mechanisms from those defined hereinbefore (for example linomide, inhibitors of integrin αvβ3 function, angiostatin, razoxin. thalidomide);

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor fluction) and inhibitors of growth factor function, (such growth factors include for example EGF, FGFs, platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF, especially those tumours which are significantly dependent on VEGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:

[(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet;

(vii) intermediates were not generally fully characterised and purity was assessed by thin layer chromatography (TLC), high-performance liquid chromatography (HPLC), infra-red (IR) or NMR analysis;

(viii) the following abbreviations have been used:
DMF N,N-dimethylformamide
DMSO dimethylsulphoxide
DMA N,N-dimethylacetamide
TFA trifluoroacetic acid.]

EXAMPLE 1

Isopropanolic hydrogen chloride (0.1 ml of a 5M solution) was added to a solution of 4-chloro-6,7-dimethoxyquinazoline (202 mg, 0.9 mmol) and 4-bromo-2-fluoro-5-hydroxyaniline (as described in EP 61741 A2) (206 mg, 1 mmol) in 2-butanol (8 ml). The mixture was heated at reflux for 45 minutes, then allowed to cool. The precipitated product was collected by filtration, washed with 2-butanol, and then with ether, and dried under vacuum to give 4-(4-bromo-2-fluoro-5-hydroxyanilino)-6,7-dimethoxyquinazoline hydrochloride hydrate (340 mg, 87%) as a white solid.

m.p. 265–270° C.

$^1$H NMR Spectrum: (DMSOd$_6$) 4.0(2s, 6H); 7.13(d, 1 H); 7.32(s, 1H); 7.64(d, 1 H); 8.17(s, 1H); 8.8(s, 1H); 10.6(s, 1H); 11.3(s, 1H)

MS-ESI: 394–396 [MH]$^+$

| Elemental analysis: | Found | C 43.42 | H 3.68 | N 9.33 |
| $C_{16}H_{13}BrFN_3O_3$ 1HCl 1.05H$_2$O | Requires | C 42.75 | H 3.61 | N 9.35% |

The starting material was prepared as follows:

A mixture of 4,5-dimethoxyanthranilic acid (19.7 g) and formamide (10 ml) was stirred and heated to 190° C. for 5 hours. The mixture was allowed to cool to approximately 80° C. and water (50 ml) was added. The mixture was stored at ambient temperature for 3 hours. The precipitate was isolated, washed with water and dried to give 6,7-dimethoxy-3,4-dihydroquinazolin-4-one (3.65 g).

A mixture of a portion (2.06 g) of the material so obtained, thionyl chloride (20 ml) and DMF (1 drop) was stirred and heated to reflux for 2 hours. The mixture was evaporated and the residue was partitioned between ethyl acetate and a saturated aqueous sodium hydrogen carbonate solution. The organic phase was washed with water, dried (MgSO$_4$) and evaporated. The residue was purified by column chromatography using increasingly polar mixtures of methylene chloride and ethyl acetate as eluant to give 4-chloro-6,7-dimethoxyquinazoline (0.6 g, 27%).

EXAMPLE 2

Solid potassium hydroxide (71 mg, 1.2 mmol) and then 4-chloro-6,7-dimethoxyquinazoline (0.25 g, 1.1 mmol), (prepared as described for the starting material in Example 1), were added to a melt of 2,4-dihydroxytoluene (0.6 g, 4.8 mmol) at 140° C. The mixture was stirred at 140° C. for 15 minutes, then allowed to cool. The mixture was diluted with water, and acidified to pH4 then extracted with ethyl acetate. The organic layer was washed with brine, dried (MgSO$_4$) and the solvent removed by evaporation. The crude product was first purified by flash chromatography eluting with petroleum ether/ethyl acetate (1/9) and then by absorption HPLC eluting with trichloromethane/acetonitrile (85/15) to give 6,7-dimethoxy-4-(3-hydroxy-4-methylphenoxy)quinazoline (116 mg, 34%).

m.p. 213–216° C.

$^1$H NMR Spectrum: (CDCl$_3$) 2.22(s, 3H); 4.05(s, 6H); 6.6(s, 1H); 6.69(dd, 1H); 7.2(d, 1H); 7.3(s, 1H); 7.52(s, 1H); 8.35(br s, 1H); 8.65(s, 1H)

MS-ESI: 313 [MH]$^+$

| Elemental analysis: | Found | C 65.36 | H 5.53 | N 8.92 |
| $C_{17}H_{16}N_2O_4$ | Requires | C 65.38 | H 5.16 | N 8.97% |

The starting material was prepared as follows:

Boron tribromide (3.1 ml, 3.2 mmol) was added to a solution of 2,4-dimethoxytoluene (1 g, 6.5 mmol) in pentane (10 ml) at −70° C. The reaction mixture was allowed to warm to ambient temperature and the mixture stirred for a further 2 hours. Ice water and ethyl acetate were then added and the aqueous layer basified to pH9.5 with 2M aqueous sodium hydroxide. After stirring for 10 minutes, the organic layer was separated and the aqueous layer extracted with ethyl acetate. The combined organic extract was washed with brine, dried (MgSO$_4$) and the solvent removed by evaporation. The residue was purified by flash chromatography eluting with methylene chloride/ethyl acetate (9/1) to give 2,4-dihydroxytoluene (759 mg, 94%) as a white solid.

EXAMPLE 3

As part of the procedure described in Example 2 a second compound was extracted during the absorption HPLC by eluting with trichloromethane/acetonitrile (75/25) to give 6,7-dimethoxy-4-(5-hydroxy-2-methylphenoxy)quinazoline (123 mg, 36%).

m.p. 231–239° C.

$^1$H NMR Spectrum: (CDCl$_3$) 2.1(s, 3H); 4.05(s, 6H); 6.6(s, 1H); 6.72(dd, 1H); 7.15(d, 1H); 7.32(s, 1H); 7.58(s, 1H); 8.65(s, 1H)

MS-ESI: 313 [MH]$^+$

| Elemental analysis: | Found | C 65.05 | H 5.68 | N 8.6 |
| $C_{17}H_{16}N_2O_4$ 0.1H$_2$O | Requires | C 65.00 | H 5.20 | N 8.92% |

EXAMPLE 4

A mixture of 4-(4-chloro-2-fluorophenoxy)-7-hydroxy-6-methoxyquinazoline (160 mg, 0.5 mmol), 2-bromoethyl methyl ether (83 mg, 0.6 mmol) and potassium carbonate (207 mg. 1.5 mmol) in DMF (3 ml) was heated at 180° C. for 45 minutes. The reaction mixture was allowed to cool, diluted with water and acidified to pH3.5. This aqueous mixture was extracted with ethyl acetate and the organic extract was washed with water and brine, dried (MgSO$_4$) and the solvent removed by evaporation. The residue was purified by flash chromatography eluting with methylene chloride/ether (7/3) to give 4-(4-chloro-2-fluorophenoxy)-7-(2-methoxyethoxy)-6-methoxyquinazoline (130 mg, 68%).

m.p. 167–168° C.

$^1$H NMR Spectrum: (DMSOd$_6$) 3.76(t, 2H); 3.99(s, 3H); 4.34(t, 2H); 7.4(d, 1H); 7.44(s, 1H); 7.56(t, 1H); 7.57(s, 1H); 7.70(dd, 1H); 8.56(s, 1H)

MS-ESI: 379 [MH]$^+$

| Elemental analysis: | Found | C 57.03 | H 4.53 | N 7.41 |
|---|---|---|---|---|
| C$_{18}$H$_{16}$FClN$_2$O$_4$ 0.1H$_2$O | Requires | C 56.81 | H 4.29 | N 7.36% |

The starting material was prepared as follows:

A mixture of 2-amino-4-benzyloxy-5-methoxybenzamide (J. Med. Chem. 1977, vol 20, 146–149, 10 g, 0.04 mol) and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The mixture was evaporated, water was added to the residue, the solid was filtered off, washed with water and dried. Recrystallisation from acetic acid gave 7-benzyloxy-6-methoxy-3,4-dihydroquinazolin-4-one (8.7 g, 84%).

A mixture of 7-benzyloxy-6-methoxy-3,4-dihydroquinazolin-4-one (2.82 g, 0.01 mol), thionyl chloride (40 ml) and DMF (0.28 ml) was stirred and heated at reflux for 1 hour. The mixture was evaporated and azeotroped with toluene to give 7-benzyloxy-4-chloro-6-methoxyquinazoline hydrochloride (3.45 g).

4-Chloro-2-fluoro-phenol (264 mg, 1.8 mmol) was added to a solution of 7-benzyloxy-4-chloro-6-methoxyquinazoline hydrochloride (506 mg, 1:5 mmol) in pyridine (8 ml) and the mixture heated at reflux for 45 minutes. The solvent was removed by evaporation and the residue partitioned between ethyl acetate and water. The organic layer was washed with 0.1M HCl, water and brine, dried (MgSO$_4$) and the solvent removed by evaporation. The solid residue was triturated with petroleum ether and the crude product collected by filtration and purified by flash chromatography eluting with methylene chloride/ether (9/1) to give 7-benzyloxy-4-(4-chloro-2-fluorophenoxy)-6-methoxyquinazoline (474 mg, 77%) as a cream solid.

m.p. 179–180° C.

$^1$H NMR Spectrum: (DMSOd$_6$) 3.99(s, 3H); 5.36(s, 2H); 7.35–7.5(m, 4H); 7.55–7.65(m, 5H); 7.72(d, 1H); 8.6(s, 1H)

MS-ESI: 411 [MH]$^+$

| Elemental analysis: | Found | C 63.38 | H 4.07 | N 6.78 |
|---|---|---|---|---|
| C$_{22}$H$_{16}$ClFN$_2$O$_3$ 0.06H$_2$O 0.05CH$_2$Cl$_2$ | Requires | C 63.64 | H 3.93 | N 6.73% |

A solution of 7-benzyloxy-4-(4-chloro-2-fluorophenoxy)-6-methoxyquinazoline (451 mg, 1.1 mmol) in TFA (4.5 ml) was heated at reflux for 3 hours. The mixture was diluted with toluene and the volatiles removed by evaporation. The residue was triturated with methylene chloride, collected by filtration, washed with ether and dried under vacuum to give 4-(4-chloro-2-fluorophenoxy)-7-hydroxy-6-methoxyquinazoline (320 mg, 90%).

$^1$H NMR Spectrum: (DMSOd$_6$) 4.0(s, 3H); 7.27(s, 1H); 7.43(dd, 1H); 7.56(t, 1H); 7.57(s, 1H); 7.72(dd, 1H); 8.5(s, 1H)

MS-ESI: 321 [MH]$^+$

EXAMPLE 5

4-Chloro-6,7-dimethoxyquinazoline (200 mg, 0.89 mmol), (prepared as described for the starting material in Example 1), was added to a solution of 3-hydroxybenzenethiol (168 mg, 1.3 mmol) and N,N-diisopropylethylamine (233 µl, 1.3 mmol) in DMF (5 ml). After heating at 40° C. for 10 minutes, the reaction mixture was allowed to cool, diluted with water, acidified to pH3 and the mixture extracted with ethyl acetate. The organic extract was washed with brine, dried (MgSO$_4$) and the solvent removed by evaporation. The residue was recrystallised from a mixture of ethanol and ether to give 6,7-dimethoxy-4-(3-hydroxyphenylthio)quinazoline (259 mg, 93%) as a white solid.

m.p. 221–230° C.

$^1$H NMR Spectrum: (DMSOd$_6$) 4.0(2s, 6H); 6.9(dd, 1H); 7.05(s, 1H); 7.07(d, 1H); 7.34(t, 1H); 7.35(s, 1H); 7.38(s, 1H); 8.7(s, 1H); 9.8(br s, 1H)

MS-ESI: 315 [MH]$^+$

| Elemental analysis: | Found | C 61.06 | H 4.61 | N 8.95 |
|---|---|---|---|---|
| C$_{16}$H$_{14}$N$_2$O$_3$S | Requires | C 61.13 | H 4.49 | N 8.91% |

The starting material was prepared as follows:

Boron tribromide (1.4 ml, 14 mmol) was added to a solution of 3-methoxybenzenethiol (1 g, 7.1 mmol) in methylene chloride (10 ml) at 0° C. The mixture was allowed to warm to ambient temperature and stirred for a further 60 minutes. The reaction mixture was diluted with ethyl acetate and water and basified with aqueous 2M sodium hydroxide solution to pH9. The mixture was then extracted with ethyl acetate, the combined extract washed with brine, dried (MgSO$_4$) and the solvent removed by evaporation. The residue was purified by flash chromatography eluting with petroleum ether/ethyl acetate (8/2) to give 3-hydroxybenzenethiol (819 mg, 91%).

$^1$H NMR Spectrum: (CDCl$_3$) 3.42(s, 1H); 4.85(br s, 1H); 6.6(d, 1H); 6.75(s, 1H); 6.85(d, 1H); 7.1(t, 1H)

EXAMPLE 6

Concentrated aqueous ammonia (5 ml) was added to a solution of 4-(5-acetoxy-4-chloro-2-fluoroanilino)-6-methoxy-7-(2-methoxyethoxy)quinazoline (180 mg, 0.4 mmol) in methanol (50 ml). The mixture was stirred at ambient temperature for 3 hours, and then diluted with water. Most of the methanol was removed by evaporation and the resulting precipitate collected by filtration, washed with water and dried to give 4-(4-chloro-2-fluoro-5-hydroxyanilino)-6-methoxy-7-(2-methoxyethoxy)quinazoline (73 mg, 45%).

m.p. >250° C.

$^1$H NMR Spectrum: (DMSOd$_6$) 3.29(s, 3H); 3.74(t, 2H); 3.94(s, 3H); 4.28(t, 2H); 7.15(d, 1H); 7.19(s, 1H); 7.38(d, 1H); 7.77(s, 1H); 8.36(s, 1H); 9.40(s, 1H)

MS-ESI: 394 [MH]$^+$

| Elemental analysis: | Found | C 51.1 | H 4.6 | N 9.8 |
|---|---|---|---|---|
| C$_{18}$H$_{17}$N$_3$ClFO$_4$ 1.6H$_2$O | Requires | C 51.2 | H 4.8 | N 9.9% |

The starting material was prepared as follows:

A mixture of 4-chloro-2-fluoro-5-hydroxyaniline (2.5 g, 15 mmol), (as described in EP 61741 A2), and 7-benzyloxy-4-chloro-6-methoxyquinazoline (4.2 g, 14 mmol), (prepared as described for the starting material in Example 4 but with an aqueous work up), in isopropanol was heated at reflux for 2 hours. The mixture was then allowed to cool and the solid product collected by filtration, washed with isopropanol and dried to give 7-benzyloxy-4-(4-chloro-2-fluoro-5-hydroxyanilino)-6-methoxyquinazoline hydrochloride (4.8 g, 81%). $^1$H NMR Spectrum: (DMSOd$_6$) 3.98(s, 3H); 5.18(s, 2H); 7.05(d, 1H); 7.18–7.27(m, 7H); 8.06(s, 1H); 8.38(s, 1H)

Triethylamine (216 ml, 1.5 mmol) and then acetic anhydride (133 ml, 1.4 mmol) were added to a stirred suspension of 7-benzyloxy-4-(4-chloro-2-fluoro-5-hydroxyanilino)-6-methoxy quinazoline hydrochloride (600 mg, 1.4 mmol) in methylene chloride (7 ml). The mixture was stirred at ambient temperature for 3 hours and insoluble material removed by filtration. Volatiles were removed from the filtrate by evaporation and the residue purified by flash chromatography eluting with methylene chloride/methanol (100/0 increasing in polarity to 97/3) to give 4-(5-acetoxy-4-chloro-2-fluoroanilino)-7-benzyloxy-6-methoxyquinazoline (340 mg, 52%) as a solid.

$^1$H NMR Spectrum: (DMSOd$_6$) 2.34(s, 3H); 3.94(s, 3H); 5.28(s, 2H); 7.28(s, 1H); 7.35–7.44(m, 2H); 7.50(d, 2H); 7.58(d, 1H); 7.70(d, 1H); 7.80(s, 1I); 8.37(s, 1H); 9.30(s,1H)

MS-ESI: 468 [MH]$^+$

A solution of 4-(5-acetoxy-4-chloro-2-fluoroanilino)-7-benzyloxy-6-methoxyquinazoline (250 mg, 0.54 mmol) in methanol (5 ml), trichloromethane (5 ml) and DMF (1 ml) was stirred under hydrogen at 1 atmosphere with 5% palladium-on-charcoal catalyst (100 mg) for 4 hours. The catalyst was removed by filtration through diatomaceous earth and the solvent removed by evaporation. The residue was dissolved in ethyl acetate, washed with water and brine, and dried (MgSO$_4$). Most of the solvent was removed by evaporation, the mixture was cooled and hexane added to obtain solid product which was collected by filtration, washed with hexane/ethyl acetate and dried to give 4-(5-acetoxy-4-chloro-2-fluoroanilino)-7-hydroxy-6-methoxyquinazoline (170 mg, 45%).

$^1$H NMR Spectrum: (DMSOd$_6$) 2.37(s, 3H); 3.95(s, 3H); 7.08(s, 1H); 7.59(d, 1H); 7.68(d, 1H); 7.78(s, 1H); 8.34(s, 1H); 9.48(s,1H)

1-1'-(Azodicarbonyl)dipiperidine (413 mg, 1.6 mmol) was added portionwise to a stirred mixture of 4-(5-acetoxy-4-chloro-2-fluoroanilino)-7-hydroxy-6-methoxyquinazoline (250 mg, 0.66 mmol), 2-methoxyethanol (63 ml, 0.8 mmol) and tributylphosphine (405 ml, 1.6 mmol) in methylene chloride at 0° C. The resulting solution was allowed to warm to ambient temperature and stirred for 2 hours. The precipitated solid was removed by filtration, the solvent removed from the filtrate by evaporation and the residue purified by flash chromatography eluting with acetonitrile/methylene chloride (1/9 increasing in polarity to 4/6) to give 4-(5-acetoxy4-chloro-2-fluoroanilino)-6-methoxy-7-(2-methoxyethoxy)quinazoline (180 mg, 62%) as a solid.

$^1$H NMR Spectrum: (DMSOd$_6$) 2.35(s, 3H); 3.33(s, 3H); 3.75(t, 2H); 3.95(s, 3H); 4.28(t, 2H); 7.22(s, 1H); 7.60(d, 1H); 7.72(d, 1H); 7.80(s, 1H); 8.39(s, 1H); 9.60(s,1H)

MS-ESI: 436 [MH]$^+$

EXAMPLE 7

A mixture of 4-chloro-6,7-dimethoxyquinazoline hydrochloride (2.1 g, 8 mmol), (prepared as described for the starting material in Example 1 but without the aqueous work up), and 4-chloro-2-fluoro-5-hydroxyaniline (1.43 g, 8.9 mmol), (as described in EP 61741 A2), in isopropanol (150 ml) was heated at reflux for 2 hours. The mixture was allowed to cool, the solid product collected by filtration, washed with isopropanol and dried to give 4-(4-chloro-2-fluoro-5-hydroxyanilino)-6,7-dimethoxyquinazoline hydrochloride (1.45 g, 47%).

m.p. >250° C.

$^1$H NMR Spectrum: (DMSOd$_6$) 4.0(s, 6H); 7.17(d, 1H); 7.34(s, 1H); 7.50(d, 1H); 8.22(s, 1H); 8.80(s, 1H)

MS-ESI: 350 [MH]$^+$

| Elemental analysis: | Found | C 49.2 | H 3.7 | N 10.9 |
|---|---|---|---|---|
| C$_{16}$H$_{13}$N$_3$ClFO$_3$ 1HCl | Requires | C 49.7 | H 3.6 | N 10.9% |

EXAMPLE 8

A mixture of 4-chloro-6,7-dimethoxyquinazoline hydrochloride (2.5 g, 9.6 mmol), (prepared as described for the starting material in Example 1 but without the aqueous work up), and 2-fluoro-5-hydroxy-4-methylaniline (1.48 g, 10.5 mmol) in isopropanol (150 ml) was heated at reflux for 2 hours. The mixture was allowed to cool, the solid product collected by filtration, washed with isopropanol and dried to give 4-(2-fluoro-5-hydroxy-4-methylanilino)-6,7-dimethoxyquinazoline hydrochloride (2.2 g, 71 %).

m.p. >250° C.

$^1$H NMR Spectrum: (DMSOd$_6$) 2.15(s, 3H); 3.99(s, 6H); 6.88(d, 1H); 7.10(d, 1H); 7.32(s, 1I); 8.20(s, 1H); 8.78(s, 1H) 9.66(s, 1H)

| Elemental analysis | Found | C 56.3 | H 5.4 | N 10.4 |
|---|---|---|---|---|
| C$_{17}$H$_{16}$N$_3$FO$_3$ 1HCl 0.65C$_3$H$_8$O | Requires | C 56.3 | H 5.5 | N 10.4% |

The starting material was prepared as follows:

Methyl chloroformate (6.8 ml, 88 mmol) was added over 30 minutes to a solution of 4-fluoro-2-methylphenol (10 g, 79 mmol) in 6% aqueous sodium hydroxide solution at 0° C. The mixture was stirred for 2 hours, then extracted with ethyl acetate (10 ml). The ethyl acetate extract was washed with water (100 ml) and dried (MgSO$_4$) and the solvent removed by evaporation to give 4-fluoro-2-methylphenyl methyl carbonate (11.4 g, 78%) as an oil.

$^1$H NMR Spectrum: (DMSOd$_6$) 2.14(s, 3H); 3.81(s, 3H); 7.05(m, 1H); 7.1–7.25(m, 2H)

A mixture of concentrated nitric acid (6 ml) and concentrated sulphuric acid (6 ml) was added slowly to a solution of 4-fluoro-2-methylphenyl methyl carbonate (11.$^3$4 g, 62 mmol) in concentrated sulphuric acid (6 ml) such that the temperature of the reaction mixture was kept below 50° C. The mixture was stirred for 2 hours, then ice/water was added and the precipitated product collected by filtration. The crude product was purified by chromatography on silica eluting with methylene chloride/hexane progressing through increasingly polar mixtures to methanol/methylene chloride (1:19) to give 4-fluoro-2-methyl-5-nitrophenol (2.5 g, 22%) as a solid.

$^1$H NMR Spectrum: (DMSOd$_6$, CD$_3$CO$_2$D) 2.31(s, 3H); 7.38(d, 1H); 7.58(d, 1H)

MS-ESI: 171 [MH]$^+$

A mixture of 4-fluoro-2-methyl-5-nitrophenol (2.1 g, 13 mmol), iron powder (1 g, 18 mmol) and iron(II)sulphate (1.5 g, 10 mmol) in water (40 ml) was refluxed for 4 hours. The reaction mixture was allowed to cool, neutralised with 2M aqueous sodium hydroxide and extracted with ethyl acetate (100 ml). The ethyl acetate extract was dried (MgSO$_4$) and the solvent removed by evaporation to give 2-fluoro-5-hydroxy-4-methylaniline (0.8 g, 47%) as a solid.

$^1$H NMR Spectrum: (DMSOd$_6$) 1.94(s, 3H); 4.67(s, 2H); 6.22(d, 1H); 6.65(d, 1H); 8.68(s, 1H)

MS-ESI: 142 [MH]$^+$

EXAMPLE 9

A mixture of 4-chloro-6-methoxy-7-(2-methoxyethoxy) quinazoline (76 mg, 0.28 mmol) and 2-fluoro-5-hydroxy-4-methylaniline (40 mg, 0.28 mmol), (prepared as described for the starting material in Example 8), in isopropanol (2.5 ml) was stirred and heated at reflux for 7 hours. The reaction mixture was allowed to cool and the precipitated product collected by filtration, washed with isopropanol and dried to give 4-(2-fluoro-5-hydroxy4-methylanilino)-6-methoxy-7-(2-methoxyethoxy)quinazoline hydrochloride (79 mg 66%) as a white solid.

m.p. >275° C.

$^1$H NMR Spectrum: (DMSOd$_6$) 2.19(s, 3H); 3.36(s, 3H); 3.80(m, 2H); 4.00(s, 3H); 4.33(m, 2H); 6.90(d, 1H); 7.10(d, 1H); 7.37(s, 1H); 8.20(s, 1H); 8.75(s, 1H) 9.65(br s, 1H); 11.25(br s, 1H)

MS-ESI: 374 [MH]$^+$

| Elemental analysis: | Found | C 55.7 | H 4.8 | N 10.1 |
|---|---|---|---|---|
| C$_{19}$H$_{20}$N$_3$FO$_4$ 1HCl | Requires | C 55.7 | H 5.2 | N 10.3% |

The starting material was prepared as follows:

A mixture of ethyl 4-hydroxy-3-methoxybenzoate (9.8 g, 50mmol), 2-bromoethyl methyl ether (8.46 ml, 90 mmol) and potassium carbonate (12.42 g, 90 mmol) in acetone (60 ml) was heated at reflux for 30 hours. The mixture was allowed to cool and the solids removed by filtration. The volatiles were removed from the filtrate by evaporation and the residue triturated with hexane to give ethyl 3-methoxy-4-(2-methoxyethoxy)benzoate (11.3 g, 89%) as a white solid.

m.p. 57–60° C.

$^1$H NMR Spectrum: (DMSOd$_6$) 1.31(t, 3H); 3.29(s, 3H); 3.32(s, 3H); 3.68(m, 2H); 4.16(m, 2H); 4.28(q, 2H); 7.06(d, 1H); 7.45(d, 1H); 7.56(dd, 1H)

MS-FAB: 255 [MH]$^+$

Ethyl 3-methoxy-4-(2-methoxyethoxy)benzoate (9.5 g, 37 mmol) was added portionwise to stirred concentrated nitric acid (75 ml) at 0° C. The mixture was allowed to warm to ambient temperature and stirred for a further 90 minutes. The mixture was diluted with water and extracted with methylene chloride, dried (MgSO$_4$) and the solvent removed by evaporation. The residue was triturated with hexane to give ethyl 5-methoxy-4-(2-methoxyethoxy)-2-nitrobenzoate (10.6 g, 95%) as an orange solid.

m.p. 68–69° C.

$^1$H NMR Spectrum: (DMSOd$_6$) 1.27(t, 3H); 3.30(s, 3H); 3.69(m, 2H); 3.92(s, 3H); 4.25(m, 2H); 4.29(q, 2H); 7.30(s, 1H); 7.65(s, 1H)

MS-CI: 300 [MH]$^+$

A mixture of ethyl 5-methoxy-4-(2-methoxyethoxy)-2-nitrobenzoate (10.24 g, 34 mmol), cyclohexene (30 ml) and 10% palladium-on-charcoal catalyst (2.0 g) in methanol (150 ml) was heated at reflux for 5 hours. The reaction mixture was allowed to cool and diluted with methylene chloride. The catalyst was removed by filtration and the volatiles removed from the filtrate by evaporation. The residue was recrystallised from ethyl acetate/hexane to give ethyl 2-amino-5-methoxy-4-(2-methoxyethoxy) benzoate (8.0 g) as a buff solid. Formamide (80 ml) was added to this product and the mixture heated at 170° C. for 18 hours. About half the solvent was removed by evaporation under high vacuum and the residue was left to stand overnight. The solid product was collected by filtration, washed with ether and dried to give 6-methoxy-7-(2-methoxyethoxy)-3,4-dihydroquinazolin-4-one (5.3 g, 62% over two steps) as a grey solid.

$^1$H NMR Spectrum: (DMSOd$_6$) 3.35(s, 3H); 3.74(m, 2H); 3.89(s, 3H); 4.26(m, 2H); 7.15(s, 1H); 7.47(s, 1H); 7.98(s, 1H); 12.03(br s, 1 H)

MS-CI: 251 [MH]$^+$

DMF (0.5 ml) was added to a mixture of 6-methoxy-7-(2-methoxyethoxy)-3,4-dihydroquinazolin-4-one (5.1 g, 20 mmol) in thionyl chloride (50 ml). The mixture was stirred and heated at reflux for 3 hours, allowed to cool and the excess thionyl chloride removed by evaporation. The residue was suspended in methylene chloride and washed with aqueous sodium hydrogen carbonate solution. The aqueous phase was extracted with methylene chloride and the combined extracts dried (MgSO$_4$). The crude product was recrystallised from methylene chloride/hexane to give 4-chloro-6-methoxy-7-(2-methoxyethoxy)quinazoline (2.8 g, 51%) as a fine white solid.

$^1$H NMR Spectrum: (DMSOd$_6$) 3.37(s, 3H); 3.77(m, 2H); 4.01(s, 3H); 4.37(m, 2H); 7.40(s, 1H); 7.49(s, 1H); 8.88(s, 1H)

MS-CI: 269 [MH]$^+$

EXAMPLE 10

A mixture of 4-chloro-6,7-dimethoxyquinazoline hydrochloride, (152 mg, 0.6 mmol), (prepared as described for the starting material in Example 1 but without the aqueous work up), and 4-bromo-2,6-difluoroaniline (121 mg, 0.6 mmol) in isopropanol (7 ml) was heated at reflux for 2 hours. The mixture was allowed to cool, the solid product collected by filtration, washed with isopropanol and dried to give 4-(4-bromo-2,6-difluoroanilino)-6,7-dimethoxyquinazoline hydrochloride (81 mg, 35%).

$^1$H NMR Spectrum: (DMSOd$_6$) 4.0(s×2, 3H each); 7.2(s, 1H); 7.35(d, 2H); 8.2(s, 1H); 8.9(s, 1H); 11.8(brs, 1H)

MS-ESI: 396 [MH]$^+$

EXAMPLE 11

4-Chloro-6,7-dimethoxyquinazoline hydrochloride (300 mg, 1.15 mmol), (prepared as described for the starting material in Example 1 but without the aqueous work up), and 2,4-difluoro-5-hydroxyaniline (184 mg, 0.90 mmol) in isopropanol (10 ml) were heated at reflux for 2 hours. The reaction mixture was then allowed to cool, the precipitated product collected by filtration, washed with isopropanol and dried to give 4-(2,4-difluoro-5-hydroxyanilino)-6,7-dimethoxyquinazoline hydrochloride (250 mg, 65%)

$^1$H NMR Spectrum: (DMSOd$_6$) 3.99(s, 6H); 7.05(dd, 1H); 7.17(s, 1H); 7.40(dd, 1H); 8.10(s, 1H); 8.68(s, 1H)

MS-ESI: 334 [MH]$^+$

| Elemental analysis: | Found | C 51.8 | H 3.9 | N 11.3 |
|---|---|---|---|---|
| C$_{16}$H$_{13}$N$_3$O$_3$F$_2$ 1HCl | Requires | C 52.0 | H 3.8 | N 11.4% |

The starting material was prepared as follows:

Methyl chloroformate (16.35 ml, 0.173 mol) was added to a solution of 2,4difluorophenol (25 g, 0.192 mol) and sodium hydroxide (8.1 g, 0.203 mol) in water (140 ml). The mixture was stirred at ambient temperature for 2 hours and then extracted with ethyl acetate. The extract was washed with water, dried (MgSO$_4$) and the volatiles removed by evaporation to give 2,4-difluoro-1-methoxycarbonyloxybenzene (32 g, 89%).

$^1$H NMR Spectrum: (DMSOd$_6$) 3.85(s, 3H); 7.64(d, 2H); 7.72(d,1H)

A mixture of concentrated nitric acid (4 ml) and concentrated sulphuric acid (4 ml) was added slowly to a cooled mixture of 2,4-difluoro-1-methoxycarbonyloxybenzene (50 g, 0.027 mol) in concentrated sulphuric acid (4 ml) such that the reaction temperature was maintained below 30° C. The mixture was stirred for a further 3 hours, diluted with ice/water and the precipitated product collected by filtration washed with water and dried to give 2,4-difluoro-5-methoxycarbonyloxy-1-nitrobenzene (2.8 g, 45%).

$^1$H NMR Spectrum: (DMSOd$_6$) 3.85(s, 3H); 7.97(dd, 1H); 8.44(dd, 1H)

A mixture of 2,4-difluoro-5-methoxycarbonyloxy-1-nitrobenzene (2.7 g, 0.012 mol) and 10% palladium-on-charcoal catalyst (500 mg) in ethanol (20 ml) and ethyl acetate (10 ml) was stirred under 1 atmosphere of hydrogen for 4 hours. The catalyst was removed by filtration through diatomaceous earth and the solvent removed by evaporation to give 2,4-difluoro-5-methoxycarbonyloxyaniline (2.3 g, 97%).

$^1$H NMR Spectrum: (DMSOd$_6$) 3.82(s, 3H); 5.20(s, 2H); 6.65(dd,1H); 7.20(dd, 1H)

MS-ESI: 204 [MH]$^+$

Concentrated aqueous ammonia (20 ml) was added to a solution of 2,4-difluoro-5-methoxycarbonyloxyaniline (2.0 g, 9.85 mmol) in ethanol (100 ml) and the mixture stirred at ambient temperature for 3 hours. The reaction mixture was diluted with water and most of the organic volatiles were removed by evaporation. The aqueous residue was neutralised to pH7 and extracted with ethyl acetate. The extracts were washed with water, dried (MgSO$_4$) and the solvent removed by evaporation to give 2,4-difluoro-5-hydroxyaniline (1.2 g, 85%).

$^1$H NMR Spectrum: (DMSOd$_6$) 4.78(s, 2H); 6.34(t,1H); 6.87(t, 1H); 9.23(s, 1H)

MS-ESI: 145 [MH]$^+$

EXAMPLE 12

6-Methoxy-7-(2-methoxyethoxy)-3,4-dihydroquinazolin-4-one (200 mg, 0.8 mmol), (prepared as described for the starting material in Example 9), and DMF (0.1 ml) in thionyl chloride (20 ml) were heated at reflux for 2 hours. Excess thionyl chloride was removed by evaporation and the residue azeotroped with toluene. The residue was dissolved in isopropanol (15 ml), 2,4-difluoro-5-hydroxyaniline (128 mg, 0.88 mmol), (prepared as described for the starting material in Example 11), added, and the mixture heated at reflux for 2 hours. The reaction mixture was then allowed to cool, the precipitated product collected by filtration, washed with isopropanol and dried to give 4-(2,4-difluoro-5-hydroxyanilino)-6-methoxy-7-(2-methoxyethoxy)quinazoline hydrochloride (83 mg, 28%).

$^1$H NMR Spectrum: (DMSOd$_6$) 3.35(s, 3H); 3.77(t, 2H); 4.00(s, 3H); 4.30(t, 2H); 7.10)(dd, 1H); 7.36(s, 1H); 7.40(t, 2H); 8.20(s, 1H); 8.78(d, 2H)

MS-ESI: 378 [MH]$^+$

| Elemental analysis: | Found | C 51.8 | H 4.2 | N 10.1 |
|---|---|---|---|---|
| C$_{18}$H$_{17}$N$_3$O$_4$F$_2$ 1HCl | Requires | C 52.2 | H 4.4 | N 10.2% |

EXAMPLE 13

A mixture of 7-(2-acetoxyethoxy)-4-(5-benzyloxy-2-fluoro-4-methylanilino)-6-methoxyquinazoline (133 mg, 0.27 mmol) and 10% palladium-on-charcoal catalyst (50 mg) in ethyl acetate (8 ml) was stirred under 1 atmosphere of hydrogen at ambient temperature for 18 hours. The catalyst was removed by filtration through diatomaceous earth and most of the solvent removed by evaporation and hexane added to the residue. The resulting precipitated product was collected by filtration and dried to give 7-(2-acetoxyethoxy)-4-(2-fluoro-5-hydroxy4-methylanilino)-6-methoxyquinazoline (16 mg, 15%).

$^1$H NMR Spectrum: (DMSOd$_6$) 2.05(s, 3H); 2.13(s, 3H); 3.91 (s, 3H); 4.3–4.4(m, 4H); 6.90(d, 1H); 6.98(d, 1H); 7.18(s, 1H); 7.79(s, 1H); 8.30(s, 1H); 9.15(s, 2H)

MS-ESI: 402 [MH]$^+$

The starting material was prepared as follows:

A mixture of 4-fluoro-2-methyl-5-nitrophenol (4.69 g, 27 mmol), (prepared as described for the starting material in Example 8), benzyl bromide (3.59 ml, 30 mmol) and potassium carbonate (7.58 g, 55 mmol) in DMF (100 ml) was heated at 80° C. for 4 hours. The reaction mixture was allowed to cool and diluted with water and stirred for 15 minutes. The precipitated product was collected by filtration, washed with water and dried to give 5-benzyloxy-2-fluoro-4-methyl-1-nitrobenzene (6.4 g, 89%).

$^1$H NMR Spectrum: (DMSOd$_6$) 2.28(s, 3H); 5.22(s, 2H); 7.3–7.5(m, 6H); 7.70(s, 1H)

5-Benzyloxy-2-fluoro-4-methyl-1-nitrobenzene (500 mg, 1.9 mmol) in methanol (10 ml) was added to a suspension of Raney nickel (75 mg) and hydrazine hydrate (465 ml, 9.5 mmol) in methanol (10 ml) and heated at reflux. The mixture was maintained under reflux for 15 minutes and then the insoluble materials removed by filtration through diatomaceous earth. The filter pad was washed with methanol and the solvent removed from the filtrate by evaporation to give 5-benzyloxy-2-fluoro-4-methylaniline (440 mg, 99%).

$^1$H NMR Spectrum: (DMSOd$_6$) 2.02(s, 3H); 4.88(s, 2H); 4.98(s, 2H); 6.44(d, 1H); 6.76(d, 1H); 7.3–7.5(m, 5H)

A mixture of 7-benzyloxy-6-methoxy-3,4-dihydroquinazolin-4-one (5.0 g, mmol), (prepared as described for the starting material in Example 4), acetic anhydride (200 ml), sodium acetate (12 g), 10% palladium-on-charcoal catalyst (1.5 g) in toluene (100 ml) was stirred under an atmosphere of hydrogen for 3 hours. The mixture was filtered and the filtrate was evaporated. The residue was partitioned between a mixture of ethyl acetate (500 ml), methanol (20 ml) and water (300 ml). The organic phase was separated, dried (MgSO$_4$) and the solvent removed by evaporation. The residue was triturated with hexane to give 7-acetoxy-6-methoxy-3,4-dihydroquinazolin-4-one (1.1 g, 27%).

$^1$H NMR Spectrum: (DMSOd$_6$) 2.29(s, 3H); 3.84(s, 3H); 7.42(s, 1H); 7.62(s, 1H); 8.1(br s, 1H)

MS-ESI: 235 [MH]$^+$

A mixture of 7-acetoxy-6-methoxy-3,4-dihydroquinazolin-4-one (1.69 g, 7.2 mmol), thionyl chloride (50 ml) and DMF (3 drops) was heated at reflux for 2 hours. The excess thionyl chloride was removed by evaporation and the residue azeotroped with toluene. The residue was partitioned between methylene chloride and saturated aqueous sodium hydrogen carbonate solution. The organic phase was separated, dried (MgSO$_4$) and the solvent removed by evaporation. 5-Benzyloxy-2-fluoro-4-methylaniline (1.8 g, 7.8 mmol) in isopropanol (50 ml) was added to the residue and the mixture heated at reflux for 2 hours. The mixture was allowed to cool, hexane added and the precipitated product collected by filtration to give 7-acetoxy-4-(5-benzyloxy-2-fluoro-4-methylanilino)-6-methoxyquinazoline (1.34 g, 43%).

$^1$H NMR Spectrum: (DMSOd$_6$) 2.24(s, 3H); 2.38(s, 3H); 4.00(s, 3H); 5.10(s, 2H); 7.1–7.5(m, 7H); 7.75(s, 1H); 8.39(s, 1H); 8.77(s, 1H)

Concentrated aqueous ammonia (25 ml) was added to a solution of 7-acetoxy4-(5-benzyloxy-2-fluoro-4-methylanilino)-6-methoxyquinazoline (1.5 g, 3.4 mmol) in methanol (100 ml). The mixture was stirred at ambient temperature for 30 minutes, and most of the organic volatiles were then removed by evaporation. Further water was added and the precipitate was collected by filtration, washed with water and dried to give 4-(5-benzyloxy-2-fluoro-4-methylanilino)-7-hydroxy-6-methoxyquinazoline (1.2 g, 89%) which was used without further characterisation.

A mixture of 4-(5-benzyloxy-2-fluoro4-methylanilino)-7-hydroxy-6-methoxyquinazoline (440 mg, 1 mmol), 2-bromoethanol (77 ml, 1 mmol) and potassium carbonate (150 mg, 1.1 mmol) in DMF (5 ml) was heated at 50° C. for 1 hour, further 2-bromoethanol (42 ml, 0.6 mmol) and potassium carbonate (150 mg, 1.1 mmol) was added and the mixture was maintained at 50° C. for 2 hours. The reaction mixture was diluted with water, neutralised with 2M hydrochloric acid and extracted with ethyl acetate. The extracts were dried (MgSO$_4$), the solvent removed by evaporation and the residue triturated with ether and hexane to give 4-(5-benzyloxy-2-fluoro-4-methylanilino)-7-(2-hydroxyethoxy)-6-methoxyquinazoline (200 mg, 41%).

$^1$H NMR Spectrum: (DMSOd$_6$) 2.21(s, 3H); 3.80(t, 2H); 3.94(s, 3H); 4.14(t, 2H); 4.90(s, 1H); 5.10(s, 2H); 7.05–7.2 (m, 2H); 7.25–7.45(m, 5H); 7.79(s, 1H); 8.30(s, 1H); 9.20(s, 1H)

Acetic anhydride (55 ml, 0.58 mmol) was added to a mixture of 4-(5-benzyloxy-2-fluoro-4-methylanilino)-7-(2-hydroxyethoxy)-6-methoxyquinazoline (233 mg, 0.52 mmol), triethylamine (80 ml, 0.57 mmol) and 4-(N,N-dimethylamino)pyridine (5 mg) in ethyl acetate (50 ml). The mixture was stirred for 2 hours at ambient temperature, water was added, the organic layer separated, washed with water and brine and dried (MgSO$_4$). Most of the solvent was removed by evaporation and hexane added. The precipitated product was collected by filtration to give 7-(2-acetoxyethoxy)-4-(5-benzyloxy-2-fluoro-4-methylanilino)-6-methoxyquinazoline (110 mg, 43%).

$^1$H NMR Spectrum: (DMSOd$_6$) 2.03(s, 3H); 2.22(s, 3H); 3.92(s, 3H); 4.3–4.4(m, 4H); 5.08(s, 2H); 7.13(d, 1H); 7.18(d, 1H); 7.3–7.45(m, 5H); 7.80(s, 1H); 8.30(s, 1H); 9.42(s, 1H)

EXAMPLE 14

A mixture of 4-(5-benzyloxy-2-fluoro-4-methylanilino)-7-(2-hydroxyethoxy)-6-methoxyquinazoline (150 mg, 0.33 mmol), (prepared as described for the starting material in Example 13), and 10% palladium-on-charcoal catalyst (20 mg) in ethyl acetate (8 ml) was stirred under 1 atmosphere of hydrogen at ambient temperature for 18 hours. The catalyst was removed by filtration through diatomaceous earth and most of the solvent removed by evaporation and hexane added to the residue. The resulting precipitate was collected by filtration and dried to give 4-(2-fluoro-5-hydroxy-4-methylanilino)-7-(2-hydroxyethoxy)-6-methoxyquinazoline (50 mg, 41%).

$^1$H NMR Spectrum: (DMSOd$_6$) 2.14(s, 3H); 3.80(q, 2H); 3.94(s, 3H); 4.15(t, 2H); 4.90(t, 1H); 6.90(d, 1H); 7.00(d, 1H); 7.17(s, 1H); 7.80(s, 1H); 8.33(s, 1H); 9.32(s, 1H); 9.37(s, 1H)

MS-ESI: 360 [MH]$^+$

EXAMPLE 15

4-Chloro-6,7-dimethoxyquinazoline hydrochloride (210 mg, 0.8 mmol), (prepared as described for the starting material in Example 1 but without the aqueous work up), and 4-chloro-2,6-difluoroaniline hydrochloride (177 mg, 0.89 mmol) in isopropanol (8 ml) were heated at reflux for 2 hours. The reaction mixture was then allowed to cool, hexane added and the precipitated product collected by filtration, washed with isopropanol and dried to give 4-(4-chloro-2,6-difluoroanilino)-6,7-dimethoxyquinazoline hydrochloride (45 mg, 16%).

m.p. >250° C.

$^1$H NMR Spectrum: (DMSOd$_6$) 4.00(s, 3H); 4.01(s, 3H); 7.35(s, 1H); 7.63(d, 2H); 8.22(s, 1H); 8.81(s, 1H)

MS-ESI: 352 [MH]$^+$

The starting material was prepared as follows:

A solution of 3,5-difluoronitrobenzene (20 g, 126 mmol) and ethyl dichloroacetate (15.8 ml, 129 mmol) in DMF (60 ml) was added to potassium t-butoxide (31.8 g, 283 mmol) in DMF (500 ml) at –25° C. over 30 minutes. The mixture was stirred for 15 minutes at –25° C. then poured on to a mixture of ice (600 g) and 2M hydrochloric acid (500 ml). The aqueous mixture was extracted with ethyl acetate, the combined extracts were washed with water and sodium hydrogen carbonate solution and dried (MgSO$_4$) and the solvent removed by evaporation to give ethyl 2-chloro-2-(2,6-difluoro-4-nitrophenyl)ethanoate (34 g, 97%).

$^1$H NMR Spectrum: (DMSOd$_6$) 1.15(t, 3H); 4.1–4.3(m, 2H); 6.44(s, 1H); 8.17(d, 2H)

2.5M Aqueous sodium hydroxide solution (300 ml) was added over 5 minutes to a solution of ethyl 2-chloro-2-(2,6-difluoro-4-nitrophenyl)ethanoate (34.86 g 125 mmol) in ethanol (300 ml) at 5° C. such that the reaction temperature was kept below 25° C. The mixture was cooled to 18° C. and 30% hydrogen peroxide (40 ml) was added. The mixture was stirred at 20° C. for 2.5 hours. Sodium sulphite was added until the peroxide test was negative, the mixture was acidified to pH1 with 6M hydrochloric acid and extracted with ethyl acetate. The organic extracts were back extracted with saturated aqueous sodium hydrogen carbonate solution, the aqueous extracts were acidified with concentrated hydrochloric acid and extracted with ethyl acetate. The extracts were dried (MgSO$_4$) and the solvent removed by evaporation to give 2,6-difluoro-4-nitrobenzoic acid (4.89 g, 19%).

$^1$H NMR Spectrum: (DMSOd$_6$) 8.14(d, 2H)

A mixture of 2,6-difluoro-4-nitrobenzoic acid (2.5 g, 12 mmol) and 10% palladium-on-charcoal catalyst (500 mg) in ethanol (I50 ml) was stirred under 1 atmosphere of hydrogen at ambient temperature for 3 hours. The catalyst was removed by filtration through diatomaceous earth, the filter pad washed with ethanol and the solvent removed by evaporation to give 4-amino-2,6-difluorobenzoic acid (3–8 g, 91%).

$^1$H NMR Spectrum: (DMSOd$_6$) 6.12(d, 2H); 6.28(s, 2H)

MS-ESI: 174 [MH]$^+$

A solution of sodium nitrite (220 mg, 3.18 mmol) in concentrated sulphuric acid (2 ml) was added over 15 minutes to a suspension of 4-amino-2,6-difluorobenzoic acid (550 mg, 3.18 mmol) in acetic acid (6 ml) at 15° C. The mixture was stirred at 15° C. for 1 hour then heated to 90° C. and poured into a solution of copper(I)chloride (800 mg) in concentrated hydrochloric acid (11 ml) at 95° C. The mixture was heated at 95° C. for 45 minutes and then allowed to cool. The mixture was diluted with water, extracted with ethyl acetate, the organic extracts dried (MgSO$_4$) and the solvent removed by evaporation to give 4-chloro-2,6-difluorobenzoic acid (600 mg, 98%)

$^1$H NMR Spectrum: (DMSOd$_6$) 7.50(d, 2H)

MS-ESI: 192 [MH]$^+$

4-Chloro-2,6-difluorobenzoic acid (500 mg, 2.6 mmol) was added to a solution of diphenylphosphoryl azide (737 mg, 3 mmol) in t-butanol (8 ml) followed by triethylamine (477 ml, 6 mmol) and the mixture heated at reflux for 2 hours. The reaction mixture was allowed to cool and the solvent removed by evaporation. The residue was dissolved in ethyl acetate, washed with water, dried (MgSO$_4$) and purified by column chromatography eluting with increasingly polar mixtures of methylene chloride, hexane and methanol (/1/1/0 to 95/0/5) to give N-t-butoxycarbonyl-4-chloro-2,6-difluoroaniline (170 mg, 25%).

$^1$H NMR Spectrum: (DMSOd$_6$) 1.41(s, 9H); 7.39(d, 2H); 8.86(s, 1H)

A saturated solution of hydrogen chloride in ethyl acetate (4 ml) was added to N-t-butoxycarbonyl-4-chloro-2,6-difluoroaniline (330 mg, 1.3 mmol) and the mixture stirred at ambient temperature for 2 hours. The precipitate was collected by filtration to give 4-chloro-2,6-difluoroaniline hydrochloride (140 mg, 56%).

$^1$H NMR Spectrum: (DMSOd$_6$) 6.12(s, 2H); 7.08(d, 2H)

EXAMPLE 16

A mixture of 6-methoxy-7-(3-morpholinopropoxy)-3,4-dihydroquinazolin-4-one (370 mg, 1.16 mmol), thionyl chloride (5 ml) and DMF (3 drops) was heated at reflux for 2 hours and allowed to cool. The excess thionyl chloride was removed by evaporation and the residue was azeotroped with toluene. A solution of 2-fluoro-5-hydroxy-4-methylaniline (220 mg, 1.56 mmol) in isopropanol (10 ml) was added to the solid residue and the mixture was heated at reflux for 2 hours and then allowed to cool. The resulting precipitate was collected by filtration, washed with methylene chloride and dried. The impure solid product was treated with aqueous sodium hydrogen carbonate, to give a suspension and the product was recollected by filtration and purified by column chromatography eluting with methylene chloride/methanol (9/1) to give 4-(2-fluoro-5-hydroxy-4-methylanilino)-6-methoxy-7-(3-morpholinopropoxy) quinazoline (140 mg, 27%).

$^1$H NMR Spectrum: (DMSOd$_6$) 2.0(m, 2H); 2.15(s, 3H); 2.35–2.55(m, 6H); 3.55(br t, 4H); 3.90(s, 3H); 4.20(t, 2H); 6.85–6.95(m, 2H); 7.10(s, 1H); 7.75(s, 1H); 8.25(s, 1H); 9.20(s, 2H)

| Elemental analysis: | Found | C 62.2 | H 6.1 | N 12.4 |
|---|---|---|---|---|
| C$_{23}$H$_{27}$N$_4$O$_4$F | Requires | C 62.4 | H 6.2 | N 12.7% |

The starting material was prepared as follows:

Sodium hydride (400 mg of an 80% suspension in paraffin oil, 13.3 mmol) was added to a solution of phenol (1.26 g, 13.3 mmol) in dry 1-methyl-2-pyrrolidinone (20 ml) and the mixture stirred for 10 minutes. 7-Benzyloxy-4-chloro-6-methoxyquinazoline (1.6 g, 5.3 mmol), (prepared as described for the starting material in Example 4 but with an aqueous work up), was then added and the reaction mixture heated at 110° C. for 2 hours. The mixture was allowed to cool, water was added and the mixture extracted with ethyl acetate (3×100 ml). The combined extracts were then washed with 2M sodium hydroxide solution, water and brine. Removal of the solvent under reduced pressure gave 7-benzyloxy-6-methoxy-4-phenoxyquinazoline (1.6 g, 84%) as a yellowish solid.

$^1$H NMR Spectrum: (DMSOd$_6$) 3.98(s, 3H); 5.37(s, 2H); 7.25–7.6(m, 1H); 7.60(s, 1H); 8.54(s, 1H)

MS-ESI: 300 [MH]$^+$

7-Benzyloxy-6-methoxy-4-phenoxyquinazoline (160 mg, 0.44 mmol) in TFA (3 ml) was heated at reflux for 30 minutes. The solvent was removed by evaporation and the residue treated with aqueous sodium hydrogen carbonate solution. The precipitated product was collected by filtration, washed with water and dried to give 7-hydroxy-6-methoxy-4-phenoxyquinazoline (105 mg, 88%).

$^1$H NMR Spectrum: (DMSOd$_6$) 4.00(s, 3H); 7.20(s, 1H); 7.25–7.35(m, 3H); 7.$^{4-7.55}$(m, 2H); 7.58(s, 1H); 10.73(s, 1H)

MS-ESI: 269 [MH]$^+$ 4-(3-Chloropropyl)morpholine (0.9 g, 4.5 mmol), (J. Am-Chem. Soc. 1945, 67, 736, 174 mg, 1.06 mmol), was added to 7-hydroxy-6-methoxy-4-phenoxyquinazoline (1.0 g, 3.7 mmol), potassium carbonate (2.6 g, 18.8 mmol) in DMF (30 ml). The mixture was heated at 110° C. for 4 hours and then allowed to cool. The solids were removed by filtration, and the volatiles were removed from the filtrate by evaporation. The residue was purified by column chromatography eluting with methylene chloride/methanol, (96/4) to give 6-methoxy-7-(3-morpholinopropoxy)-4-phenoxyquinazoline (1.0 g, 68%).

$^1$H NMR Spectrum: (DMSOd$_6$) 2.0 (m, 2H); 2.35–2.55 (m, 6H); 3.6(br s, 4H); 3.95(s, 3H); 4.25(t, 2H); 7.25–7.35 (m, 3H); 7.40(s, 1H); 7.45–7.55(m, 2H); 7.55(s, 1H); 8.50(s, 1H)

MS-ESI: 396 [MH]$^+$

A mixture of 6-methoxy-7-(3-morpholinopropoxy)-4-phenoxyquinazoline (980 mg, 2.48 mmol) and 2M hydrochloric acid (25 ml) was heated at 100° C. for 2 hours and allowed to cool. The solution was basified with solid sodium hydrogen carbonate, and the product was extracted with methylene chloride. The organic phase was passed through phase separating paper and the solvent removed by evaporation to give 6-methoxy-7-(3-morpholinopropoxy)-3, 4dihydroquinazolin-4-one (750 mg, 95%) as a pale brown solid which was used without further purification.

MS-ESI: 320 [MH]$^+$

EXAMPLE 17

A mixture of 6-methoxy-7-(3-morpholinopropoxy)-3,4-dihydroquinazolin-4-one (370 mg, 1.16 mmol), (prepared as described for the starting material in Example 16), thionyl chloride (5 ml) and DMF (3 drops) was heated at reflux for 2 hours and allowed to cool. The excess thionyl chloride was removed by evaporation and the residue was azeotroped with toluene. A solution of 4-chloro-2-fluoro-5-hydroxyaniline (210 mg, 1.30 mmol), (as described in EP 61741 A2), in isopropanol (10 ml) was added to the solid residue and the mixture was heated at reflux for 2 hours and then allowed to cool. The mixture was diluted with acetone and the precipitate collected by filtration. The crude solid product was suspended in aqueous sodium hydrogen carbonate, collected again by filtration and purified by column chromatography eluting with methylene chloride/methanol/ammonia (100/10/1) to give 4-(4-chloro-2-fluoro-5-hydroxyaniline)-6-methoxy-7-(3-morpholinopropoxy) quinazoline (160 mg, 30%).

$^1$H NMR Spectrum: (DMSOd$_6$) 2.0(m, 2H); 2.35–2.55(m, 6H); 3.6(t, 4H); 3.95(s, 3H); 4.15(t, 2H); 7.15(m, 2H); 7.35(d, 1H); 7.75(s, 1H); 8.35(s, 1H); 9.35(s, 1H); 10.15(s, 1H),

MS-ESI: 463 [MH]$^+$

| Elemental analysis: | Found | C 57.1 | H 5.3 | N 12.0 |
|---|---|---|---|---|
| $C_{22}H_{24}N_4O_4FCl$ | Requires | C 57.1 | H 5.2 | N 12.1% |

EXAMPLE 18

1M Ethereal hydrogen chloride (3.1 ml, 3.1 mmol) was added to 4-chloro-6-methoxy-7-(2-methylthioethoxy) quinazoline (0.8 g, 2.8 mmol) and 2-fluoro-5-hydroxy-4-methylaniline (0.44 g, 3.12 mmol), (prepared as described for the starting material in Example 8), in isopropanol (25 ml). The mixture was heated at reflux for 2 hours, then allowed to cool. The resulting suspension was diluted with acetone and the precipitate collected by filtration and purified by column chromatography eluting with methylene chloride/methanol/ammonia (100/8/1) to give 4-(2-fluoro-5-hydroxy-4-methylanilino)-6-methoxy-7-(2-methylthioethoxy)quinazoline (580 mg, 52%).

$^1$H NMR Spectrum: (DMSOd$_6$) 2.15 (s, 3H); 2.23(s, 3H); 2.94 (t, 2H); 3.95(s, 3H); 4.33(t, 2H); 6.92(d, 1H); 7.00(d, 1H); 7.20(s, 1H); 7.83(s, 1H); 8.38(s, 1H); 9.30(s, 1H); 9.33(s, 1H)

MS-ESI: 390 [MH]$^+$

| Elemental analysis: | Found | C 57.4 | H 5.1 | N 10.5 |
|---|---|---|---|---|
| $C_{19}H_{20}N_3O_3FS$ 0.5H$_2$O | Requires | C 57.3 | H 5.3 | N 10.5% |

The starting material was prepared as follows:

2-Chloroethyl methyl sulphide (1.2 g, 10.9 mmol) was added to 7-hydroxy-6-methoxy-4-phenoxyquinazoline (2.25 g, 8.4 mmol), (prepared as described for the starting material in Example 16), and potassium carbonate (6.0 g, 43.4 mmol) in DMF (70 ml). The mixture was heated at 110° C. for 4 hours and allowed to cool. The mixture was filtered, and the volatiles were removed from the filtrate by evaporation. The residue was purified by column chromatography eluting with methylene chloride/methanol (96/4) to give 6-methoxy-7-(2-methylthioethoxy)4-phenoxyquinazoline (1.55 g, 54%).

A mixture of 6-methoxy-7-(2-methylthioethoxy)-4-phenoxyquinazoline (1.5 g, 4.4 mmol) and 2M hydrochloric acid (25 ml) was heated at 100° C. for 2 hours. The mixture was allowed to cool, and methylene chloride was added with stirring to give a white precipitate. The precipitate was collected by filtration, washed with water and methylene chloride and dried to give 6-methoxy-7-(2-methylthioethoxy)-3,4-dihydroquinazolin-4-one hydrochloride (1.1 g, 83%).

$^1$H NMR Spectrum: (DMSOd$_6$) 2.22(s, 3H); 2.94(t, 2H); 3.92(s, 3H); 4.30(t, 2H); 7.36(s, 1H); 7.49(s, 1H); 8.80(s, 1H)

MS-ESI: 267 [MH]$^+$

| Elemental analysis: | Found | C 46.4 | H 5.2 | N 8.8 |
|---|---|---|---|---|
| $C_{12}H_{14}N_2O_3S$ 1HCl | Requires | C 47.6 | H 5.0 | N 9.3% |

A mixture of 6-methoxy-7-(2-methylthioethoxy)-3,4-dihydroquinazolin-4-one (1.07 g, 4.0 mmol), thionyl chloride (20 ml) and DMF (4 drops) was heated at reflux for 2 hours and then allowed to cool. The excess thionyl chloride was removed by evaporation and the residue was azeotroped with toluene. The solid residue was partitioned between aqueous sodium hydrogen carbonate and methylene chloride, the organic phase was separated and washed with brine. The organic phase was passed through phase separating paper, and the solvent removed by evaporation to give 4-chloro-6-methoxy-7-(2-methylthioethoxy)quinazoline (810 mg, 71%).

MS-ESI: 285 [MH]$^+$

EXAMPLES 19 AND 20

3-Chloroperoxybenzoic acid (wet, 50–60%, 500 mg), (3-CPBA), was added to a solution of 4-(2-fluoro-5-hydroxy-4-methylanilino)-6-methoxy-7-(2-methylthioethoxy)quinazoline (485 mg, 1.2 mmol), (prepared as described for Example 18), in methylene chloride (90 ml) and DMA (6 ml). After 2 hours, 2 further portions of 3-CPBA were added (total 160 mg). The mixture was checked for remaining oxidant, and the volatiles were removed by evaporation. The 2 products were separated by column chromatography eluting with methylene chloride/methanol (9/1) to give 4-(2-fluoro-5-hydroxy-4-methylanilino)-6-methoxy-7-(2-(methylsulphonyl)ethoxy) quinazoline (94 mg, 19%).

¹H NMR Spectrum: (DMSOd₆) 2.15(s, 3H); 3.18(s, 3H); 3.70(t, 2H); 3.95(s, 3H); 4.50(t, 2H); 6.92(d, 1H); 6.97(d, 1H); 7.25(s, 1H); 7.83(s, 1H); 8.33(s, 1H); 9.27(s, 1H); 9.30(s, 1H)

MS-ESI: 422 [MH]⁺

| Elemental analysis: | Found | C 53.0 | H 4.9 | N 9.7 |
|---|---|---|---|---|
| C₁₉H₂₀N₃O₅SF 0.5H₂O | Requires | C 53.0 | H 4.9 | N 9.8% | and 4-(2-fluoro-5-hydroxy-4-methylanilino)-6-methoxy-7-(2-(methylsulphinyl)ethoxy)quinazoline (120 mg, 25%).

¹H NMR Spectrum: (DMSOd₆) 2.16(s, 3H); 2.69(s, 3H); 3.15(m, 1H); 3.37(m, 1H); 3.94(s, 3H); 4.53(m, 2H); 6.92(d, 1H); 6.97(d, 1H); 7.83(s, 1H); 8.32(s, 1H); 9.27(s, 1H); 9.30(s, 1H)

MS-ESI: 406 [MH]⁺

| Elemental analysis: | Found | C 55.5 | H 5.0 | N 10.0 |
|---|---|---|---|---|
| C₁₉H₂₀N₃O₄SF | Requires | C 56.0 | H 5.4 | N 10.3% |

EXAMPLE 21

A mixture of 6-methoxy-7-(2-(pyrrolidin-1-yl)ethoxy)-3,4-dihydroquinazolin-4-one (260 mg, 0.90 mmol), thionyl chloride (5 ml) and DMF (2 drops) was heated at reflux for 45 minutes and allowed to cool. The excess thionyl chloride was removed by evaporation, and the residue azeotroped with toluene. A solution of 4-chloro-2-fluoro-5-hydroxyaniline (160 mg, 1.0 mmol), (as described in EP 61741 A2), in isopropanol (5 ml) was added to the residue and the mixture was heated at reflux for 1 hour and then allowed to cool. The mixture was diluted with acetone, and the solid product collected by filtration, washed with acetone and dried to give 4-(4-chloro-2-fluoro-5-hydroxyanilino)-6-methoxy-7-(2-(pyrrolidin-1-yl)ethoxy)quinazoline hydrochloride(381 mg, 83%).

¹H NMR Spectrum: (DMSOd₆) 1.85–2.15(br m, 4H); 3.20(br s, 2H); 3.5–3.7(br mn, 4H); 4.°5(s, 3H); 4.65(t, 2H); 7.20(d, 1H); 7.5(m, 2H); 8.45(s, 1H); 8.80(s, 1H); 10.5(br s, 1H); 11.35(br s, 1H); 11.75(br s, 1H)

MS-ESI: 433 [MH]⁺

| Elemental analysis: | Found | C 49.7 | H 5.0 | N 10.6 |
|---|---|---|---|---|
| C₂₁H₂₂N₄O₃ClF 2HCl 0.17 isopropanol | Requires | C 50.1 | H 5.0 | N 10.9% |

The starting material was prepared as follows:

1-(2-Chloroethyl)pyrrolidine hydrochloride (1.27 g, 7.5 mmol) was added to 7-hydroxy-6-methoxy-4-phenoxyquinazoline (1.0 g, 3.7 mmol), (prepared as described for the starting material in Example 16), and potassium carbonate (3.9 g, 28.3 mmol) in DMF (30 ml). The mixture was heated at 110° C. for 4 hours and allowed to cool. The mixture was filtered, and the volatiles were removed from the filtrate by evaporation. The residue was purified by column chromatography eluting with methylene chloride/methanol/ammonia, (100/8/1) to give an oil which was triturated with ethyl acetate to give 6-methoxy-4-phenoxy-7-(2-(pyrrolidin-1-yl)ethoxy)quinazoline (200 mg, 15%) as a white solid.

¹H NMR Spectrum: (DMSOd₆) 1.65(m, 4H); 2.55(m, 4H); 2.85(t, 2H); 3.95(s, 3H); 4.25(t, 2H); 7.30(m 3H); 7.38(s, 1H); 7.50(m, 2H); 7.55(s, 1H); 8.5(s, 1H)

MS-ESI: 366 [MH]⁺

A mixture of 6-methoxy-4-phenoxy-7-(2-(pyrrolidin-1-yl)ethoxy)quinazoline (565 mg, 1.55 mmol) and 2M hydrochloric acid (5 ml) was heated at 90° C. for 90 minutes and allowed to cool. The solution was neutralised with aqueous sodium hydrogen carbonate, and the water removed by evaporation. The residue was purified by column chromatography eluting with methylene chloride/methanol/ammonia (100/8/1) to give 6-methoxy-7-(2-(pyrrolidin-1-yl)ethoxy)-3,4-dihydroquinazolin-4-one (480 mg). This material was used without further characterisation.

EXAMPLE 22

1M Ethereal hydrogen chloride (0.72 ml, 0.72 mmol) was added to 4-chloro-6-methoxy-7-(2-morpholinoethoxy)quinazoline (210 mg, 0.65 mmol) and 4-chloro-2-fluoro-5-hydroxyaniline (115 mg, 0.71 mmol), (as described in EP 61741 A2), in isopropanol (5 ml) and the mixture heated at reflux for 2 hours and then allowed to cool. The mixture was diluted with acetone and the precipitated product collected by filtration. The impure product was dissolved in methylene chloride/ammonia (100/1) and methanol, the insolubles removed by filtration and the volatiles were removed from the filtrate by evaporation. The solid residue was washed with water and dried to give 4-(4-chloro-2-fluoro-5-hydroxyanilino)-6-methoxy-7-(2-morpholinoethoxy) quinazoline (60 mg, 21%).

¹H NMR Spectrum: (DMSOd₆) 2.45–2.60(m, 4H); 2.78(t, 2H); 3.58(t, 4H); 3.94(s, 3H); 4.26(t. 2H); 7.17(d, 1H); 7.23(s, 1H); 7.38(d, 1H); 7.79(s, 1H); 8.37(s, 1H); 9.43(s, 1H); 10.17(s, 1H)

MS-ESI: 449 [MH]⁺

| Elemental analysis: | Found | C 53.5 | H 5.2 N 11.6 |
|---|---|---|---|
| C₂₁H₂₂N₄O₄ClF 1.25H₂O | Requires | C 53.5 | H 5.3 N 11.9% |

The starting material was prepared as follows:

1,2-Dibromoethane (1.6 ml, 18.6 mmol) was added to 7-hydroxy-6-methoxy-4-phenoxyquinazoline (0.5 g, 1.86 mmol), (prepared as described for the starting material in Example 16), and potassium carbonate (1.2 g, 8.7 mmol) in DMF (60 ml) and the mixture was heated at 85° C. for 2 hours, and was then allowed to cool. The insolubles were removed by filtration, and the volatiles were removed from the filtrate by evaporation to give a residue which was purified by column chromatography eluting with methylene chloride/methanol (97/3) to give 7-(2-bromoethoxy)-6-methoxy-4-phenoxyquinazoline (440 mg, 63%).

MS-ESI: 375 [MH]⁺

A mixture of morpholine (8 ml) and 7-(2-bromoethoxy)-6-methoxy-4-phenoxyquinazoline (450 mg, 1.2 mmol) was stirred at ambient temperature for 3 hours. The excess morpholine was removed by evaporation and the residue was partitioned between aqueous sodium hydrogen carbonate and methylene chloride. The organic phase was separated, passed through phase separating paper and the solvent removed by evaporation. Trituration of the residue with isohexane gave a solid which was collected by filtration and dried to give 6-methoxy-7-(2-morpholinoethoxy)-4-phenoxyquinazoline (410 mg, 90%).

MS-ESI: 382 [MH]⁺

A mixture of 6-methoxy-7-(2-morpholinoethoxy)-4-phenoxyquinazoline (400 mg, 1.05 mmol) and 2M hydrochloric acid (10 ml) was heated at 100° C. for 2 hours and then allowed to cool. The mixture was neutralised with solid sodium hydrogen carbonate. Addition of methylene chloride gave a white precipitate which was collected by filtration, washed with acetone and dried to give 6-methoxy-7-(2-morpholinoethoxy)-3,4-dihydroquinazolin-4-one (320 mg, 100%).

MS-ESI: 306 [MH]$^+$

A mixture of 6-methoxy-7-(2-morpholinoethoxy)-3,4-dihydroquinazolin-4-one (310 mg, 1.02 mmol), thionyl chloride (10 ml) and DMF (2 drops) was heated at reflux for 4 hours and allowed to cool. Excess thionyl chloride was removed by evaporation and the residue was azeotroped with toluene. The residue was partitioned between aqueous sodium hydrogen carbonate and methylene chloride. The organic layer was separated, washed with brine and filtered through phase separating paper. The volatiles were removed by evaporation and the residue purified by column chromatography eluting with methylene chloride\methanol (96/4) to give 4-chloro-6-methoxy-7-(2-morpholinoethoxy) quinazoline (225 mg, 68%).

MS-ESI: 324 [MH]$^+$

EXAMPLE 23

1M Ethereal hydrogen chloride (0.34 ml, 0.34 mmol) was added to 4-chloro-6-methoxy-7-(2-(4-methylpiperazin-1-yl) ethoxy)quinazoline (115 mg, 0.34 mmol) and 4-chloro-2-fluoro-5-hydroxyaniline (61 mg, 0.38 mmol), (as described in EP 61741 A2), in isopropanol (5 ml) and the mixture was heated at reflux for 90 minutes and then allowed to cool. The mixture was diluted with acetone, and the solid product collected by filtration. The impure solid was treated with methylene chloride/methanol/ammonia (100/8/1) (5 ml), and water was added. The reprecipitated product was collected by filtration and dried to give 4-(4-chloro-2-fluoro-5-hydroxyanilino)-6-methoxy-7-(2-(4-methylpiperazin-1-yl)ethoxy)quinazoline (32%).

$^1$H NMR Spectrum: (DMSOd$_6$) 2.28(s, 3H); 2.53(m, 4H); 2.60(m, 4H); 2.81 (t, 2H); 3.95(s, 3H); 4.25(t, 2H); 7.18(d, 1H); 7.20(s, 1H); 7.36(d, 1H); 7.80(s, 1H); 8.35(s, 1H); 9.43(s, 1H); 10.18(br s, 1H)

MS-ESI: 462 [MH]$^+$

| Elemental analysis: | Found | C 54.1 | H 5.3 N 14.0 |
|---|---|---|---|
| C$_{22}$H$_{25}$N$_5$O$_3$ClF 1.3H$_2$O | Requires | C 54.4 | H 5.7 N 14.4% |

The starting material was prepared as follows:

A mixture of 1-methylpiperazine (7 ml) and 7-(2-bromoethoxy)-6-methoxy4-phenoxyquinazoline (1.0 g, 2.67 mmol), (prepared as described for the starting material in Example 22), was stirred at ambient temperature for 5 hours. The excess 1-methylpiperazine was removed by evaporation and the residue was partitioned between aqueous sodium hydrogen carbonate and methylene chloride. The organic phase was separated, passed through phase separating paper and the volatiles removed by evaporation to give 6-methoxy-7-(2-(4-methylpiperazin-1-yl)ethoxy)-4-phenoxyquinazoline (970 mg, 92%).

$^1$H NMR Spectrum: (DMSOd$_6$) 2.21(s, 3H); 2.38(m, 4H); 2.58(m, 4H); 2.85(t, 2H); 4.02(s, 3H); 4.35(t, 2H); 7.39(m, 3H); 7.46(s, 1H); 7.55(m, 2H); 7.61(s, 1H); 8.59(s, 1H)

A mixture of 6-methoxy,7-(2-(4-methylpiperazin-1-yl) ethoxy)-4-phenoxyquinazoline (960 mg, 2.4 mmol) and 2M hydrochloric acid (20 ml) was heated at 95° C. for 2 hours and allowed to cool. The solution was basified with solid sodium hydrogen carbonate, the water removed by evaporation and the residue azeotroped with toluene. The residue was washed exhaustively with methylene chloride, the washings were combined, -insolubles removed by filtration and the solvent removed by evaporation to give 6-methoxy-7-(2-(4-methylpiperazin-1-yl)ethoxy)-3,4-dihydroquinazolin-4-one (500 mg, 66%).

MS-ESI: 319 [MH]$^+$

A mixture of 6-methoxy-7-(2-(4-methylpiperazin-1-yl) ethoxy)-3,4-dihydroquinazolin-4-one (500 mg, 1.57 mmol), thionyl chloride (20 ml) and DMF (3 drops) was heated at reflux for 3 hours and allowed to cool. The excess thionyl chloride was removed by evaporation, and the residue was azeotroped with toluene. The residue was treated with aqueous sodium hydrogen carbonate and the product was extracted with methylene chloride. The combined extracts were washed with brine, passed through phase separating paper and the solvent removed by evaporation to give 4-chloro-6-methoxy-7-(2-(4-methylpiperazin-1-yl)ethoxy) quinazoline (120 mg, 23%).

MS-ESI: 337 [MH]$^+$

EXAMPLE 24

A mixture of 6-methoxy-7-(2-piperidinoethoxy)-3,4-dihydroquinazolin-4-one (440 mg, 1.45 mmol), thionyl chloride (15 ml) and DMF (3 drops) was heated at reflux for 3 hours then allowed to cool. The excess thionyl chloride was removed by evaporation and the residue was azeotroped with toluene to give a crude 4-chloro-6-methoxy-7-(2-piperidinoethoxy)quinazoline hydrochloride (640 mg).

A sample (320 mg, 0.89 mmol) of this material was added to a solution of 4-chloro-2-fluoro-5-hydroxyquinazoline (130 mg, 0.8 mmol), (as described in EP 61741 A2), in isopropanol (10 ml) and the mixture heated at reflux for 90 minutes and allowed to cool. The mixture was diluted with acetone, and the precipitated product was collected by filtration and dried. The residue was purified by column chromatography eluting with methylene chloride/methanol/ammonia, (100/8/1). The pure product was dissolved in acetone and 1M ethereal hydrogen chloride (1 ml, 1 mmol) added. The resulting precipitate was collected by filtration and dried to give 4-(4-chloro-2-fluoro-5-hydroxyanilino)-6-methoxy-7-(2-piperidinoethoxy)quinazoline hydrochloride (137 mg, 32%).

$^1$H NMR Spectrum: (DMSOd$_6$) 1.75(br m, 6H); 4.00(s, 3H); 4.65(t, 2H); 7.15(d, 1H); 7.35(s, 1H); 7.42(d, 1H); 8.15(s, 1H); 8.60(s, 1H); 10.4(s, 1H); 10.6(br s, 2H)

MS-ESI: 447 [MH]$^+$

| Elemental analysis: | Found | C 51.0 | H 5.4 N 10.6 |
|---|---|---|---|
| C$_{22}$H$_{24}$N$_4$O$_3$ ClF 2HCl | Requires | C 50.8 | H 5.0 N 10.8% |

The starting material was prepared as follows:

1-(2-Chloroethyl)piperidine hydrochloride (0.83 g, 4.5 mmol) was added to 7-hydroxy-6-methoxy-4-phenoxyquinazoline (1.0 g, 3.73mmol), (prepared as described for the starting material in Example 16), and potassium carbonate (2.6 g, 18.8 mmol) in DMF (30 ml), and the mixture heated at 110° C. for 2.5 hours and allowed to cool. The insolubles were removed by filtration, and the volatiles were removed from the filtrate by evaporation. The residue was purified by column chromatography eluting with methylene chloride/methanol (9/1) to give 6-methoxy-4-phenoxy-7-(2-piperidinoethoxy)quinazoline (1.2 g, 85%).

$^1$H NMR Spectrum: (DMSOd$_6$) 1.38(m, 2H); 1.50(m, 4H); 2.4–2.5(m. 4H); 2.75(t, 2H); 3.95(s, 3H); 4.27(t, 2H); 7.30(m, 3H); 7.40(s, 1H); 7.46(m, 2H); 7.54(s, 1H); 8.52(s, 1H)

MS-ESI: 380 [MH]$^+$

A mixture of 6-methoxy-4-phenoxy-7-(2-piperidinoethoxy)quinazoline (1.15 g, 3.0 mmol) and 2M hydrochloric acid (20 ml) was heated at 90° C. for 2 hours and allowed to cool. The mixture was neutralised with solid sodium hydrogen carbonate and extracted with methylene chloride. The organic phase was separated, passed through phase separating paper and the volatiles removed by evaporation to give a solid product (230 mg). The aqueous phase was adjusted to pH10, the resulting precipitate was collected by filtration, washed with water and dried to give a second crop of product (220 mg). The products were combined to give 6-methoxy-7-(2-piperidinoethoxy)-3,4-dihydroquinazolin-4-one (450 mg, 50%).

MS-ESI: 304 [MH]$^+$

EXAMPLE 25

A mixture of 7-(2-cyclopentyloxyethoxy)-6-methoxy-3,4-dihydroquinazolin-4-one (260 mg, 0.85 mmol), thionyl chloride (5 ml) and DMF (2 drops) was -heated at reflux for 2 hours and allowed to cool. The excess thionyl chloride was removed by evaporation, and the residue was azeotroped with toluene. To the residue was added a solution of 4-chloro-2-fluoro-5-hydroxyaniline (140 mg, 0.87 mmol), (as described in EP 61741 A2), in isopropanol (5 ml) and the mixture was heated at reflux for 1 hour and allowed to cool. The suspension was diluted with acetone, and the precipitate collected by filtration. The crude product was dissolved in methylene chloride/methanol/ammonia (100/8/1, 2 ml), the insoluble material removed by filtration and the solvent removed from the filtrate by evaporation. The residue was dissolved in acetone, 1M ethereal hydrogen chloride (1 ml, 1 mmol) added and the resultant precipitate collected by filtration and dried to give 4-(4-chloro-2-fluoro-5-hydroxyanilino)-7-(2-cyclopentyloxyethoxy)-6-methoxyquinazoline hydrochloride (50 mg, 12%).

$^1$H NMR Spectrum: (DMSOd$_6$) 1.5–1.75(m, 8H); 3.75(m, 2H); 3.9–4.1(m, 1H); 4.00(s, 3H); 4.80(t. 2H); 7.20(m, 1H); 7.35(s, 1H); 7.50(d, 1H); 8.25(s, 1H); 8.75(s, 1H); 10.(br s, 1H); 11.4(br s, 1 H)

MS-ESI: 448 [MH]$^+$

Elemental analysis: Found C 54.1 H 4.8 N 8.5
$C_{22}H_{23}N_3O_4ClF$ 1HCl 0.1H$_2$O Requires C 54.4 H 5.0 N 8.6%

The starting material was prepared as follows:

2-Cyclopentyloxyethanol (4.3 g, 33.1 mmol) in pyridine (18 ml) was added dropwise to a solution of 3-toluenesulphonyl chloride (6.8 g, 35.7 mmol) in pyridine (27 ml) at 5° C. The mixture was allowed to warm to ambient temperature, and stirred overnight. The mixture was poured onto ice containing concentrated hydrochloric acid (46 ml) and the product was extracted with ether. The organic phase was washed with 2M hydrochloric acid, dried (MgSO$_4$) and the solvent removed by evaporation to give 2-cyclopentyloxyethyl 4-toluenesulphonate (6.9 g, 73%) which was used without further purification.

7-Hydroxy-6-methoxy-4-phenoxyquinazoline (1.11 g, 4.2 mmol), (prepared as described for the starting material in Example 16), in DMF (1 7 ml) was added to a suspension of sodium hydride (184 mg of a 60% suspension in oil, 4.6 mmol) in DMF (3 ml). The mixture was stirred until evolution of gas ceased, and then 2-cyclopentyloxyethyl 4-toluenesulphonate (1.25 g, 4.45mmol) in DMF (3 ml) was added dropwise. The mixture was stirred at ambient temperature for 30 minutes, then heated at 60° C. for 2 hours, and then at 80° C. for a further 4 hours before being allowed to cool. The mixture was poured onto ice and extracted with methylene chloride. The combined extracts were washed with brine, passed through phase separating paper and the solvent removed by evaporation. The residue was purified by column chromatography eluting with ethyl acetate. The purified product was triturated with isohexane to give 7-(2-cyclopentyloxyethoxy)-6-methoxy-4-phenoxyquinazoline (480 mg, 28%).

$^1$H NMR Spectrum: (DMSOd$_6$) 1.2–1.7m, (8H); 3.77(m, 2H); 3.95(s, 3H); 4.0(m, 1H); 4.25(m, 2H); 7.30(m, 3H); 7.38(s, 1H); 7.45(m, 2H); 7.55(s, 1H); 8.50 (s, 1H)

MS-ESI: 381 [MH]$^+$

A mixture of 7-(2-cyclopentyloxyethoxy)-6-methoxy-4-phenoxyquinazoline (470 mg, 1.2 mmol) and 2M hydrochloric acid (6 ml) was heated at 90° C. for 2 hours and allowed to cool. Water was added, and the product was extracted with methylene chloride. The combined extracts were washed with aqueous sodium hydrogen carbonate, passed through phase separating paper and the solvent was removed by evaporation. Trituration with ethyl acetate give 7-(2-cyclopentyloxyethoxy)-6-methoxy-3,4-dihydroquinazolin-4-one (270 mg, 74%).

MS-ESI: 305 [MH]$^+$

EXAMPLE 26

1M Aqueous sodium hydroxide solution (4 ml, 4 mmol) was added to a solution of 4-(2-fluoro-5-methoxycarbonyloxy4-methylanilino)-7-hydroxy-6-methoxyquinazoline (820 mg, 2.2 mmol) in methanol (20 ml) and the mixture stirred for 1 hour at ambient temperature. Concentrated hydrochloric acid (0.8 ml) was added, the volatiles removed by evaporation and the residue purified by column chromatography eluting with methylene chloride/methanol (60/40) to give 4-(2-fluoro-5-hydroxy4-methylanilino)-7-hydroxy-6-methoxyquinazoline (313 mg, 45%).

m.p. 276–278° C.

$^1$H NMR Spectrum: (DMSOd$_6$; CF$_3$COOD) 2.18(s, 3H); 4.0(s, 3H); 6.88(d, 1H); 7.12(d, 1H); 7.26(s, 1H); 8.08(s, 1H); 8.76(s, 1H)

MS-ESI: 316 [MH]$^+$

| Elemental analysis: | Found | C 54.4 | H 4.4 | N 11.5 |
| $C_{16}H_{14}N_3O_3F$ 1HCl 0.1H$_2$O | Requires | C 54.4 | H 4.3 | N 11.9% |

The starting material was prepared as follows:

A solution of (4-fluoro-2-methyl-5-nitrophenyl) methyl carbonate (3 g, 13 mmol), (prepared as described in EP 0307777 A2), in ethanol (60 ml) containing platinum(IV) oxide (300 mg) was stirred under hydrogen at 0.3 atmosphere for 1 hour. After filtration and evaporation of the solvent, 2-fluoro-5-methoxycarbonyloxy-4-methylaniline was isolated as a solid (2.6 g, 100%).

$^1$H NMR Spectrum: (CDCl$_3$) 2.07(s, 3H); 3.87(s, 3H); 6.52(d, 1H),, 6.80(d, 1H)

A solution of 7-benzyloxy4-chloro-6-methoxyquinazoline (800 mg, 2.6 mmol), (prepared as described for the starting material in Example 4 but with an aqueous work up), and 2-fluoro-5-methoxycarbonyloxy-4-methylaniline (570 mg, 2.89 mmol) in isopropanol (20 ml) was refluxed for 2 hours. After cooling to ambient temperature, the solid was filtered, washed with isopropanol and dried under vacuum to give 7-benzyloxy-4-(2-fluoro-5-methoxycarbonyloxy4-methylanilino)-6-methoxyquinazoline (1.0 g, 77%).

$^1$H NMR Spectrum: (DMSOd$_6$; CF$_3$COOD) 2.2(s, 3H); 3.85(s, 3H); 4.0(s, 3H); 5.37(s, 2H); 7.3–7.55(m. 8H); 8.13(s, 1H); 8.86(s, 1H)

MS-ESI: 464 [MH]$^+$

A solution of 7-benzyloxy-4-(2-fluoro-5-methoxycarbonyloxy-4-methylanilino)-6-methoxyquinazoline (700 mg, 1.4 mmol) in DMF (10 ml), methanol (10 ml) and trichloromethane (10 ml) containing 10% palladium-on-charcoal (100 mg) was stirred under 1 atmosphere of hydrogen for 1 hour. After filtration and evaporation of the solvent, the residue was triturated with ether, filtered and dried under vacuum to give 4-(2-fluoro-5-methoxycarbonyloxy-4-methylanilino)-7-hydroxy-6-methoxyquinazoline (570 mg, 98%).

$^1$H NMR Spectrum: (DMSOd$_6$) 2.23(s, 3H); 3.87(s, 3H); 4.01(s, 3H); 7.37(s, 1H); 7.45(d, 1H); 7.5(d, 1H); 8.20(s, 1H); 8.77(s, 1H); 11.35(s, 1H); 11.79(s, 1H)

MS-ESI: 374 [MH]$^+$

EXAMPLE 27

A solution of 4-chloro-7-(2-methoxyethoxy)quinazoline hydrochloride (275 mg, 1 mmol) and 2-fluoro-5-hydroxy4-methylaniline (170 mg, 1.2 mmol), (prepared as described for the starting material in Example 8), in 2-pentanol (5 ml) was heated at reflux for 2 hours. The mixture was allowed to cool and the precipitate was collected by filtration, washed with isopropanol and ether, and dried under vacuum at 70° C. to give 4-(2-fluoro-5-hydroxy-4-methylanilino)-7-(2-methoxyethoxy)quinazoline hydrochloride(295 mg, 78%) as a cream solid.

m.p. 217–220° C.

$^1$H NMR Spectrum: (DMSOd$_6$) 2.17(s, 3H); 3.36(s, 3H); 3.75(t, 2H); 4.34(t, 2H); 6.89(d, 1H); 7.11(d, 1H); 7.30(d, 1H); 7.52(dd, 1H); 8.66(d, 1H); 8.82(s, 1H); 9.68(s, 1H); 11.40(s, 1H)

MS-ESI: 344 [MH]$^+$

| Elemental analysis: | Found | C 56.8 | H 5.2 | N 11.1 |
|---|---|---|---|---|
| C$_{18}$H$_{18}$N$_3$O$_3$F 1HCl | Requires | C 56.9 | H 5.0 | N 11.1% |

The starting material was prepared as follows:

A solution of 2-amino-4-fluorobenzoic acid (3 g, 19.3 mmol) in formamide (30 ml) was heated at 150° C. for 6 hours. The reaction mixture was poured onto ice/water 1/1 (250 ml). The precipitated solid was collected by filtration, washed with water and dried to give 7-fluoro-3,4-dihydroquinazolin-4-one (2.6 g, 82%).

Sodium (400 mg, 17 mmol) was added carefully to 2-methoxyethanol (10 ml) and the mixture heated at reflux for 30 minutes. 7-Fluoro-3,4-dihydroquinazolin-4-one (750 mg, 4.57 mmol) was added to the resulting solution and the mixture heated at reflux for 15 hours. The mixture was cooled and poured into water (250 ml). The mixture was acidified to pH4 with concentrated hydrochloric acid. The resulting solid product was collected by filtration, washed with water and then with ether, and dried under vacuum to give 7-(2-methoxyethoxy) 3,4-dihydroquinazolin-4-one (580 mg, 58%).

A solution of 7-(2-methoxyethoxy)-3,4-dihydroquinazolin-4-one (500 mg, 2.2 mmol) in thionyl chloride (15 ml) and DMF (0.1 ml) was heated at reflux for 3 hours. The volatiles were removed by evaporation to give 4-chloro-7-(2-methoxyethoxy)quinazoline hydrochloride as a cream solid (520 mg, 83%).

EXAMPLE 28

A solution of 4-chloro-7-(2-methoxyethoxy)quinazoline hydrochloride (275 mg, 1.0 mmol), (prepared as described for the starting material in Example 27), and 4-chloro-2-fluoro-5-hydroxyaniline (193 mg, 1.2 mmol), (as described in EP 61741 A2), in 2-pentanol (5 ml) was heated at reflux for 2 hours. The mixture was allowed to cool and the precipitate was collected by filtration, washed with isopropanol and ether, and dried under vacuum at 70° C. to give 4-(4-chloro-2-fluoro-5-hydroxyanilino)-7-(2-methoxyethoxy)quinazoline hydrochloride (178 mg, 45%) as a cream solid.

m.p. 224–227° C.

$^1$H NMR Spectrum: (DMSOd$_6$) 3.36(s. 3H); 3.76(t, 2H); 4.34(t, 2H); 7.14(d, 1H); 7.3(d, 1H); 7.53(m, 2H); 8.66(d, 1H); 8.85(s, 1H); 10.58(s, 1H); 11.40(s, 1H)

MS-ESI: 364 [MH]$^+$

Elemental analysis: Found C 50.8 H 4.1 N 10.4
C$_{17}$H$_{15}$N$_3$O$_3$FCl 1HCl Requires C 51.0 H 4.0 N 10.5%

EXAMPLE 29

A solution of 4-(2-fluoro-5-methoxycarbonyloxy-4-methylanilino)-7-methoxyacetamidoquinazoline (201 mg, 0.5mmol) in methanol (5 ml) and 2M aqueous sodium hydroxide solution (0.5 ml) was stirred at ambient temperature for 1 hour. The mixture was diluted with water and adjusted to pH6 with 2M hydrochloric acid. The precipitated solid was collected by filtration, washed with water, dried and then dissolved in a mixture of methylene chloride and methanol. A 5M solution of hydrogen chloride in isopropanol (0.3 ml) was added and most of the solvent removed by evaporation. The precipitated solid was collected by filtration, washed with methylene chloride and dried under vacuum to give 4-(2-fluoro-5-hydroxy-4-methylanilino)-7-methoxyacetamidoquinazoline hydrochloride (70 mg, 36%) as a yellow solid.

m.p. 213–215° C.

$^1$H NMR Spectrum: (DMSOd$_6$; CF$_3$COOD) 2.18(s, 3H); 3.43(s, 3H); 4.16(s, 2H); 6.90(d, 1H); 7.12(d, 1H); 7.95(d, 1H); 8.56(s, 1H); 8.62(d, 1H); 8.86(s, 1H)

MS-ESI: 357 [MH]$^+$

| Elemental analysis: | Found | C 53.7 | H 4.9 | N 13.6 |
|---|---|---|---|---|
| C$_{18}$H$_{17}$N$_4$O$_3$F 1HCl 0.5H$_2$O | Requires | C 53.8 | H 4.8 | N 13.9% |

The starting material was prepared as follows:

A mixture of 7-nitro-3,4-dihydroquinazolin-4-one (5 g, 26 mmol) in thionyl chloride (50 ml) and DMF (1 ml) was heated at reflux for 1.5 hours. Excess thionyl chloride was removed by evaporation and the residue azeotroped with toluene. The residue was suspended in ether, collected by filtration and dried under vacuum to give 4-chloro-7-nitroquinazoline hydrochloride (6.4 g; 100%).

51

¹H NMR Spectrum: (DMSOd₆) 8.26(dd, 1H); 8.36(d, 1H); 8.40(s, 1H); 8.42(dd, 1H)

MS-ESI: 209 [MH]⁺

A solution of 4-chloro-7-nitroquinazoline hydrochloride (2.46 g, 10 mmol) and 2-fluoro-5-methoxycarbonyloxy-4-methylaniline (2.2 g, 11 mmol), (prepared as described for the starting material in Example 26), in isopropanol (25 ml) was heated at 50° C. for 1 hour. The mixture was allowed to cool, the precipitated solid was collected by filtration recrystallised from methylene chloride/methanol/isopropanol, to give 4-(2-fluoro-5-methoxycarbonyloxy-4-methylanilino)-7-nitroquinazoline hydrochloride (1.8 g, 45%) as a yellow solid.

¹H NMR Spectrum: (DMSOd₆) 2.21(s, 3H); 3.86(s, 3H); 7.40(d, 1H); 7.46(d, 1H); 8.49(dd, 1H); 8.63(s, 1H); 8.84(s, 1H); 8.89(d, 1H)

MS-ESI: 373 [MH]⁺

| Elemental analysis: | Found | C 50.0 | H 3.6 | N 13.8 |
|---|---|---|---|---|
| C₁₇H₁₃N₄O₅F 1HCl | Requires | C 50.0 | H 3.5 | N 13.7% |

A mixture of 4-(2-fluoro-5-methoxycarbonyloxy-4-methylanilino)-7-nitroquinazoline hydrochloride (5.3 g, 13 mmol) and 10% palladium-on-charcoal catalyst (1 g) in ethanol (100 ml), 7M ethanolic hydrogen chloride (1.8 ml) and methanol (20 ml) was stirred under hydrogen at 1.7 atmospheres for 75 minutes. The catalyst was removed by filtration through diatomaceous earth and the filter pad thoroughly washed with methylene chloride, methanol and ether and the solvent was removed from the filtrate by evaporation to give 7-amino-4-(2-fluoro-5-methoxycarbonyloxy-4-methylanilino)quinazoline hydrochloride (4.8 g, 97%) as a yellow solid.

¹H NMR Spectrum: (DMSOd₆) 2.22(s, 3H); 3.87(s, 3H); 6.77(s, 1H); 7.08(dd, 1H); 7.15(m, 2H); 7.41(m, 2H); 8.35 (d, 1H); 8.63(s, 1H); 11.03(s, 1H)

MS-ESI: 343 [MH]⁺

Methoxyacetyl chloride (119 mg, 1.1 mmol) followed by triethylamine (232 mg, 2.3 mmol) were added to a suspension of 7-amino-4-(2-fluoro-5-methoxycarbonyloxy-4-methylanilino)quinazoline hydrochloride (415 mg, 1.1 mmol) in methylene chloride (10 ml) and the mixture stirred for 1 hour. The solvent was removed by evaporation and the residue partitioned between ethyl acetate and water. The organic layer was separated, washed with brine, dried (MgSO₄) and the solvent removed by evaporation. The resulting solid was purified by column chromatography eluting with methylene chloride/acetonitrile 50/50 followed by methylene chloride/acetonitrile/methanol 50/45/5 to give 4-(2-fluoro-5-methoxycarbonyloxy-4-methylanilino)-7-methoxyacetamidoquinazoline (250 mg, 60%) as a yellow solid.

¹H NMR Spectrum: (DMSOd₆) 2.18(s, 3H); 3.41 (s, 3H); 3.85(s, 3H); 4.09(s, 2H); 7.30(d, 1H); 7.44(d, 1H); 7.84(d, 1H); 8.22(s, 1H); 8.36(d, 1H); 8.44(s, 1H); 9.74(s, 1H); 10.21(s, 1H)

MS-ESI: 437 [MNa]⁺

EXAMPLE 30

1M Aqueous sodium hydroxide solution (2.1 ml, 2.1 mmol) was added to a solution of 4-(2-fluoro-5-methoxycarbonyloxy-4-methylanilino)-7-hydroxyquinazoline hydrochloride (400 mg, 1.05 mmol), in

52 methanol (10 ml) and the mixture stirred for 50 minutes at ambient temperature. The solvent was removed by evaporation, the residue dissolved in water and adjusted to pH7 with hydrochloric acid. The aqueous mixture was extracted with ethyl acetate, the extracts washed with brine, dried (MgSO₄) and the solvent removed by evaporation. The residue was purified by column chromatography eluting with methylene chloride/methanol 95/5 and 80/20. The purified solid was dissolved in methanol and saturated methanolic hydrogen chloride was added. The volatiles were removed by evaporation, the residue was triturated with pentane to give 4-(2-fluoro-5-hydroxy-4-methylanilino)-7-hydroxyquinazoline (149 mg, 44%) as a yellow solid.

m.p. 274–278° C.

¹H NMR Spectrum: (DMSOd₆) 2.16(s, 3H); 6.87(d, 1H); 7.10(d, 1H); 7.22(d, 1H); 7.32(ss, 1H); 8.57(d, 1H); 8.76(s, 1H); 9.66(s, 1H); 11.24(s, 1H); 11.70(s, 1H)

MS-ESI: 285 [MH]⁺

| Elemental analysis: | Found | C 54.2 | H 4.1 | N 12.3 |
|---|---|---|---|---|
| C₁₅H₁₂N₃O₂F 1HCl 0.3H₂O 0.05NaCl | Requires | C 54.6 | H 4.2 | N 12.7% |

The starting material was prepared as follows:

Sodium (368 mg, 16 mmol) was added to benzyl alcohol (10 ml, 96 mmol) and the mixture was heated at 148° C. for 30 minutes, 7-fluoro-3,4-dihydroquinazolin-4-one (656 mg, 4 mmol), (J. Chem. Soc. section B 1967,449), was added and the mixture maintained at 148° C. for 24 hours. The reaction mixture was allowed to cool, the solution was poured on to water (1 70 ml) and the aqueous mixture adjusted to pH3 with concentrated hydrochloric acid. The precipitate was collected by filtration, washed with water, ether and dried under vacuum to give 7-benzyloxy-3,4-dihydroquinazolin-4-one (890 mg, 89%) as a white solid.

m.p. 267–269° C.

¹H NMR Spectrum: (DMSOd₆; CF₃COOD) 5.32(s, 2H); 7.25(d, 1 H); 7.32–7.52(m, 6H); 8.12(d, 1H); 8.99(s, 1H)

MS-ESI: 252 [MH]⁺

| Elemental analysis: | Found | C 71.4 | H 4.9 | N 10.7 |
|---|---|---|---|---|
| C₁₅H₁₂N₂O₂ 0.04H₂O | Requires | C 71.2 | H 4.8 | N 11.1 |

A mixture of 7-benzyloxy-3,4-dihydroquinazolin-4-one (800 mg, 3.17 mmol) in thionyl chloride (20 ml, 0.27 mmol) and DMF (100 µl) was heated at reflux for 3 hours Excess thionyl chloride was removed by evaporation and the residue azeotroped with toluene and dried under vacuum to give 7-benzyloxy-4-chloroquinazoline hydrochloride (835 mg, 86%) as a cream solid.

m.p. 131–132° C.

¹H NMR Spectrum: (DMSOd₆; CF₃COOD) 5.32(s, 2H); 7.29(d, 1H); 7.34–7.52(m, 6H); 8.12(d, 1H); 9.03(s, 1H)

MS-ESI: 270 [MH]⁺

2-Fluoro-5-methoxycarbonyloxy-4-methylaniline (883 mg, 4.4 mmol), (prepared as described for the starting material in Example 26), was added to a solution of 7-benzyloxy-4-chloroquinazoline hydrochloride (1 g, 3.7 mmol) in 2-pentanol (15 ml) at 120° C. and the mixture was then heated at reflux for 4 hours. The precipitate was collected by filtration, washed with isopropanol followed by ether and dried under vacuum to give 7-benzyloxy-4-(2-fluoro-5-methoxycarbonyloxy-4-methylanilino)quinazoline hydrochloride (1.65 g, 97%/) as a cream solid.

m.p. 219–220° C.

$^1$H NMR Spectrum: (DMSOd$_6$) 2.22(s, 3H); 3.86(s, 3H); 5.37(s, 2H); 7.30–7.60(m, 9H); 8.60(d, 1H); 8.80(s, 1H); 11.2(s, 1H)

MS-ESI: 434 [MH]$^+$

| Elemental analysis: | Found | C 60.1 | H 4.9 | N 8.5 |
|---|---|---|---|---|
| C$_{24}$H$_{20}$N$_3$O$_4$F 1HCl 0.5H$_2$O | Requires | C 60.2 | H 4.6 | N 8.8 |

7-Benzyloxy-4-(2-fluoro-5-methoxycarbonyloxy-4-methylanilino)quinazoline hydrochloride (1.53 g, 3.25 mmol) and 10% palladium-on-charcoal catalyst (1 80 mg) in a mixture of methanol/DMF/trichloromethane (75 ml, 6 ml, 30 ml) was stirred under hydrogen at 1.5 atmospheres for 45 minutes. The catalyst was removed by filtration through diatomaceous earth and the solvent removed from the filtrate by evaporation. The residue was triturated with ether, the resulting solid collected by filtration and dried under vacuum to give 4-(2-fluoro-5-methoxycarbonyloxy-4-methylanilino)-7-hydroxyquinazoline hydrochloride (1.23 g, 84%) as an orange solid.

m.p. 205–210° C.

$^1$H NMR Spectrum: (DMSOd$_6$) 2.22(s, 3H); 3.85(s, 3H); 7.24(d, 1H); 7.35(dd, 1I); 7.42(d, 1H); 7.45(d, 1H); 8.58(d, 1H); 8.81(s, 1H); 11.40(s, 1H); 11 76(s, 1H)

MS-ESI: 344 [MH]$^+$

EXAMPLE 31

2M Aqueous sodium hydroxide solution (453 µl, 0.9 mmol) was added to a suspension of 4-(2-fluoro-5-methoxycarbonyloxy-4-methylanilino)-7-(3-morpholinopropionamido)quinazoline (219 mg, 0.45 mmol) in methanol (6 ml) and the mixture stirred for 1 hour. The reaction mixture was diluted with water and then adjusted to pH6 with 2M hydrochloric acid. The resulting precipitate was collected by filtration, washed with water and ethanol, and dried. The solid was dissolved in methylene chloride/methanol and a 5M solution of hydrogen chloride in isopropanol (0.3 ml) added. The volatiles were removed by evaporation, the resulting solid was washed with ether, and dried under vacuum to give 4-(2-fluoro-5-hydroxy-4-methylanilino)-7-(3-morpholinopropionamido)quinazoline (1–86 mg, 80%) as a yellow solid.

m.p. 228–233° C.

$^1$H NMR Spectrum: (DMSOd$_6$; CF$_3$COOD) 2.21(s, 3H); 3. 1 (t, 2H); 3.22(t, 2H); 3.5–3.6(m, 4H); 3.8(t, 2H); 4.05(d, 2H); 6.94(d, 1H); 7.10(d, 1H); 7.88(d, 1H); 8.55(s, 1H); 8.7(d, 1H); 8.9(s, 1H)

MS-ESI: 426 [MH]$^+$

| Elemental analysis: | Found | C 52.1 | H 5.8 | N 13.4 |
|---|---|---|---|---|
| C$_{22}$H$_{24}$N$_5$O$_3$F 1.9HCl 0.6H$_2$O 0.2isopropanol | Requires | C 52.5 | H 5.6 | N 13.5 |

The starting material was prepared as follows:

Potassium hydroxide (485 mg, 8.6mmol) was added to a solution of methyl 3-morpholinopropionate (1 g, 5.7 mmol) in ethanol (20 ml) and the mixture stirred for 2 hours at 80° C. The solution was allowed to cool and adjusted to pH1 with 6M hydrochloric acid. Insoluble material was removed by filtration and the volatiles removed from the filtrate by evaporation. The resulting oil was triturated with ether, the solid product collected by filtration, washed with methylene chloride and dried under vacuum to give 3-morpholinopropionic acid (993 mg, 89%) as a white solid.

$^1$H NMR Spectrum: (DMSOd$_6$; CF$_3$COOD) 2.83(t, 2H); 3.13(t, 2H); 3.36(t, 2H); 3.46(d, 2H); 3.73(t, 2H); 3.97(d, 2H)

MS-ESI: 159 [MH]$^+$ 1,3-Dicyclohexylcarbodiimide (343 mg, 1.6 mmol) was added to a suspension of 3-morpholinopropionic acid (325 mg, 1.6 mmol) in pyridine (12 ml) and the mixture stirred for 10 minutes. 7-Amino-4-(2-fluoro-5-methoxycarbonyloxy-4-methylanilino)quinazoline hydrochloride (370 mg, 0.97 mmol), (prepared as described for the starting material in Example 29), was added and the mixture stirred for 32 hours. 3-Morpholinopropionic acid (57 mg, 0.29 mmol) followed by 1,3-dicyclohexylcarbodiimide (100 mg, 0.48 mmol) was added and the mixture stirred for a further 18 hours. The solvent was removed by evaporation, the residue partitioned between water and ethyl acetate and the aqueous layer adjusted to pH8 with a saturated solution of sodium hydrogen carbonate. The organic layer was separated, washed with brine, dried (MgSO$_4$), and the solvent removed by evaporation. The residue was purified by column chromatography eluting with methylene chloride/methanol (95/5) to give 4-(2-fluoro-5-methoxycarbonyloxy-4-methylanilino)-7-(3-morpholinopropionamido)quinazoline (226 mg, 48%) as a white solid.

$^1$H NMR Spectrum: (DMSOd$_6$) 2–18(s, 3H); 2A-2.5(m, 4H); 2.5–2.6(m, 2H); 2.62–2.7(m, 2H); 3.58(t, 4H); 3.85(s, 3H); 7.30(d, 1H); 7.44(d, 1H); 7.7(d, 1H); 8.13(s, 1H); 8.35(d, 1H); 8.41 (s, 1H); 9.7(s, 1H); 10.46(s, 1H)

EXAMPLE 32

2M Aqueous sodium hydroxide solution (760 µl, 1.5 mmol) was added to a solution of 4-(2-fluoro-5-methoxycarbonyloxy4-methylanilino)-7-(2-methoxyethylamino)quinazoline (304 mg, 0.76 mmol) in methanol (8 ml) at 5° C. and the mixture then stirred for 30 minutes at ambient temperature. The mixture was diluted with water and adjusted to pH6 with 2M hydrochloric acid. The precipitated solid was collected by filtration and then suspended in methylene chloride/methanol. A 5M solution of hydrogen chloride in isopropanol (0.4 ml) was added and the volatiles were removed from the resulting solution by evaporation. The residue was triturated with ether, the solid product collected by filtration, washed with ether and dried under vacuum to give 4-(2-fluoro-5-hydroxy-4-methylanilino)-7-(2-methoxyethylamino)quinazoline hydrochloride (260 mg, 90%) as yellow solid.

m.p. 192–197° C.

$^1$H NMR Spectrum: (DMSOd$_6$) 2.16(s, 3H); 3.32(s, 3H); 3.38(m, 2H); 3.58(m, 2H); 6.71(bs, 1H); 6.88(d, 1H); 7.1(d, 1H); 7.2(d, 1H); 7.73(m, 1H); 8.37(d, 1H); 8.61(s, 1H); 9.66(s, 1H); 10.95(s, 1H)

MS-ESI: 343 [MH]$^+$

The starting material was prepared as follows:

A solution of methoxyacetaldehyde dimethyl acetal (1.27 g, 10 mol) in water (7 ml) and 2M hydrochloric acid (76 µl) was heated at 50–60° C. for 2 hours. The mixture was allowed to cool and adjusted to pH7.5 with saturated aqueous sodium hydrogen carbonate solution. This solution was added to a suspension of 7-amino-4-(2-fluoro-5-methoxycarbonyloxy-4-methylanilino)quinazoline hydrochloride (400 mg, 1 mmol), (prepared as described for the starting material in Example 30), in ethanol (32 ml) and acetic acid (95 µl, 1.5 mmol). The mixture was then stirred for 5 minutes, sodium cyanoborohydride (133 mg, 2 mmol) added and the solution adjusted to pH5.5 with glacial acetic acid. The mixture was stirred for 18 hours and the organic solvents removed by evaporation and the resulting aqueous mixture partitioned between ethyl acetate and water. The organic layer was separated, washed with brine, dried ($MgSO_4$) and the solvent removed by evaporation. The residue was purified by column chromatography eluting with methylene chloride/methanol (96/4 followed by 12/8) to give 4-(2-fluoro-5-methoxycarbonyloxy-4-methylanilino)-7-(2-methoxyethylamino)quinazoline (308 mg, 77%) as a yellow foam.

$^1$H NMR Spectrum: ($DMSOd_6$; $CF_3COOD$) 2.22(s, 3H); 3.33(s, 3H); 3.41(t, 2H); 3.60(t, 2H); 3.87(s, 3H); 6.68(br s, 1H); 7.22(dd, 1H); 7.37(d, 1H); 7.43(d, 1H); 8.30(d, 1H); 8.7(s, 1H)

EXAMPLE 33

2M Aqueous sodium hydroxide solution (620 µl) was added dropwise to a suspension of 4-(2-fluoro-5-methoxycarbonyloxy-4-methylanilino)-6-methoxy-7-methoxyacetamidoquinazoline (275 mg, 0.62 mmol) in methanol (8 ml) at 5° C. and the mixture then stirred for 90 minutes at ambient temperature. The reaction mixture was diluted with water and adjusted to pH7 with 2M hydrochloric acid. The precipitated solid was collected by filtration, resuspended in ethanol and a 5M solution of hydrogen chloride in isopropanol (0.3 ml) added. The volatiles were removed from the resulting solution by evaporation and the solid washed with ether collected by filtration and dried under vacuum to give 4-(2-fluoro-5-hydroxy-4-methylanilino)-6-methoxy-7-methoxyacetamidoquinazoline hydrochloride (216 mg, 82%).

m.p. 300–306° C.

$^1$H NMR Spectrum: ($DMSOd_6$) 2.18(s, 3H); 3.47(s, 2H); 4.13(s, 3H); 4.21(s, 3H); 6.92(d, 1H); 7.13(d, 1H); 8.41(s, 1H); 8.80(s, 1H); 8.90(s, 1H); 9.54(s, 1H); 9.72(s, 1H); 11.49(s, 1H)

MS-ESI: 387 [MH]$^+$

| Elemental analysis: | Found | C 52.3 | H 4.8 | N 12.7 |
|---|---|---|---|---|
| $C_{19}H_{19}N_4O_4F$ 1HCl 0.6$H_2O$ | Requires | C 52.6 | H 4.9 | N 12.9 |

The starting material was prepared as follows:

Acetic anhydride (50 ml) was added dropwise to a solution of 4-methoxy-2-methylaniline (49.7 g, 360mmol) in DMA (200 ml) at 5° C. and the mixture stirred for 4.5 hours at ambient temperature. The solvent was removed by evaporation and the resulting solid washed with water and dried under vacuum to give N-(4-methoxy-2-methylphenyl)acetamide (57.3 g, 88%).

$^1$H NMR Spectrum: ($CDCl_3$) 2.16(s, 3H); 2.21(s, 3H); 3.77(s, 3H); 6.7–6.75(m, 2H); 7.42(d, 1H)

A mixture of tin(IV)chloride (1 9.3 ml) and 69.5% nitric acid (10.3 ml) in methylene chloride (140 ml) was added dropwise to a solution of N-(4-methoxy-2-methylphenyl)acetamide (28 g, 0.14 mol) in methylene chloride (500 ml) cooled to and maintained at −30° C. The reaction mixture was stirred at −30° C. for 1.5 hours, allowed to warm to ambient temperature then poured on to ice/water. The organic layer was separated and the aqueous layer extracted with ethyl acetate. The combined extracts were dried ($MgSO_4$), the solvent removed by evaporation and the residue purified by column chromatography eluting with petroleum ether/ethyl acetate (2/8) to give N-(4-methoxy-2-methyl-5-nitrophenyl)acetamide (1 7.8 g, 51%)

$^1$H NMR Spectrum: ($DMSOd_6$) 2.06(s, 3H); 2.29(s, 3H); 3.9(s, 3H); 7.24(s, 1H); 7.99(s, 1H); 9.41(s, 1H)

Potassium permanganate (68 g) was added portionwise to a solution of N-(4-methoxy-2-methyl-5-nitrophenyl)acetamide (35 g, 0.156 mol) and magnesium sulphate (38.5 g) in water (2.31) at 75° C. The mixture was maintained at 75° C. for 3.5 hours, further magnesium sulphate (4 g) and potassium permanganate (12 g) were added and stirring continued for 30 minutes at 75° C. The insolubles were removed from the hot reaction mixture by filtration through diatomaceous earth, the filtrate cooled and was acidified to pH 1 with concentrated hydrochloric acid. The precipitated solid was collected by filtration, washed with water and the aqueous filtrate extracted with ethyl acetate. The solid product and the ethyl acetate extract were combined and extracted with 2M aqueous sodium hydroxide solution. The basic aqueous layer was separated, washed with ethyl acetate, acidified with concentrated hydrochloric acid and re-extracted with ethyl acetate. The ethyl acetate extract was washed with brine, dried ($MgSO_4$) and the solvent removed by evaporation to give 2-acetamido-5-methoxy4-nitrobenzoic acid (21.6 g, 54%) as a yellow solid.

$^1$H NMR Spectrum: ($DMSOd_6$) 2.12(s, 3H); 3.93(s, 3H); 7.74(s, 1H); 8.75(s, 1H)

A solution of 2-acetamido-5-methoxy-4-nitrobenzoic acid (21.6 g, 85 mmol) in water (76 ml) and concentrated hydrochloric acid (30.5 ml) was heated at reflux for 3 hours. The reaction mixture was cooled to 0° C., the resulting solid was collected by filtration, washed with water and dried under vacuum to give 2-amino-5-methoxy-4-nitrobenzoic acid (I 6.6 g, 92%).

$^1$H NMR Spectrum: ($DMSOd_6$) 3.79(s, 3H); 7.23(s, 1H); 7.52(s, 1H); 8.8(br s, 2H)

A solution of 2-amino-5-methoxy-4-nitrobenzoic acid (1 6.6 g, 78 mmol) in formamide (250 ml) was heated at reflux for 4.5 hours. The reaction mixture was cooled to 0° C., diluted with water and the resulting precipitate collected by filtration, washed with water and dried under vacuum to give 6-methoxy-7-nitro-3,4-dihydroquinazolin-4-one ( 11.56 g, 67%).

$^1$H NMR Spectrum: ($DMSOd_6$; $CF_3COOD$) 4.02(s, 3H); 7.8(s, 1H); 8.12(s, 1H); 8.18(s, 1H)

A suspension of 6-methoxy-7-nitro-3,4-dihydroquinazolin-4-one (8 g, 36 mmol) in thionyl chloride (150 ml) and DMF (0.8 ml) was heated at reflux for 3 hours. Excess thionyl chloride was removed by evaporation and the residue azeotroped with toluene. The resulting solid was triturated with ether, collected by filtration and dried under vacuum to give 4-chloro-6-methoxy-7-nitroquinazoline hydrochloride(7.5 g, 75%).

$^1$H NMR Spectrum: ($DMSOd_6$) 4.13(s, 3H); 7.8(s, 1H); 8.7(s, 1H); 9.13(s, 1H)

A mixture of 4-chloro-6-methoxy-7-nitroquinazoline hydrochloride (784 mg, 2.8 mmol) and 2-fluoro-5-methoxycarbonyloxy-4-methylaniline (621 mg, 3.1 mmol), (prepared as described for the starting material in Example 26), in isopropanol (10 ml) was heated at reflux for 2 hours. The mixture was allowed to cool, the precipitated product collected by filtration, washed with isopropanol, ether and dried under vacuum to give 4-(2-fluoro-5-methoxycarbonyloxy-4-methylanilino)-6-methoxy-7-nitroquinazoline hydrochloride (1.12 g, 90%).

$^1$H NMR Spectrum: (DMSOd$_6$) 2.22(s, 3H); 3.86(s, 3H); 4.10(s, 3H); 7.41(d, 1H); 7.46(d, 1H); 8.40(s, 1H); 8.55(s, 1H); 8.77(s, 1H); 11.4(br s, 1H)

MS-ESI: 403 [MH]$^+$

A mixture of 4-(2-fluoro-5-methoxycarbonyloxy-4-methylanilino)-6-methoxy-7-nitroquinazoline hydrochloride (1.1 g, 25 mmol) and 10% palladium-on-charcoal catalyst (220 mg) in methanol (200 ml) and ethanol (10 ml) was stirred under hydrogen at 2.7 atmospheres for 7 hours. The catalyst was removed by filtration through diatomaceous earth, the solvent removed from the filtrate by evaporation and the solid residue washed with ether, collected by filtration and dried under vacuum to give 7-amino4-(2-fluoro-5-methoxycarbonyloxy-4-methylanilino)-6-methoxyquinazoline hydrochloride (930 mg, 91%).

$^1$H NMR Spectrum: (DMSOd$_6$) 2.22(s, 3H); 3.87(s, 3H); 4.02(s, 3H); 6.9(s, 1H); 7.4–7.5(m, 2H); 7.99(s, 1H); 8.62(s, 1 H)

MS-ESI: 372 [MH]$^+$

Methoxyacetyl chloride (62 μl, 0.68 mmol) was added dropwise to a solution of 7-amino-4-(2-fluoro-5-methoxycarbonyloxy-4-methylanilino)-6-methoxyquinazoline hydrochloride (215 mg, 0.52 mmol) in methylene chloride (5 ml) and pyridine (1.5 ml) at 0° C. and the mixture stirred for 2 hours at 0° C. Further methoxyacetyl chloride (14 μl, 0.15 mmol) was added and the mixture stirred for 20 minutes at 0° C. The reaction mixture was partitioned between ethyl acetate and water and the aqueous layer adjusted to pH9 with saturated aqueous sodium hydrogen carbonate solution. The organic layer was separated, washed with brine, dried (MgSO$_4$) and the solvent removed by evaporation. The residue was purified by column chromatography eluting with methylene chloride/acetonitrile/methanol (60138/2) to give 4-(2-fluoro-5-methoxycarbonyloxy-4-methylanilino)-6-methoxy-7-methoxyacetamidoquinazoline (1 75 mg, 75%) as a white solid.

$^1$H NMR Spectrum: (DMSOd$_6$) 2.21(s, 3H); 3.47(s, 2H); 3.87(s, 3H); 4.07(s, 3H); 4.15(s, 3H); 7.35(d, 1H); 7.45(d, 1H); 7.96(s, 1H); 8.40(s, 1H); 8.65(s, 1H); 9.28(s, 1H); 9.65(s, 1H)

EXAMPLE 34

A solution of ethereal hydrogen chloride (1.0 ml of a 1.0M solution, 1.0 mmol) was added to 4-chloro-6-methoxy-7-(2-thiomorpholinoethoxy)quinazoline (340 mg, 1.0 mmol) and 4-chloro-2-fluoro-5-hydroxyaniline (200 mg, 1.2 mmol), (as described in EP 61741 A2), in t-butanol (15 ml). The mixture was heated at 95° C. for 1 hour and then stirred for 18 hours at ambient temperature. The reaction mixture was diluted with acetone and the precipitated product collected by filtration, washed with acetone and dried to give 4-(4-chloro-2-fluoro-5-hydroxyanilino)-6-methoxy-7-(2-thiomorpholinoethoxy)quinazoline hydrochloride hemihydrate (480 mg, 88%) as beige powder.

$^1$H NMR Spectrum: (DMSOd$_6$) 3.67(t, 2H); 4.04(s, 3H); 4.70(t, 2H); 7.18(d, 1H); 7.4–7.5(m, 2H); 7.51(dd, 1H); 8.44(s, 1H); 8.82(s, 1H); 10.6(br s, 1H); 11.7(br s, 1H)

MS-ESI: 465 [MH]$^+$

| Elemental analysis: | Found | C 45.8 | H 4.4 | N 10.0 |
|---|---|---|---|---|
| $C_{21}H_{22}N_4ClFO_3S$ 2HCl 0.5H$_2$O | Requires | C 46.1 | H 4.6 | N 10.2% |

The starting material was prepared as follows:

1,2-Dibromoethane (19.2 ml, 286 mmol) was added to 7-hydroxy-6-methoxy-4-phenoxyquinazoline (6.0 g, 22 mmol), (prepared as described for the starting material in Example 16), and potassium carbonate (14.4 g, 107 mmol) in DMF. The mixture was stirred at 85° C. for 2.5 hours, allowed to cool and insoluble material was removed by filtration. The solvent was removed by evaporation and the residue purified by column chromatography eluting with methylene chloride/methanol (93/7). The product was triturated with ethyl acetate to give 7-(2-bromoethoxy)-6-methoxy-4-phenoxyquinazoline (5.3 g, 63%). A mixture of 7-(2-bromoethoxy)-6-methoxy-4-phenoxyquinazoline (2.0 g, 5.3 mmol) in thiomorpholine (15 ml) was stirred at ambient temperature for 5 hours. The mixture was diluted with water and the resulting precipitate collected by filtration. The solid product was dissolved in methylene chloride, washed with brine and passed through phase separating paper. The solvent was removed by evaporation to give 6-methoxy-4-phenoxy-7-(2-thiomorpholinoethoxy)quinazoline (2.0 g, 94%) as a pale yellow solid.

MS-ESI: 398 [MH]$^+$

A mixture of 6-methoxy-4-phenoxy-7-(2-thiomorpholinoethoxy)quinazoline (2.0 g, 5 mmol) in 2M hydrochloric acid (25 ml) was heated at 90° C. for 1.5 hours. The mixture was allowed to cool and adjusted to pH7 with solid sodium hydrogen carbonate. Methylene chloride was added and the resulting semi-solid product was isolated by decanting and filtering the aqueous mixture. This product was dissolved in acetone and insoluble material was removed by filtration. The solvent was removed by evaporation and the residue azeotroped with toluene to give 6-methoxy-7-(2-thiomorpholinoethoxy)-3,4-dihydroquinazolin-4-one (1.5 g, 92%) as a white solid.

MS-ESI: 322 [MH]$^+$

A mixture of 6-methoxy-7-(2-thiomorpholinoethoxy)-3,4-dihydroquinazolin-4-one (1.5 g, 4.6 mmol), thionyl chloride (25 ml) and DMF (0.2 ml) was heated at reflux for 2 hours. Excess thionyl chloride was removed by evaporation and the residue azeotroped with toluene. The resulting gum was partitioned between aqueous sodium hydrogen carbonate solution and methylene chloride. The organic layer was separated and the aqueous layer extracted with methylene chloride (4×40 ml). The combined extracts were passed through phase separating paper, the solvent removed by evaporation and the residue purified by column chromatography eluting with methylene chloride/methanol (95/5). The purified product was triturated with acetone to give 4-chloro-6-methoxy-7-(2-thiomorpholinoethoxy)quinazoline (400 mg, 25%) as an orange/brown solid.

MS-ESI: 342 [MH]$^+$

EXAMPLE 35

A solution of ethereal hydrogen chloride (1.0 ml of a 1.0M solution, 1.0 mmol) was added to 4-chloro-6-methoxy-7-(2-(2-methoxyethylamino)ethoxy)quinazoline (110 mg, 3.5 mmol) and 4-chloro-2-fluoro-5-hydroxyaniline (72 mg, 4.5 mmol), (as described in EP 61741 A2), in t-butanol (5 ml). The mixture was heated at 95° C. for 1 hour, allowed to cool and diluted with acetone. The precipitated product was collected by filtration, washed with methylene chloride and acetone and dried to give 4-(4-chloro-2-fluoro-5-hydroxyanilino)-6-methoxy-7-(2-(2-methoxyethylamino) ethoxy)quinazoline hydrochloride hydrate (110 mg, 59%) as a beige powder.

$^1$H NMR Spectrum: (DMSOd$_6$) 3.2–3.6(m, 4H); 3.38(s, 3H); 3.73(t, 2H); 4.09(s, 3H); 4.58(t, 2H); 7.24(d, 1H); 7.52(d, 1H); 7.55(s, 1H); 8.48(s, 1H); 7.85(s, 1H); 9.35(br s, 1H); 10.65(br s, 1H); 11.75(br s, 1H)

MS-ESI: 437 [MH]$^+$

Elemental analysis: Found C 45.1 H 4.6 N 10.1

C$_{20}$H$_{22}$N$_4$ClFO$_4$ 2HCl 1.2H$_2$O Requires C 45.2 H 5.0 N 10.5%

The starting material was prepared as follows:

A mixture of 7-(2-bromoethoxy)-6-methoxy-4-phenoxyquinazoline (1.1 g, 2.9 mmol), (prepared as described for the starting material in Example 22), in 2-methoxyethylamine (8 ml) was stirred at ambient temperature for 4 hours. The mixture was diluted with water and extracted with methylene chloride (5×25 ml). The combined extracts were washed with brine and passed through phase separating paper. The solvent was removed by evaporation and the residue purified by column chromatography eluting with methylene chloride/methanol/aqueous ammonia (100/8/1) to give 6-methoxy-4-phenoxy-7-(2-(2-methoxyethylamino)ethoxy)quinazoline (760 mg, 70%) as a white solid.

MS-ESI: 370 [MH]$^+$

A mixture of 6-methoxy-4-phenoxy-7-(2-(2-methoxyethylamino)ethoxy)quinazoline (760 mg, 2 mmol) in 2M hydrochloric acid (5 ml) was heated at 90° C. for 1.5 hours. The mixture was allowed to cool and adjusted to pH7 with solid sodium hydrogen carbonate. The water was removed by evaporation and the residue extracted with methylene chloride/methanol/aqueous ammonia (100/8/1). The volatiles were removed from the extract by evaporation, the residue dissolved in methylene chloride, passed through phase separating paper and the solvent removed by evaporation to give 6-methoxy-7-(2-(2-methoxyethylamino) ethoxy)-3,4-dihydroquinazolin-4-one (600 mg, 99%) as a white solid.

A mixture of 6-methoxy-7-(2-(2-methoxyethylamino) ethoxy)-3,4-dihydroquinazolin-4-one (300 mg, 1 mmol), thionyl chloride (5 ml) and DMF (0.1 ml) was heated at reflux for 45 minutes. Excess thionyl chloride was removed by evaporation and the residue azeotroped with toluene. The resulting gum was partitioned between aqueous sodium hydrogen carbonate solution and methylene chloride. The organic layer was separated and the aqueous layer extracted with methylene chloride (4×40 ml). The combined extracts were passed through phase separating paper and the solvent removed by evaporation to give 4-chloro-6-methoxy-7-(2-(2-methoxyethylamino)ethoxy)quinazoline (120 mg, 38%) as a yellow solid.

EXAMPLE 36

A solution of 4-chloro-6-methoxy-7-(3-morpholinopropoxy)quinazoline (202 mg, 0.6 mmol) and 5M isopropanolic hydrogen chloride (1.5 ml) in isopropanol (5 ml) was heated at 80° C. for 18 hours. The mixture was allowed to cool and the volatiles were removed by evaporation. The residue was partitioned between methylene chloride and water and the aqueous layer was adjusted to pH6.5 with 0.1M aqueous sodium hydroxide. The organic layer was separated, washed with water and brine, dried (MgSO$_4$) and the solvent removed by evaporation. The residue was purified by column chromatography eluting with methylene chloride/methanol (95/5). The purified solid was dissolved in methylene chloride/methanol and 2.2M ethereal hydrogen chloride was added. The volatiles were removed by evaporation, the solid residue was suspended in ether, collected by filtration, washed with ether and dried under vacuum to give 4-(4-bromo-2,6-difluoroanilino)-6-methoxy-7-(3-morpholinopropoxy)quinazoline hydrochloride (91 mg, 26%).

$^1$H NMR Spectrum: (DMSOd$_6$; CF$_3$COOD) 2.3–2.4(m, 2H); 3–1–3.2(m, 2H); 3.3–3.4(m, 2H); 3.55(d, 2H); 3.75(t, 2H); 4.01(d, 2H); 4.03(s, 3H); 4.35(t, 2H); 7.43(s, 1H); 7.76(d, 2H); 8.21(s, 1H); 8.93(s, 1H)

MS-ESI: 511 [MH]$^+$

| Elemental Analysis: | Found | C 45.4 H 4.7 N 9.2 |
|---|---|---|
| C$_{22}$H$_{23}$N$_4$O$_3$BrF$_2$ 0.3H$_2$O 1.85 HCl 0.09 ether 0.05 CH$_2$Cl$_2$ | Requires | C 45.4 H 4.5 N 9.4% |

The starting material was prepared as follows:

Diethyl azodicarboxylate (2.67 ml, 17 mmol) was added dropwise to a solution of 3-morpholinopropan-1-ol (1.54 g, 10 mmol), 7-hydroxy-3,4-dihydro-6-methoxy-3-((pivaloyloxy)methyl)quinazolin-4-one (2.6 g, 8.5 mmol) and triphenylphosphine (4.45 g, 17 mmol) in methylene chloride (40 ml). After stirring for 2 hours at ambient temperature, the volatiles were removed by evaporation. The residue was purified by column chromatography eluting with methylene chloride/methanol (97/3 followed by 95/5) to give 3,4-dihydro-6-methoxy-3-((pivaloyloxy)metyl)-7-(3-morpholinopropoxy)quinazolin-4-one (3.6 g, 97%).

$^1$H NMR Spectrum: (DMSOd$_6$; CF$_3$COOD) 1.12(s, 9H); 2.2–2.3(m, 2H); 3.1–3.2(m, 2H); 3.32(t, 2H); 3.55(d, 2H); 3.65–3.75(m, 2H); 3.92(s, 3H); 4.05(d, 2H); 4.25(t, 2H); 5.93(s, 2H); 7.23(s, 1H); 7.54(s, 1H); 8.41(s, 1H)

A solution of 3,4-dihydro-6-methoxy-3-((pivaloyloxy) methyl)-7-(3-morpholinopropoxy)quinazolin-4-one (4.93 g, 11.4 mmol) in a saturated solution of methanolic ammonia (70 ml) was stirred at ambient temperature for 2 days. The volatiles were removed by evaporation. The solid residue was suspended in ether, collected by filtration, washed with ether and dried under vacuum to give 4-hydroxy-6-methoxy-7-(3-morpholinopropoxy)quinazoline (2.87 g, 79%).

$^1$H NMR Spectrum: (DMSOd6; CF$_3$COOD) 2.2–2.3(m, 2H); 3.15(t, 2H); 3.35(t, 2H); 3.55(d, 2H); 3.7(t, 2H); 3.94(s, 3H); 4.05(d, 2H); 4.26(t, 2H); 7.29(s, 1H); 7.56(s, 1H); 8.96(s, 1H)

A solution of 4-hydroxy-6-methoxy-7-(3-morpholinopropoxy)quinazoline (2.87 g, 9 mmol) and DMF (1 ml) in thionyl chloride (35 ml) was refluxed for 45 minutes. After addition of toluene, the volatiles were removed by evaporation. The residue was partitioned between ethyl acetate and water and the aqueous layer was adjusted to pH8 with 2M aqueous sodium hydroxide. The organic layer was washed with water and brine, dried (MgSO$_4$) and the volatiles were removed by evaporation. The solid residue was purified by column chromatography eluting with a mixture of methylene chloride, acetonitrile and methanol (50/47.5/2.5) to give 4-chloro-6-methoxy-7-(3-morpholinopropoxy)quinazoline (2 g, 66%).

¹H NMR Spectrum: (CDCl₃) 2.13(m, 2H); 2.48(br s, 4H); 2.56(t, 2H); 3.72(t, 4H); 4.05(s, 3H); 4.29(t, 2H); 7.37(d, 2H); 8.86(s, 1H)

EXAMPLE 37

The following illustrate representative pharmaceutical dosage forms containing the compound of formula I, or a pharmaceutically acceptable salt thereof (hereafter compound X), for therapeutic or prophylactic use in humans:

| (a) Tablet I | mg/tablet |
| --- | --- |
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
| --- | --- |
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
| --- | --- |
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d) Capsule | mg/capsule |
| --- | --- |
| Compound X | 10 |
| Lactose Ph. Eur | 488.5 |
| Magnesium stearate | 1.5 |

| (e) Injection I | (50 mg/ml) |
| --- | --- |
| Compound X | 5.0% w/v |
| 1N Sodium hydroxide solution | 15.0% v/v |
| 0.1N Hydrochloric acid (to adjust pH to 7.6) | |
| Polyethylene glycol 400 | 4.5% w/v |
| Water for injection to 100% | |

| (f) Injection II | 10 mg/ml |
| --- | --- |
| Compound X | 1.0% w/v |
| Sodium phosphate BP | 3.6% w/v |
| 0.1N Sodium hydroxide solution | 15.0% v/v |
| Water for injection to 100% | |

| (g) Injection III | (1 mg/ml, buffered to pH 6) |
| --- | --- |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note
The above formulations may be obtained by conventional procedures well known in the pharmaceutical art. The tablets (a)–(c) may be enteric coated by conventional means, for example to provide a coating of cellulose acetate phthalate.

What is claimed is:
1. A compound of the formula I:

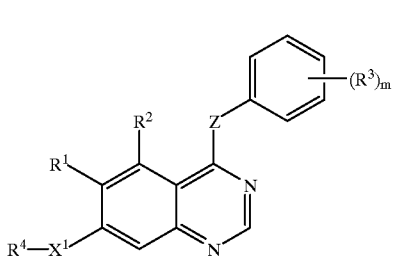

(I)

wherein:

Z represents —O—, —NH— or —S—;

m is an integer from 1 to 5 with the proviso that where Z is —NH— m is an integer from 3 to 5;

$R^1$ represents hydrogen, hydroxy, halogeno, nitro, trifluoromethyl, cyano, $C_{1-3}$alkyl $C_{1-3}$alkoxy, $C_{1-3}$alkylthio, or —NR⁵R⁶ (wherein $R^5$ and $R^6$, which may be the same or different, each represents hydrogen or $C_{1-3}$alkyl);

$R^2$ represents hydrogen, hydroxy, halogeno, methoxy, amino or nitro;

$R^3$ represents hydroxy, halogeno, $C_{1-3}$alkyl, $C_{1-3}$alkoxy, $C_{1-3}$alkanoyloxy, trifluoromethyl, cyano, amino or nitro;

$X^1$ represents —O—, —S—, —SO—, —SO₂—, —NR⁷—, —NR⁸CO—, —CONR⁹—, —SO₂NR¹⁰— or —NR¹¹SO₂—, (wherein $R^7$, $R^8$, $R^9$, $R^{10}$ and $R^{11}$ each represents hydrogen, $C_{1-3}$alkyl or $C_{1-3}$alkoxyC$_{2-3}$alkyl);

$R^4$ is selected from one of the following seven groups:

1) hydrogen, $C_{1-5}$hydroxyalkyl, $C_{1-5}$fluoroalkyl, $C_{1-5}$ aminoalkyl;

2) $C_{1-5}$alkylX²COR¹² (wherein $X^2$ represents —O— or —NR¹³— (in which $R^{13}$ represents hydrogen, $C_{1-3}$alkyl or $C_{1-3}$alkoxyC$_{2-3}$alkyl) and $R^{12}$ represents $C_{1-3}$alkyl, —NR¹⁴R¹⁵ or —OR¹⁶ (wherein $R^{14}$, $R^{15}$ and $R^{16}$ which may be the same or different each represents hydrogen, $C_{1-3}$alkyl or $C_{1-3}$alkoxyC$_{2-3}$alkyl));

3) $C_{1-5}$alkylX³R¹⁷ (wherein $X^3$ represents —O—, —S—, —SO—, —SO₂—, —OCO—, —NR¹⁸CO—, —CONR¹⁹—, —SO₂NR²⁰, —NR²¹SO₂— or —NR²²— (wherein $R^{18}$, $R^{19}$, $R^{20}$, $R^{21}$ and $R^{22}$ each independently represents hydrogen, $C_{1-3}$alkyl or $C_{1-3}$alkoxyC$_{2-3}$alkyl) and $R^{17}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{1-5}$alkylR²³ (wherein $R^{23}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);

5) $C_{2-5}$alkenylR²³ (wherein $R^{23}$ is as defined hereinbefore);

6) $C_{2-5}$alkynyl$R^{23}$ (wherein $R^{23}$ is as defined hereinbefore); and

7) $C_{1-5}$alkyl$X^4C_{1-5}$alkyl$X^5R^{24}$ (wherein $X^4$ and $X^5$ which may be the same or different are each —O—, —S—, —SO—, —SO$_2$—, —NR$^{25}$CO—, —CONR$^{26}$—, —SO$_2$NR$^{27}$—, —NR$^{28}$SO$_2$— or —NR$^{29}$— (wherein $R^{25}$, $R^{26}$, $R^{27}$, $R^{28}$ and $R^{29}$ each independently represents hydrogen, $C_{1-3}$alkyl or $C_{1-3}$alkoxy$C_{2-3}$alkyl) and $R^{24}$ represents hydrogen or $C_{1-3}$alkyl);

and salts thereof.

2. The compound as claimed in claim 1 wherein $R^1$ is hydrogen, hydroxy, cyano, nitro, trifluoromethyl, methyl, ethyl, methoxy, or ethoxy.

3. The compound as claimed in claim 1 wherein $R^2$ is hydrogen.

4. The compound as claimed in claim 1 wherein the phenyl group bearing $(R^3)_m$ is of the formula II:

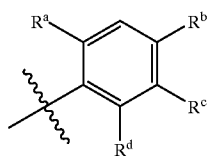

(II)

wherein:
$R^a$ represents hydrogen, methyl, fluoro or chloro;
$R^b$ represents hydrogen, methyl, methoxy, bromo, fluoro or chloro;
$R^c$ represents hydrogen or hydroxy; and
$R^d$ represents hydrogen, fluoro or chloro.

5. The compound as claimed in claim 1 wherein Z is NH.

6. The compound as claimed in claim 1 wherein Z is —O—.

7. The compound as claimed in claim 1 wherein $X^1$ represents —O—, —S—, —NR$^8$CO—, —NR$^{11}$SO$_2$— (wherein $R^8$ and $R^{11}$ each independently represents hydrogen or $C_{1-2}$alkyl) or NH.

8. The compound as claimed in claim 1 wherein $R^4$ is selected from one of the following nine groups:

1) $C_{2-5}$hydroxyalkyl, $C_{1-5}$fluoroalkyl;

2) $C_{2-3}$alkyl$X^2$CO$R^{12}$ (wherein $X^2$ is as defined in claim 1 and $R^{12}$ represents $C_{1-3}$alkyl, —NR$^{14}R^{15}$ or —OR$^{16}$ (wherein $R^{14}$, $R^{15}$ and $R^{16}$ which may be the same or different are each $C_{1-2}$alkyl or $C_{1-2}$alkoxyethyl));

3) $C_{2-4}$alkyl$X^3R^{17}$ (wherein $X^3$ is as defined in claim 1 and $R^{17}$ is a group selected from $C_{1-3}$alkyl, cyclopentyl, cyclohexyl, pyrrolidinyl and piperidinyl which group is linked to $X^3$ through a carbon atom and which $C_{1-3}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{1-4}$alkyl$R^{30}$ (wherein $R^{30}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{-4}$alkyl through a carbon atom and which group may carry one or two substituents selected from oxo, hydroxy, halogeno, $C_{1-2}$alkyl, $C_{1-2}$hydroxyalkyl and $C_{1-2}$alkoxy) or $C_{2-4}$alkyl$R^{31}$ (wherein $R^{31}$ is a group selected from morpholino, thiomorpholino, pyrrolidin-1-yl, piperazin-1-yl and piperidino which group may carry one or two substituents selected from oxo, hydroxy, halogeno, $C_{1-2}$alkyl, $C_{1-2}$hydroxyalkyl and $C_{1-2}$alkoxy);

5) $C_{3-4}$alkenyl$R^{30}$ (wherein $R^{30}$ is as defined herein);

6) $C_{3-4}$alkynyl$R^{30}$ (wherein $R^{30}$ is as defined herein);

7) $C_{3-4}$alkenyl$R^{31}$ (wherein $R^{31}$ is as defined herein);

8) $C_{3-4}$alkynyl$R^{31}$ (wherein $R^{31}$ is as defined herein); and

9) $C_{2-3}$alkyl$X^4C_{2-3}$alkyl$X^5R^{24}$ (wherein $X^4$ and $X^5$ are as defined in claim 1 and $R^{24}$ represents hydrogen or $C_{1-3}$alkyl).

9. The compound as claimed in claim 1 wherein $R^4$ is selected from one of the following five groups:

1) $C_{2-3}$hydroxyalkyl, $C_{1-3}$fluoroalkyl;

2) 2-(3,3-dimethylureido)ethyl, 3-(3,3-dimethylureido) propyl, 2-(3-methylureido)ethyl, 3-(3-methylureido) propyl, 2-ureidoethyl, 3-ureidopropyl, 2-N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl;

3) $C_{2-3}$alkyl$X^3R^{17}$ (wherein $X^3$ is as defined in claim 1 and $R^{17}$ is a group selected from $C_{1-2}$alkyl, cyclopentyl, cyclohexyl, pyrrolidinyl and piperidinyl which group is linked to $X^3$ through a carbon atom and which $C_{1-2}$alkyl group may bear one or two substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{1-2}$alkyl$R^{30}$ (wherein $R^{30}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or. $C_{2-3}$alkyl$R^{31}$ (wherein $R^{31}$ is a group selected from morpholino, thiomorpholino, piperidino, piperazin-1-yl and pyrrolidin-1-yl which group may carry one substituent selected from oxo, hydroxy, halogeno, $C_{1-2}$alkyl, $C_{1-2}$hydroxyalkyl and-$C_{1-2}$alkoxy); and 5) $C_{2-3}$alkyl$X^4C_{2-3}$alkyl$X^5R^{24}$ (wherein $X^4$ and $X^5$ are as defined in claim 1 and $R^{24}$ represents hydrogen or $C_{1-2}$alkyl).

10. The compound as claimed in claim 1 wherein $R^4$ represents trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl) ethyl, 2-(N-methylsulphamoyl)ethyl, 2-sulphamoylethyl, 2-(N,N-dimethylamino)ethyl, 3-(N,N-dimethylamino) propyl, 2-morpholinoethyl, 3-morpholinopropyl, 2-piperidinoethyl, 3-piperidinopropyl, 2-(piperazin-1-yl) ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1, 3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-thiomorpholinoethyl, 3-thiomorpholinopropyl, 2-(4-methylpiperazin-1-yl)ethyl, 3-(4-methylpiperazin-1-yl)propyl or 2-(2-methoxyethoxy) ethyl.

11. The compound as claimed in claim 1 wherein $R^4$ represents 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-thiomorpholinoethyl, 3-thiomorpholinopropyl, 2-(4-methylpiperazin-1-yl)ethyl, 3-(4-methylpiperazin-1-yl)propyl or 2-(2-methoxyethoxy)ethyl.

12. A compound selected from the group consisting of:
   4-(2-fluoro-5-hydroxy-4-methylanilino)-6-methoxy-7-(2-methoxyethoxy)quinazoline;
   4-(2-fluoro-5-hydroxy-4-methylanilino)-7-methoxyacetamidoquinazoline;
   4-(4-bromo-2,6-difluoroanilino)-6-methoxy-7-(3-morpholinopropoxy)quinazoline;
and salts thereof.

13. A compound selected from the group consisting of:
   4-(4-chloro-2-fluoro-5-hydroxyanilino)-6-methoxy-7-(2-(pyrrolidin-1-yl)ethoxy)quinazoline;
   4-(2-fluoro-5-hydroxy-4-methylanilino)-6-methoxy-7-(2-methylthioethoxy)quinazoline;
   4-(2-fluoro-5-hydroxy-4-methylanilino)-6-methoxy-7-(3-morpholinopropoxy)quinazoline;
   4-(4-chloro-2-fluoro-5-hydroxyanilino)-6-methoxy-7-(2-methoxyethoxy)quinazoline;
   7-(2-acetoxyethoxy)-4-(2-fluoro-5-hydroxy-4-methylanilino)-6-methoxyquinazoline;
   4-(4-chloro-2-fluoro-5-hydroxyanilino)-6-methoxy-7-(2-morpholinoethoxy)quinazoline;
   4-(4-chloro-2-fluoro-5-hydroxyanilino)-6-methoxy-7-(2-piperidinoethoxy)quinazoline;
   4-(2-fluoro-5-hydroxy-4-methylanilino)-7-(2-methoxyethylamino)quinazoline;
   4-(4-chloro-2-fluoro-5-hydroxyanilino)-6-methoxy-7-(2-cyclopentyloxyethoxy)quinazoline;
   4-(2,4-difluoro-5-hydroxyanilino)-6-methoxy-7-(2-methoxyethoxy)quinazoline;
and salts thereof.

14. A compound selected from the group consisting of:
   4-(4-chloro-2-fluoro-5-hydroxyanilino)-6-methoxy-7-(2-thiomorpholinoethoxy)quinazoline;
   4-(4-chloro-2-fluoro-5-hydroxyanilino)-6-methoxy-7-(3-morpholinopropoxy)quinazoline;
   4-(2-fluoro-5-hydroxy-4-methylanilino)-7-(2-hydroxyethoxy)-6-dimethoxyquinazoline;
   4-(4-chloro-2-fluoro-5-hydroxyanilino)-6-methoxy-7-(2-(4-methylpiperazin-1-yl)ethoxy)quinazoline;
   4-(2-fluoro-5-hydroxy-4-methylanilino)-7-(2-methoxyethoxy)quinazoline;
   4-(2-fluoro-5-hydroxy-4-methylanilino)-6-methoxy-7-(2-(methylsulphinyl)ethoxy)quinazoline;
and salts thereof.

15. The compound as claimed in any one of claims 1, 12, 13 and 14 in the form of a pharmaceutically acceptable salt.

16. A process for the preparation of a compound of formula I or salt thereof (as defined in claim 1 which comprises:

(a) the reaction of a compound of the formula III:

(III)

(wherein $R^1$, $R^2$, $X^1$ and $R^4$ are as defined in claim 1 and $L^1$ is a displaceable moiety), with a compound of the formula IV:

(IV)

(wherein Z, $R^3$ and m are as defined in claim 1) whereby to obtain compounds of the formula I and salts thereof;

(b) for the preparation of compounds of formula I and salts thereof in which the group of formula IIa:

(IIa)

(wherein $R^3$ and m are as defined in claim 1) represents a phenyl group carrying one or more hydroxy groups, the deprotection of a compound of formula V:

(V)

(wherein $X^1$, m, $R^1$, $R^2$, $R^3$, $R^4$ and Z are as defined in claim 1, P represents a phenolic hydroxy protecting group and $p^1$ is an integer from 1 to 5 equal to the number of protected hydroxy groups and such that m—$p^1$ is equal to the number of $R^3$ substituents which are not protected hydroxy);

(c) for the preparation of those compounds of formula I and salts thereof wherein the substituent $X^1$ is —O—, —S— or —$NR^7$—, (wherein $R^7$ is as defined in claim 1), the reaction of a compound of the formula VI:

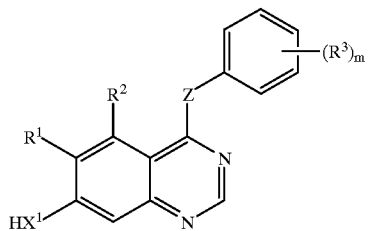

(wherein m, $X^1$, $R^1$, $R^2$, $R^3$, and Z are as defined in claim 1) with a compound of formula VII:

$$R^4—L^1 \quad \text{(VII)}$$

(wherein $R^4$ is as defined in claim 1 and $L^1$ is as herein defined);

(d) the reaction of a compound of the formula VIII:

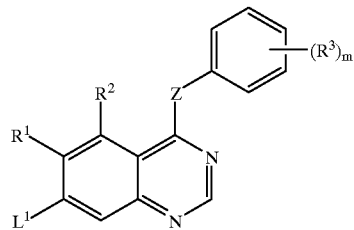

(wherein $R^1$, $R^2$, $R^3$, Z and m are all as defined in claim 1 and $L^1$ is as herein defined) with a compound of the formula IX:

$$R^4—X^1—H \quad \text{(IX)}$$

(wherein $R^4$ and $X^1$ are as defined in claim 1);

(e) for the preparation of compounds of formula I and salts thereof wherein $R^4$ is $C_{1-5}$alkyl$R^{32}$, wherein $R^{32}$ is selected from one of the following four groups:
1) $X^6C_{1-3}$alkyl (wherein $X^6$ represents —O—, —S—, —SO_2—, —NR^{33}CO— or —NR^{34}SO_2— (wherein $R^{33}$ and $R^{34}$ are each independently hydrogen, $C_{1-3}$alkyl or $C_{1-3}$alkoxy$C_{2-3}$alkyl);
2) $NR^{35}R^{36}$ (wherein $R^{35}$ and $R^{36}$ which may be the same or different are each hydrogen, $C_{1-3}$allyl or $C_{1-3}$alkoxy$C_{2-3}$alkyl);
3) $X^7C_{1-5}$alkyl$X^5R^{24}$ (wherein $X^7$ represents —O—, —S—, —SO_2—, —NR^{37}CO—, —NR^{38}SO_2— or —NR^{39}— (wherein $R^{37}$, $R^{38}$ and $R^{39}$ are each independently hydrogen, $C_{1-3}$alkyl or $C_{1-3}$alkoxy$C_{2-3}$alkyl) and $X^5$ and $R^{24}$ are as defined in claim 1); and
4) $R^{31}$ (wherein $R^{31}$ is a 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-4}$alkyl, $C_{1-4}$hydroxyalkyl and $C_{1-4}$alkoxy);

the reaction of a compound of the formula X:

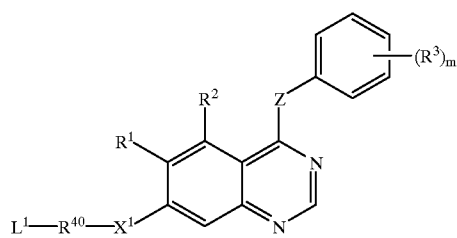

(wherein $X^1$, $R^1$, $R^2$, $R^3$, Z and m are as defined in claim 1, $L^1$ is as defined herein and $R^{40}$ is $C_{1-5}$alkyl) with a compound of the formula XI:

$$R^{32}—h \quad \text{(XI)}$$

(wherein $R^{32}$ is as defined herein);

(f) for the preparation of those compounds of formula I and salts thereof wherein the substituent $R^1$ is represented by $NR^5R^6$, where one or both of $R^5$ and $R^6$ are $C_{1-3}$alkyl and/or the substituent $R^4$—$X^1$ is an alkylamino or dialkylamino group, the reaction of compounds of formula I wherein the substituent $R^1$ and/or the substituent $R^4$—$X^1$ is an amino group with an alkylating agent;

(g) for the preparation of those compounds of formula I and salts thereof wherein one or more of the substituents $R^1$, $R^2$ or $R^3$ is an amino group or where $R^4$—$X^1$ is an amino group, the reduction of a corresponding compound of formula I wherein the substituent(s) at the corresponding position(s) of the quinazoline and/or phenyl ring is/are a nitro group(s);

and when a salt of a compound of formula I is required, reaction of the compound obtained with an acid or base whereby to obtain the desired salt.

17. A pharmaceutical composition which comprises as active ingredient the compound of formula I as defined in claim 1 or a pharmaceutically acceptable salt thereof in association with a pharmaceutically acceptable excipient or carrier.

18. A method for producing an antiangiogenic and/or vascular permeability reducing effect in a warm-blooded animal in need of such treatment which comprises administering to said animal an effective amount of a compound of formula I or a pharmaceutically acceptable salt thereof as defined in claim 1.

* * * * *